(12) United States Patent
Dantus et al.

(10) Patent No.: US 7,609,731 B2
(45) Date of Patent: Oct. 27, 2009

(54) LASER SYSTEM USING ULTRA-SHORT LASER PULSES

(75) Inventors: Marcos Dantus, Okemos, MI (US);
Vadim V. Lozovoy, Okemos, MI (US);
Matthew Comstock, Milford, MI (US)

(73) Assignee: Board of Trustees Operating Michigan State University, East Lansing, MI (US)

( * ) Notice: Subject to any disclaimer, the term of this patent is extended or adjusted under 35 U.S.C. 154(b) by 469 days.

(21) Appl. No.: 10/791,377

(22) Filed: Mar. 2, 2004

(65) Prior Publication Data
US 2004/0233944 A1    Nov. 25, 2004

Related U.S. Application Data

(63) Continuation-in-part of application No. 10/265,211, filed on Oct. 4, 2002, now Pat. No. 7,450,618, which is a continuation-in-part of application No. PCT/US02/02548, filed on Jan. 28, 2002.

(60) Provisional application No. 60/265,133, filed on Jan. 30, 2001.

(51) Int. Cl.
*H01S 3/13* (2006.01)
(52) U.S. Cl. .............................. 372/30; 372/9; 372/22; 372/25
(58) Field of Classification Search .............. 372/43.01, 372/50.1, 9, 22, 25–27; 250/288, 281, 282, 250/423
See application file for complete search history.

(56) References Cited

U.S. PATENT DOCUMENTS

| | | | |
|---|---|---|---|
| 3,919,881 A | 11/1975 | Metherell | |
| 3,988,704 A | 10/1976 | Rice et al. | |
| 4,288,691 A | 9/1981 | Horton | |
| 4,655,547 A | 4/1987 | Heritage et al. | |
| 4,746,193 A | 5/1988 | Heritage et al. | |
| 4,772,854 A | 9/1988 | Silberberg | |
| 4,819,239 A | 4/1989 | Sharp et al. | |

(Continued)

FOREIGN PATENT DOCUMENTS

JP    2003 155256 A    5/2003

(Continued)

OTHER PUBLICATIONS

Kroner, D. et al., Asymmetric Laser Excitation in Chiral Molecules: Quantum Simulations for a Proposed Experiment, Chemical Physics Letters Elsevier Netherland, vol. 372, No. 1-2, Apr. 22, 2003, pp. 242-248.

(Continued)

*Primary Examiner*—Minsun Harvey
*Assistant Examiner*—Delma R Forde
(74) *Attorney, Agent, or Firm*—Harness, Dickey & Pierce, P.L.C.

(57) ABSTRACT

A laser system using ultrashort laser pulses is provided. In another aspect of the present invention, the system includes a laser, pulse shaper and detection device. A further aspect of the present invention employs a femtosecond laser and binary pulse shaping (BPS). Still another aspect of the present invention uses a laser beam pulse, a pulse shaper and a SHG crystal.

99 Claims, 23 Drawing Sheets

U.S. PATENT DOCUMENTS

| | | | |
|---|---|---|---|
| 4,856,860 A | 8/1989 | Silberberg et al. | |
| 4,866,699 A | 9/1989 | Brackett et al. | |
| 4,913,934 A | 4/1990 | Sharp et al. | |
| 4,928,316 A | 5/1990 | Heritage et al. | |
| 5,034,613 A | 7/1991 | Denk | |
| 5,048,029 A | 9/1991 | Skupsky et al. | |
| 5,132,824 A | 7/1992 | Patel et al. | |
| 5,239,607 A | 8/1993 | da Silva et al. | |
| 5,341,236 A | 8/1994 | Stappaerts | |
| 5,359,410 A | 10/1994 | Diels et al. | |
| 5,406,408 A | 4/1995 | Ellingson et al. | |
| 5,414,540 A | 5/1995 | Patel et al. | |
| 5,414,541 A | 5/1995 | Patel et al. | |
| 5,526,171 A | 6/1996 | Warren | |
| 5,530,544 A | 6/1996 | Trebino et al. | |
| 5,585,913 A | 12/1996 | Hariharan et al. | |
| 5,637,966 A | 6/1997 | Umstadter et al. | |
| 5,704,700 A * | 1/1998 | Kappel et al. | 353/31 |
| 5,754,292 A | 5/1998 | Kane et al. | |
| 5,759,767 A | 6/1998 | Lakowicz | |
| 5,774,213 A | 6/1998 | Trebino et al. | |
| 5,793,091 A | 8/1998 | Devoe | |
| 5,828,459 A | 10/1998 | Silberberg | |
| 5,832,013 A | 11/1998 | Yessik et al. | |
| 5,936,732 A | 8/1999 | Smirl et al. | |
| 6,008,899 A | 12/1999 | Trebino et al. | |
| 6,042,603 A | 3/2000 | Dees et al. | |
| 6,057,919 A | 5/2000 | Machida et al. | |
| 6,072,813 A | 6/2000 | Tournois | |
| 6,081,543 A | 6/2000 | Liu et al. | |
| 6,111,251 A | 8/2000 | Hillenkamp | |
| 6,130,426 A | 10/2000 | Park et al. | |
| 6,156,527 A | 12/2000 | Schmidt et al. | |
| 6,166,385 A | 12/2000 | Webb | |
| 6,219,142 B1 | 4/2001 | Kane | |
| 6,259,104 B1 | 7/2001 | Baer | |
| 6,288,782 B1 | 9/2001 | Worster | |
| 6,296,810 B1 | 10/2001 | Ulmer | |
| 6,316,153 B1 | 11/2001 | Goodman | |
| 6,327,068 B1 * | 12/2001 | Silberberg et al. | 359/239 |
| 6,337,606 B1 | 1/2002 | Brombaugh et al. | |
| 6,344,653 B1 | 2/2002 | Webb | |
| 6,391,229 B1 | 5/2002 | Watanabe et al. | |
| 6,402,898 B1 | 6/2002 | Brumer et al. | |
| 6,421,154 B1 | 7/2002 | Diels et al. | |
| 6,480,656 B1 | 11/2002 | Islam et al. | |
| 6,498,801 B1 | 12/2002 | Dudelzak et al. | |
| 6,504,612 B2 | 1/2003 | Trebino | |
| 6,566,667 B1 | 5/2003 | Partli et al. | |
| 6,573,493 B1 | 6/2003 | Futami et al. | |
| 6,577,782 B1 | 6/2003 | Leaird et al. | |
| 6,621,613 B2 | 9/2003 | Silberberg et al. | |
| 6,678,450 B1 | 1/2004 | Franson | |
| 6,697,196 B2 | 2/2004 | Suzuki | |
| 6,723,991 B1 | 4/2004 | Sucha et al. | |
| 6,795,777 B1 | 9/2004 | Scully et al. | |
| 6,804,000 B2 | 10/2004 | Roorda et al. | |
| 6,857,744 B2 | 2/2005 | Nakada et al. | |
| 6,885,325 B2 | 4/2005 | Omelyanchouk et al. | |
| 6,915,040 B2 | 7/2005 | Willner et al. | |
| 6,930,779 B2 | 8/2005 | McGrew | |
| 6,963,591 B2 | 11/2005 | Tulloch et al. | |
| 7,170,598 B2 | 1/2007 | Walla et al. | |
| 7,439,497 B2 | 10/2008 | Dantus et al. | |
| 7,450,618 B2 | 11/2008 | Dantus | |
| 2001/0015990 A1 * | 8/2001 | Miyai | 372/23 |
| 2002/0086245 A1 | 7/2002 | Zait et al. | |
| 2003/0099264 A1 | 5/2003 | Dantus et al. | |
| 2003/0194165 A1 | 10/2003 | Silberberg et al. | |
| 2004/0128081 A1 | 7/2004 | Rabitz et al. | |
| 2004/0145735 A1 | 7/2004 | Silberberg et al. | |
| 2004/0155184 A1 | 8/2004 | Stockman et al. | |
| 2004/0240037 A1 | 12/2004 | Harter | |
| 2004/0263950 A1 | 12/2004 | Fermann et al. | |
| 2005/0036202 A1 | 2/2005 | Cohen et al. | |
| 2005/0155958 A1 | 7/2005 | Arai et al. | |
| 2005/0185188 A1 | 8/2005 | McGrew | |
| 2005/0226287 A1 | 10/2005 | Shah et al. | |
| 2006/0066848 A1 | 3/2006 | Frankel | |
| 2006/0120412 A1 | 6/2006 | Liu | |
| 2006/0274403 A1 | 12/2006 | Kaplan et al. | |

FOREIGN PATENT DOCUMENTS

| | | |
|---|---|---|
| WO | WO 99/57318 | 11/1999 |
| WO | WO 00 70647 | 11/2000 |
| WO | WO 01/54323 | 7/2001 |
| WO | WO 02 61799 | 1/2002 |

OTHER PUBLICATIONS

Hoki, K. et al., Locally Designed Pulse Shaping for Selective Preparation of Enantiomers from their Racemate, Journal of Chemical Physics, New York, NY, US, vol. 114, No. 4, Jan. 22, 2001, pp. 1575-1581.

Bychkov S. S. et al., Laser Synthesis of Chiral Molecules in Isotropic Racemic Media, Journal of Experimental and Theoretical Physics, Nauka/Interperiodica, MO, vol. 93, No. 1, Jul. 1, 2001, pp. 24-32.

Hoki, K. et al., Selective Preparation of Enantiomers from a Racemate by Laser Pulses: Model Simulation for Oriented Atropisomers with Coupled Rotations and Torsions, Chemical Physics Elsevier Netherlands, vol. 267, No. 1-3, Jun. 1, 2001, pp. 59-79.

Brixner T., et al., Quantum Control by Ultrafast Polarization Shaping, Phys Rev Lett, vol. 92, No. 20, May 21, 2004, pp. 208301-1.

Thanopulos I. et al: Laser-Driven Coherent Manipulation of Molecular Chirality, Chemical Physics Letters Elsevier Netherlands, vol. 390, No. 1-3, May 21, 2004, pp. 228-235.

Atabek, O. et al., Intense Laser Control of the Chemical Bond, Theochem Elsevier Netherlands, vol. 493, Dec. 15, 1999, pp. 89-101.

Pelfang Tian et al., Femtosecond Phase-Coherent Two-Dimensional Spectroscopy, Science American Assoc. Adv. Sci. USA, vol. 300, No. 5625, Jun. 6, 2003, pp. 1553-1555.

Motzkus, M., Open and Closed Loop Control of Complex Molecules with Shaped fs Pulses, 2003 International Conference Physics and Control. Proceedings (Cat. No. 03EX708), IEEE Piscataway, NJ, USA, vol. 3, 2003, p. 746, vol. 3.

Ma R., et al., Intense Femtosecond Laser Field-Induced Coulomb Fragmentation of $C_2H_4$, International Journal of Mass Spectrometry, Elsevier, Amsterdam, NL, vol. 242, No. 1, Mar. 15, 2005, pp. 43-48.

Wu, C. et al., Mass and Photoelectron Spectrometer for Studying Field-Induced Ionization of Molecules, International Journal of Mass Spectrometry, Elsevier Science Publishers, Amsterdam, NL, vol. 216, No. 3, May 15, 2002, pp. 249-255.

Chen J. et al., Femtosecond Laser-Induced Dissociative Ionization and Coulomb Explosion of Ethanol, International Journal of Mass Spectrometry, Elsevier, Amsterdam, NL, vol. 241, No. 1, Feb. 15, 2005, pp. 25-29.

Wu, Chengyin et al., Laser-Induced Dissociation and Explosion of Methane and Methanol, J. Phys. B. At. Mol. Opt. Phys; Journal of Physics B: Atomic, Molecular and Optical Physics, Jun. 14, 2002, vol. 35, No. 11, pp. 2575-2582.

Tomizawa H. et al., Development of Automatically Optimizing System of Both Spatial and Temporal Beam Shaping for UV-Laser Pulse, Proceedings of the SPIE—The International Society for Optical Engineering SPIE-Int. Soc. Opt. Eng USA, vol. 5481, No. 1, 2004, pp. 47-55.

Yu, Huang, et al., Application of Adaptive Feedback Loop for Ultra-Violet Femtosecond Pulse Shaper Control, Optics Express Opt. Soc. America USA, vol. 14, No. 21, Oct. 2006.

Roth, M. et al., Acousto-Optic Femtosecond Pulse Shaping in the Ultraviolet, Lasers and Electro-Optics, 2005. (Cleo). Conference in Baltimore, Md., USA, May 22-27, 2005, Piscataway, NJ, USA. IEEE, May 22, 2005, pp. 2244-2246.

Roth, M. et al., Acousto-optical Shaping of Ultraviolet Femtosecond Pulses, Applied Physics B; Lasers and Optics, Springer-Verlag, BE, vol. 80, No. 4-5, Apr. 1, 2005, pp. 441-444.

Dela Cruz, J. et al., "Use of coherent control methods through scattering biological tissue to achieve functional imaging," PNAS, vol. 101, No. 49, Dec. 7, 2004, pp. 16996-17001.

Weiner, A.M. et al. "Generation of terahertz-rate trains of femtosecond pulses by phase-only filtering," Optics Letters, vol. 15, No. 1, Jan. 1, 1990, pp. 51-53.

Dantus, Marcos and Lozovoy, Vadim, "Experimental Coherent Laser Control of Physicochemical Processes", Chemical Reviews, 2004, vol. 104, No. 4, pp. 1813-1859.

T. Baumert, et al., "Femtosecond Pulse Shaping by an Evolutionary Algorithm with Feedback", Applied Physics B 65, 779-782, (1997).

H. Zou, C. Zhou, Femtosecond Pulse Shaping with Space-to-Time Conversion Based on Planar Optics, Optik Optics, ScienceDirect, 2006/2007, pp. 5-8.

S. Zhang, X. Zhang, J. Huang, L. Deng, Z. Sun, W. Zhang, Z. Wang, Z. Xu, R.Li, Coherent Enhancement of Broadband Frequency Up-Conversion in BBO Crystal by Shaping Femtosecond Laser Pulses, Optics Communications, ScienceDirect, 2006/2007, pp. 559-563.

Y. Oishi, A. Suda, F. Kannari, K. Midorikawa, Intense Femtosecond Pulse Shaping Using a Fused-Silica Spatial Light Modulator, Optics Communications, ScienceDirect, 2006/2007, pp. 305-309.

B. Xu, Y. Coello, V.Lozovoy, D. Harris; M. Dantus, Pulse Shaping of Octave Spanning Femtosecond Laser Pulses, Optics Express, vol. 14, No. 22, Oct. 30, 2006, six pages.

F.M. Reinert, M. Ninck, W. Lüthy, T. Feurer, Shaping a Femtosecond Pulse with a Programmable Thermo-Optically Driven Phase Modulator, Optics Express, vol. 15, No. 7, Apr. 2, 2007, six pages.

H. Miao, A. Weiner, C. Langrock, R. Roussev, M. Fejer, Sensing and Compensation of Femtosecond Waveform Distortion Induced by All-Order Polarization Mode Dispersion at Selected Polarization States, Optics Letters, vol. 32, No. 4, Feb. 15, 2007, pp. 424-426.

S. Nath, D. Urbanek, S. Kern, M. Berg, High-Resolution Raman Spectra with Femtosecond Pulses: An Example of Combined Time- and Frequency-Domain Spectroscopy, Physical Review Letters, 2006, pp. 267401-1 to 267401-4.

Comstock et al.; "Multiphoton intrapulse interference 6; binary phase shaping"; Optics Express Opt. Soc.. America USA, vol. 12, No. 6, Mar. 22, 2004; pp. 1061-1066.

Hu et al.; "A New Nonlinear Optical Crystal-$BaAlBO_3F_2$(BABF)"; Japanese Journal of Applied Physics, vol. 41, No. 10B, Part 2, Oct. 15, 2002; pp. L1131-L1133.

Weiner et al.; "Shaping of femtosecond pulses using phase-only filters designed by simulated annealing"; Journal of the Optical Society of America A (Optics and Image Science) USA, vol. 10, No. 5, May 1993; pp. 1112-1120.

PCT International Search Report, dated Mar. 8, 2005.

M. Hacker et al.; "Iterative Fourier Transform Algorithm for Phase-Only Pulse Shaping", Optics Express, vol. 9, No. 4, Aug. 13, 2001, pp. 191-199.

R. Bartels et al.; "Shaped-Pulse Optimization of Coherent Emission of High-Harmonic Soft X-Rays", 2000 Macmillan Magazines Ltd., Nature, vol. 406. Jul. 13, 2000, pp. 164-166.

Dong Gun Lee et al.; "Coherent Control of High-Order Harmonics with Chirped Femtosecond Laser Pulses"; Physical Review Letters, vol. 87, No. 24, Dec. 10, 2001; pp. 243902-1-243902-4.

M. Armstrong et al.; "Versatile seven-femtosecond pulse compressor of parametrically amplified pulses using adaptive optics: studies of the primary events in protein dynamics"; Applied Physics B 74 (Suppl), 2002; pp. S127-S132.

D.S. Chemla et al; "Ultrafast phase dynamics of coherent emission from excitons in GaAs quantum wells"; Physical Review B, vol. 50, No. 12, Sep. 15, 1995; pp. 8439-8453.

Jerome Tignon et al.; "Spectral Interferometry of Semiconductor Nanostructures"; IEEE Journal of Quantum Electronics, vol. 35, No. 4; Apr. 1999; pp. 510-522.

Arthur L. Smirl et al.; "Heavy-Hole and Light-Hole Quantum Beats in the Polarization State of Coherent Emission from Quantum Wells"; IEEE Journal of Quantum Electronics, vol. 35, No. 4; Apr. 1999; pp. 523-531.

John D. Hybl et al; "Two-dimensional Fourier transform electronic spectroscopy"; Journal of Chemical Physics, vol. 115, No. 14; Oct. 8, 2001; pp. 6606-6622.

C. Iaconis et al.; "Direct measurement of the two-point field correlation function"; Optics Letters, vol. 21, No. 21; Nov. 1, 1996; pp. 1783-1785.

A.M. Weiner et al.; "Femtosecond Pulse Sequences Used for Optical Manipulation of Molecular Motion"; Reports; Mar. 16, 1990; pp. 1317-1319.

Ch. Warmuth et al.; "Studying vibrational wavepacket dynamics by measuring fluorescence interference fluctuations"; Journal of Chemical Physics, vol. 112, No. 11; Mar. 15, 2000; pp. 5060-5069.

Ch. Warmuth et al.; "Molecular quantum dynamics in a thermal system: fractional wave packet revivals probed by random-phase fluorescence interferometry"; Journal of Chemical Physics, vol. 114, No. 22; Jun. 8, 2001; pp. 9901-9910.

G.G. Paulus et al.; "Absolute-phase phenomena in photoionization with few-cycle laser pulses"; Nature, vol. 414; Nov. 8, 2001; pp. 182-184.

Yaron Silberberg; "Physics at the attosecond frontier"; Nature, vol. 414, Nov. 29, 2001; pp. 494-495.

M. Hentschel et al.; "Attosecond metrology"; Nature, vol. 414; Nov. 29, 2001; pp. 509-513.

L. Lepetit et al.; "Linear techniques of phase measurement by femtosecond spectral interferometry for applications in spectroscopy"; J. Opt. Soc. Am. B, vol. 12, No. 12; Dec. 1995; pp. 2467-2474.

L. Lepetit et al.; "Two-dimensional nonlinear optics using Fourier-transform spectral interferometry"; Optics Letters, vol. 21, No. 8; Apr. 15, 1996; pp. 564-566.

K.C. Chu et al.; "Temporal interferometric measurement of femtosecond spectral phase"; Optics Letters, vol. 21, No. 22; Nov. 15, 1996; pp. 1842-1844.

W.J. Walecki et al.; "Characterization of the polarization state of weak ultrashort coherent signals by dual-channel spectral interferometry"; Optics Letters, vol. 22, No. 2; Jan. 15, 1997; pp. 81-83.

J.P. Likforman et al.; "Measurement of photon echoes by use of femtosecond Fourier-transform Spectral Interferometry"; Optics Letters, vol. 22, No. 14; Jul. 15, 1997; pp. 1104-1106.

Michel F. Emde et al.; "Spectral interferometry as an alternative to time-domain heterodyning"; Optics Letters, vol. 22, No. 17; Sep. 1, 1997; pp. 1338-1340.

X. Chen et al.; "Temporally and spectrally resolved amplitude and phase of coherent four-wave-mixing emission from GaAs quantum wells"; Physical Review B, vol. 56, No. 15; Oct. 15, 1997; pp. 9738-9743.

Christophe Dorrer; "Influence of the calibration of the detector on spectral interferometry"; J. Opt. Soc. Am. B; vol. 16, No. 7; Jul. 1999; pp. 1160-1168.

Allison W. Albrecht et al.; "Experimental distinction between phase shifts and time delays: Implications for femtosecond spectroscopy and coherent control of chemical reactions"; Journal of Chemical Physics, vol. 111, No. 24; Dec. 22, 1999; pp. 10934-10955.

Christophe Dorrer et al.; "Spectral resolution and sampling issues in Fourier-transform spectral interferometry"; J. Opt. Soc. Am. B, vol. 17, No. 10; Oct. 2000; pp. 1795-1802.

G. Roberts; "Abstract-Interference effects in femtosecord spectroscopy"; Philosophical Transactions Of The Royal Society Of London Series A-Mathematical Physical and Engineering Sciences; 360 (1794): 987-1021; May 15, 2002 (1 page).

B. Chatel et al.; "Role of quadratic and cubic spectral phases in ladder climbing with ultrashort pulses"; Physical Review A 70; 2004; pp. 053414-1-053414-10.

Richard S. Judson et al.; "Teaching Lasers to Control Molecules"; Physical Review Letters, vol. 68, No. 10; Mar. 9, 1992; pp. 1500-1503.

Michael Messina et al.; "Quantum control of multidimensional systems: Implementation within the time-dependent Hartree approximation"; J. Chem Phys. 104; Jan. 1996; pp. 173-182.

D.H. Schirrmeister et al; "Femtosecond pulse dependence of dissipation in molecular systems"; Chemical Physics Letters Dec. 4, 1998; pp. 383-390.

Herschel Rabitz et al.; "Optimal Control of Molecular Motion: Design, Implementation and Inversion"; Acc. Chem. Res., vol. 33, No. 8; 2000; pp. 572-578.

R. deVivie-Riedle et al.; "Design and interpretation of laser pulses for the control of quantum systems"; Applied Physics B; 2000; pp. 285-292.

Moshe Shapiro et al.; On the Origin of Pulse Shaping Control of Molecular Dynamics; J. Phys. Chem. A, vol. 105, No. 105; 2001; pp. 2897-2902.

Y.J. Yan et al.; "Pulse shaping and coherent Raman spectroscopy in condensed phases"; J. Chem. Phys 94 (2); Jan. 15, 1991; pp. 997-1001.

Bern Kohler et al.; "Mode-Locking Matter with Light"; J. Phys. Chem 1993, 97; pp. 12602-12608.

Jeffrey L. Krause et al.; "Optical control of molecular dynamics: Molecular cannons, reflectrons and wave-packet focusers"; J. Chem. Phys. 99(9); Nov. 1, 1993; pp. 6562-6578.

V. Engel et al; "Two-photon wave-packet interferometry"; J. Chem Phys. 100 (8); Apr. 15, 1994; pp. 5448-5458.

Jeffrey L. Krause et al.; "Quantum Control of Molecular Dynamics: The Strong Response Regime"; J. Phys. Chem; 1995, 99; pp. 13736-13747.

Jianwei Che et al.; "Detection and Control of Molecular Quantum Dynamics"; J. Phys. Chem.; 1995; pp. 14949-14958.

M. Sterling et al.; "Interrogation and control of condensed phase chemical dynamics with linearly chirped pulses: 12 in solid Kr"; J. Chem. Phys. 104; May 1, 1996; pp. 6497-6506.

Jianwei Che et al.; "Semiclassical Dynamics and Quantum Control in Condensed Phases: Application to 12 in a Solid Argon Matrix"; J. Phys. Chem. 1996, 100; pp. 7873-7883.

Jianshu Cao et al.; "A simple physical picture for quantum control of wave packet localization"; J. Chem. Phys., 107; Aug. 1, 1997; pp. 1441-1450.

Kenji Mishima et al.; "A theoretical study on laser control of a molecular nonadiabatic process by ultrashort chirped laser pulses"; Journal of Chemical Physics, vol. 109., No. 5; Aug. 1, 1998; pp. 1801-1809.

H.A. Kim et al.; "Expanded concept of the adiabatic population transfer using dressed states"; Physical Review A, vol. 59, No. 2; Feb. 1999; pp. 1404-1407.

Jianshu Cao et al.; "Molecular pie pulses: Population inversion with positively chirped short pulses"; Journal of Chemical Physics, vol. 113, No. 5; Aug. 1, 2000; pp. 1898-1909.

A.J. Wurzer et al.; "Highly localized vibronic wavepackets in large reactive molecules"; Applied Phys. B 71, 2000; pp. 405-409.

F. Legare et al.; "Laser pulse control of Raman processes by chirped non-adiabatic passage"; Journal of Raman Spectroscopy; 2000; pp. 15-23.

Moshe Shapiro et al.; "Coherently Controlled Asymmetric Synthesis with Achiral Light"; Physical Review Letters, vol. 84, No. 8; Feb. 21, 2000; pp. 1669-1672.

Gabriel Turinici et al.; "Quantum wavefunction controllability"; Chemical Physics 267; 2001; pp. 1-9.

M. Gruebele; "Fully quantum coherent control"; Chemical Physics 267; 2001; pp. 33-46.

V.S. Malinovsky et al.; "General theory of population transfer by adiabatic rapid passage with intense, chirped laser pulses"; The European Physical Journal D 14; 2001; pp. 147-155.

Z.W. Shen et al.; "Selective preparation of ground state wave-packets: a theoretical analysis of femtosecond pump-dump-probe experiments on the potassium dimmer"; The European Physical Journal D 14; 2001; pp. 167-172.

Sanislav S. Bychkov et al.; "Laser coherent control of molecular chiral states via entanglement of the rotational and torsional degrees of freedom"; Journal of Raman Spectroscopy; 2002; pp. 962-973.

S.E. Harris; "Control of Feshbach resonances by quantum interference"; Physical Review A66; 2002; pp. 010701-1-010701-4.

John M. Jean et al.; "Application of a multilevel Redfield theory to electron transfer in condensed phases"; J. Chem. Phys. 96; Apr. 15, 1992; pp. 5827-5842.

Bjarne Amstrup et al.; "Control of HOD photodissociation dynamics via bond-selective infrared multiphoton excitation and a femtosecond ultraviolet laser pulse"; J. Chem. Phys., vol. 97, No. 11; Dec. 1, 1992; pp. 8285-8295.

L.D. Ziegler et al.; "Nonlinear polarization description of phase-locked pulse-pair spectroscopy"; J. Chem. Phys., vol. 97, No. 7; Oct. 1, 1992; pp. 4704-4713.

S. Meyer et al.; "Photoelectron distributions from femtosecond pump/probe excitation with chirped probe pulses"; Journal of Chemical Physics, vol. 108, No. 18; pp. 7631-7636.

V.M. Akulin et al.; "Laser Control of Atomic Motion inside Diatomic Molecules"; J. Phys. Chem. A, vol. 102, No. 23; 1998; pp. 4310-4320.

Jianshu Cao et al.; "Molecular Pi Pulse for Total Inversion of Electronic State Population"; Physical Review Letters, vol. 80, No. 7; Feb. 16, 1998; pp. 1406-1409.

Moshe Shapiro et al.; "Nonadiabatic wave packet dynamics: Experiment and theory in IBr"; Journal of Chemical Physics, vol. 110, No. 5; Feb. 1, 1999; pp. 2465-2473.

Zhenwen Shen et al.; "Pump-dump control and the related transient absorption spectroscopies"; Journal of Chemical Physics, vol. 110, No. 15; Apr. 15, 1999; pp. 7192-7201.

Kenji Mishima et al.; "Theoretical study on quantum control of photodissociation and photodesorption dynamics by femtosecond chirped laser pulses"; Journal of Chemical Physics, vol. 110, No. 16; Apr. 22, 1999; pp. 7756-7769.

H.S. Moon et al.; "Coherence control using the ratio of Rabi frequencies for complete coherent inversion in a four-level system"; J. Phys. B At. Mol. Phys. vol. 32; 1999; pp. 987-999.

Jeffrey A. Cina; "Nonlinear wavepacket interferometry for polyatomic molecules"; Journal of Chemical Physics, vol. 113, No. 21; Dec. 1, 2000; pp. 9488-9496.

F. Gelmukhanov et al.; "Dynamics of two-photon absorption by molecules and solutions"; J. Opt. Soc. Am. B, vol. 19, No. 5, May 2002; pp. 937-945.

Philip H. Bucksbaum; "Ultrafast control"; Nature magazine, vol. 421; Feb. 6, 2003; pp. 593-594. Kuhn & Weyn SR2 Sep. 4, 2001.

Christopher J. Bardeen et al.; "Effec of Pulse Shape on the Efficiency of Multiphoton Processes: Implications for Biological Microscopy"; Journal of Biomedical Optics, vol. 4, No. 3; Jul. 1999; pp. 362-367.

T. Hornung et al.; "Optimal control of one- and two-photon transitions with shaped femtosecond pulses and feedback"; Applied Physics B 71; 2000; pp. 277-284.

T. Brixner et al.; "Photoselective adaptive femtosecond quantum control in the liquid phase"; Nature magazine, vol. 414; Nov. 2001; pp. 57-60.

B.J. Pearson et al.; "Coherent control using adaptive learning algorithms"; Physical Review A, vol. 63; 2001; pp. 063412-1-063412-12.

Jennifer L. Herek et al.; "Quantum control of energy flow in light harvesting"; Nature magazine, vol. 417; May 30, 2002; pp. 533-535.

Nirit Dudovich et al.; "Single-pulse coherently controlled nonlinear Raman spectroscopy and microscopy"; Nature magazine, vol. 418; Aug. 1, 2002; pp. 512-514.

Dan Oron et al.; "Single-Pulse Phase-Contrast Nonlinear Raman Spectroscopy"; Physical Review Letters, vol. 89, No. 27; Dec. 30, 2002; pp. 27300-1-273001-4.

T. Brixner et al.; "Liquid-phase adaptive femtosecond quantum control: Removing intrinsic intensity dependencies"; Journal of Chemical Physics, vol. 118, No. 8; Feb. 22, 2003; pp. 3692-3701.

R. Netz et al.; "Observation of Selectivity of Coherent Population Transfer Induced by Optical Interference"; Physical Review Letters, vol. 90, No. 6; Feb. 14, 2003; pp. 063001-1-063001-4.

D.W. Schumacher et al.; "Phase Dependence of Intense Field Ionization"; Physical Review A, vol. 54, No. 5; Nov. 1996; pp. 4271-4278.

Christopher J. Bardeen et al.; "Feedback quantum control of molecular electronic population transfer"; Chemical Physics Letters 280; 1997; pp. 151-158.

Christopher J. Bardeen et al.; "Quantum Control of Population Transfer in Green Fluorescent Protein by Using Chirped Femtosecond Pulses"; J. Am. Chem. Soc., vol. 120, No. 50; 1998; 13023-13027.

Doron Meshulach et al.; "Coherent quantum control of two-photon transitions by a femtosecond laser pulse"; Nature magazine, vol. 396; Nov. 19, 1998; pp. 239-242.

A. Baltuska et al.; "Attosecond control of electronic processes by intense light fields"; Nature magazine, vol. 421; Feb. 6, 2003; pp. 611-615.

D.J. Maas et al.; "Population transfer via adiabatic passage in the rubidium quantum ladder system"; Physical Review A, vol. 59, No. 2; Feb. 1999; pp. 1374-1381.

Zohar Amitay et al.; "Phase-tailoring molecular wave packets to time shift their dynamics"; Chemical Physics 267; 2001; pp. 141-149.

T.C. Weinacht et al.; "Coherent learning control of vibrational motion in room temperature molecular gases"; Chemical Physics Letters 344; 2001; pp. 333-338.

R. van Leeuwen et al.; "Manipulation of differential electron yields via autoionizing wave-packet control"; Physical Review A, vol. 63; 2001; pp. 033403-1-033403-5.

Dan Oron et al.; "Quantum control of coherent anti-Stokes Raman processes"; Physical Review A, vol. 65; 2002; pp. 043408-1-043408-4.

Nirit Dudovich et al.; "Coherent Transient Enhancement of Optically Induced Resonant Transitions"; Physical Review Letters, vol. 88, No. 12; Mar. 25, 2002; pp. 123004-1-123004-4.

Jerome Degert et al.; "Realization of a Time-Domain Fresnel Lens with Coherent Control"; Physical Review Letters, vol. 89, No. 20; Nov. 11, 2002; pp. 203003-1-203003-4.

M. Wollenhaupt et al.; "Interferences of Ultrashort Free Electron Wave Packets"; Physical Review Letters, vol. 89, No. 17; Oct. 21, 2002; pp. 173001-1-173001-4.

R. Teets et al.; "Coherent Two-Photon Excitation by Multiple Light Pulses"; Physical Review Letters, vol. 38, No. 14; Apr. 4, 1977; lags. 760-764.

R.R. Jones; "Multiphoton Ionization Enhancement Using Two Phase-Coherent Laser Pulses"; Physical Review Letters, vol. 75, No. 8; Aug. 21, 1995; pp. 1491-1494.

D.J. Maas et al.; "Vibrational ladder climbing in NO by ultrashort infrared laser pulses"; Chemical Physics Letters 270; May 16, 1997; pp. 45-49.

Christopher J. Bardeen et al.; "Quantum control of I2 in the gas phase and in condensed phase solid Kr matrix"; J. Chem. Phys., vol. 106, No. 20; May 22, 1997; pp. 8486-8503.

D.J. Maas et al.; Vibrational ladder climbing in NO by (sub)picosecond frequency-chirped infrared laser pulses; Chemical Physics Letters 290; 1998; pp. 75-80.

Vladislav V. Yakovlev et al.; "Chirped pulse enhancement of multiphoton absorption in molecular iodine"; Journal of Chemical Physics, vol. 108, No. 6, Feb. 8, 1998; pp. 2309-2313.

Radoslaw Uberna et al.; "Phase and amplitude control in the formation and detection of rotational wave packets in the E1Eg state of Li2"; Journal of Chemical Physics, vol. 108, No. 22; pp. 9259-9274.

John M. Papanikolas et al.; "Erratum: Manipulation of rovibrational wave packet composition in the Li2 E(Eg) shelf state using intermediate state selection and shaped femtosecond laser pulses"; J. Chem Phys. 107, 4172; 1997; p. 10830.

T.C. Weinacht et al.; "Measurement of the Amplitude and Phase of a Sculpted Rydberg Wave Packet"; Physical Review Letters; vol. 80, No. 25; Jun. 22, 1998; pp. 5508-5511.

Radoslaw Uberna et al.; "Phase control of wavepacket dynamic using shape femtosecond pulses"; Faraday Discuss, vol. 113; 1999; pp. 385-400.

T.C. Weinacht et al.; "Toward Strong Field Mode-Selective Chemistry"; J. Phys. Chem. A, vol. 103, No. 49; 1999; pp. 10166-10168.

Mohamed Aziz Bouchene et al.; "Wavepacket interferometry with chirped pulses"; J. Phys. B At. Mol. Opt. Phys. 32; 1999; pp. 5167-5177.

D.J. Maas et al.; "Rotational interference in vibrational ladder climbing in NO by chirped infrared laser pulses"; Physical Review A, vol. 60, No. 2; Aug. 1999; pp. 1351-1362.

R. van Leeuwen et al.; "Coherent Control of the Energy and Angular Distribution of Autoionized Electrons"; Physical Review Letters, vol. 82, No. 14; Apr. 5, 1999; pp. 2852-2855.

Celine Nicole et al.; "Saturation of wave-packet interferences: Direct observation of spin precession in potassium atoms"; Physical Review A, vol. 60, No. 3; Sep. 1999; pp. R1755-R1758.

Mohamed Aziz Bouchene et al.; "Interplay between wave packet interferences and second harmonic generation"; Optics Communications 181; 2000; pp. 327-336.

Radoslaw Uberna et al.; "Ultrafast spectroscopy of wavelength-dependent coherent photoionization cross sections of Li2 wave packets in the E1Eg state: The role of Rydberg states"; Journal of Chemical Physics, vol. 114, No. 23; Jun. 15, 2001; pp. 10311-10320.

Lorenzo Pesce et al.; "Quantum dynamics simulation of the ultrafast photoionization of Li2"; Journal of Chemical Physics, vol. 114, No. 3; Jan. 15, 2001; pp. 1259-1271.

M.F. DeCamp et al.; "Dynamics and coherent control of high-amplitude optical phonons in bismuth"; Physical Review B, vol. 64; 2001; pp. 092301-1-092301-3.

J. Ahn et al.; "Quantum Phase Retrieval of a Rydberg Wave Packet Using a Half-Cycle Pulse"; Physical Review Letters, vol. 86, No. 7; Feb. 12, 2001; pp. 1179-1182.

Sebastien Zamith et al.; "Observation of Coherent Transients in Ultrashort Chirped Excitation of an Undamped Two-Level System"; Physical Review Letters, vol. 87, No. 3; Jul. 16, 2001; pp. 033001-1-033001-4.

Hans U. Stauffer et al.; "Simultaneous phase control of Li2 wave packets in two electronic states"; Journal of Chemical Physics, vol. 116, No. 3; Jan. 15, 2002; pp. 946-954.

Joshua B. Ballard et al.; "Optimization of wave packet coefficients in Li 2 using an evolutionary algorithm: The role of resonant and nonresonant wavelengths"; Journal of Chemical Physics, vol. 116, No. 4; Jan. 22, 2002; pp. 1350-1360.

Elizabeth Mirowski et al.; "Effect of nonresonant frequencies on the enhancement of quantum beat amplitudes in rovibrational states of Li2: The role of state spacing"; Journal of Chemical Physics, vol. 117, No. 24; Dec. 22, 2002; pp. 11228-11238.

S.N. Pisharody et al.; "Phase-controlled stair-step decay of autoionizing radial wave packets"; Physical Review A, vol. 65; 2002; pp. 033418-1-033418-10.

R. Netz et al.; "Coherent population dynamics of a three-level atom in spacetime"; Physical Review A, vol. 65; pp. 043406-1-043406-12.

Joshua B. Ballard et al.; "Simultaneous control of time-dependent population transfer dynamics and wave-packet quantum interferences in Li2 by shaped ultrafast pulses"; Physical Review A 66; 2002; pp. 043402-1-043402-7.

Dan Oron et al.; "Narrow-Band Coherent Anti-Stokes Raman Signals from Broad-Band Pulses"; Physical Review Letters, vol. 88, No. 6; Feb. 11, 2002; pp. 063004-1-063004-4.

M.M. Salour et al.; "Observation of Ramsey's Interference Fringes in the Profile of Doppler-Free Two-Photon Resonances"; Physical Review Letters, vol. 38, No. 14; Apr. 4, 1977; pp. 757-760.

N.F. Scherer et al.; "Time resolved dynamics of isolated molecular systems studied with phase-locked femtosecond pulse pairs"; J. Chem Phys. vol. 93, No. 1; Jul. 1, 1990; pp. 856-857.

J.S. Melinger et al.; "Adiabatic population inversion in I2 vapor with picosecond laser pulses"; J. Chem Phys. vol. 95, No. 3; Aug. 1, 1991; pp. 2210-2213.

J.J. Gerdy et al.; "Femtosecond selective control of wave packet population"; Chemical Physics Letters, vol. 171, No. 1/2; Jul. 27, 1990; pp. 1-4.

Norbert F. Scherer et al.; "Fluorescence-detected wave packet interferometry: Time resolved molecular spectroscopy with sequences of femtosecond phase-locked pulses"; J. Chem. Phys., vol. 95, No. 3; Aug. 1, 1991; pp. 1487-1511.

N.F. Scherer et al.; "Fluorescence-detected wave packet interferometry. II. Role of rotations and determination of the susceptibility"; J. Chem. Phys., vol. 96, No. 6; Mar. 15, 1992; pp. 4180-4194.

L.D. Noordam et al.; "Redistribution of Rydberg States by Intense Picosecond Pulses"; Physical Review Letters, vol. 68, No. 10; Mar. 9, 1992; pp. 1496-1499.

J.S. Melinger et al.; "Generation of Narrowband Inversion with Broadband Laser Pulses"; vol. 68, No. 13; Mar. 30, 1992; pp. 2000-2003.

B. Broers et al.; "Efficient Population Transfer in a Three-Level Ladder System by Frequency-Swept Ultrashort Laser Pulses"; Physical Review Letters, vol. 69, No. 14; Oct. 5, 1992; pp. 2062-2065.

R.R. Jones et al.; "Ramsey Interference in Strongly Driven Rydberg Systems"; Physical Review Letters, vol. 71, No. 16; Oct. 18, 1993; pp. 2575-2578.

J.F. Christian et al.; "Rubidium electronic wavepackets probed by a phase-sensitive pump-probe technique"; Optics Communications, vol. 103, No. 1/2; Nov. 1, 1993; pp. 79-84.

J.S. Melinger et al.; "Adiabatic population transfer with frequency-swept laser pulses"; J. Chem. Phys. vol. 101, No. 8; Oct. 15, 1994; pp. 6439-6454.

P. Balling et al.; "Interference in climbing a quantum ladder system with frequency-chirped laser pulses"; Physical Review A, vol. 50, No. 5; Nov. 1994; pp. 4276-4285.

D.W. Schumacher et al.; "Phase Dependence of Intense Field Ionization: A Study Using Two Colors"; Physical Review Letters, vol. 73, No. 10; Sep. 5, 1994; pp. 1344-1347.

L. Marmet et al.; "Observation of Quasi-Landau Wave Packets"; Physical Review Letters, vol. 72, No. 24; Jun. 13, 1994; pp. 3779-3782.

Valerie Blanchet et al.; "One-color coherent control in Cs2 Observation of 2.7 fs beats in the ionization signal"; Chemical Physics Letters, vol. 233; Feb. 25, 1995; pp. 491-499.

R.R. Jones et al.; "Bound-state interferometry using incoherent light"; J. Phys. B 28 At. Mol. Opt. Phys.; 1995; pp. L405-L411.

D.W. Schumacher et al.; "Programmable cesium Rydberg wave packets"; Physical Review A, vol. 52, No. 6; Dec. 1995; pp. 4719-4726.

R.R. Jones; "Interference Effects in the Multiphoton Ionization of Sodium"; Physical Review Letters, vol. 74, No. 7; Feb. 13, 1995; pp. 1091-1094.

Bern Kohler et al.; "Quantum Control of Wave Packet Evolution with Tailored Femtosecond Pulses"; Physical Review Letters, vol. 74, No. 17; Apr. 24, 1995; pp. 3360-3363.

M. Ovchinnikov et al.; "Quantum interference in resonant Raman spectra of I2 in condensed media"; J. Chem. Phys., vol. 106, No. 13; Apr. 1, 1997; pp. 5775-5778.

Richard M. Williams et al.; "Compositional control of rovibrational wave packets in the E(1Eg) "shelf" state of Li2 via quantum-state-resolved intermediate state selection"; J. Chem. Phys. vol. 106, No. 20; May 22, 1997; pp. 8310-8323.

John M. Papanikolas et al.; "Manipulation of rovibrational wave packet composition in the Li2 E(1Eg) shelf state using intermediate state selection and shaped femtosecond laser pulses"; J. Chem. Phys., vol. 107, No. 11; Sep. 15, 1997; pp. 4172-4178.

Valerie Blanchet et al.; "Temporal Coherent Control in Two-Photon Transitions: From Optical Interferences to Quantum Interferences"; Physical Review Letters, vol. 78, No. 14; Apr. 7, 1997; pp. 2716-2719.

R. Zadoyan et al.; "Wavepacket diagnosis with chirped probe pulses"; Chemical Physics, vol. 233; 1998; pp. 353-363.

M.A. Bouchene et al.; "Temporal coherent control induced by wave packet interferences in one and two photon atomic transitions"; The European Physical Journal D, vol. 2; 1998; pp. 131-141.

Valerie Blanchet et al.; "Temporal coherent control in the photoionization of Cs2: Theory and experiment"; Journal of Chemical Physics, vol. 108, No. 12; Mar. 22, 1998; pp. 4862-4876.

R.A. Bartels et al.; "Nonresonant Control of Multimode Molecular Wave Packets at Room Temperature"; Physical Review Letters, vol. 88, No. 3; Jan. 21, 2002; pp. 033001-1 through 033001-4.

T. Brixner et al.; "Abstract- Femtosecond quantum control"; Advances In Atomic, Molecular, And Optical Physics, vol. 46; 46:1-54; 2001 (1 page).

T. Brixner et al.; "Abstract-Photoselective adaptive femtosecond quantum control in the liquid phase"; Nature; 414 (6859): 57-60; Nov. 1, 2001 (1 page).

B. Dayan et al.; "Coherent control with broadband squeezed vacuum"; arXiv:quant-ph/0302038 v1; Feb. 5, 2003 (4 pages).

B. Dayan et al.; "Two Photon Absorption and Coherent Control with Broadband Down-Converted Light"; Physical Review Letters, vol. 93, No. 2; Jul. 9, 2004; pp. 023005-1-023005-4.

B. Dayan et al.; "Nonlinear Interactions with an Ultrahigh Flux of Broadband Entangled Photons"; Physical Review Letters, PRL 94; Feb. 4, 2005, 2004; pp. 043602-1-043602-4.

N. Dudovich et al.; "Single-pulse coherent anti-Stokes Raman spectroscopy in the fingerprint spectral region"; J. of Chem. Phys., vol. 118, No. 20; May 22, 2003; pp. 9208-9215.

D. Oron et al.,; "Femtosecond Phase-and-Polaration Control for Background-Free Coherent Anti-Stokes Raman Spectroscopy"; Physical Review Letters, vol. 90, No. 91; May 30, 2003; pp. 213902-1-213902-4.

N. Dudovich et al.; "Quantum Control of the Angular Momentum Distribution in Multiphoton Absorption Processes"; Physical Review Letters, vol. 93, No. 10; Mar. 12, 2004; pp. 103003-1-103003-4.

D. Oron et al.,; "All-optical processing in coherent nonlinear spectroscopy"; Physical Review A 70; 2004; pp. 023415-1-023415-4.

J.G. Underwood et al.,; "Switched Wave Packets: A Route to Nonperturbative Quantum Control"; Physical Review Letters, vol. 90, No. 22; Jun. 6, 2003; pp. 223001-1-223001-4.

M. Renard et al.; "Controlling ground-state rotational dynamics of molecules by shaped femtosecond laser pulses"; Physical Review A 69; 2004; 043401-1-043401-6.

A. Powe et al.; "Molecular Fluorescence, Phosphorescence, and Chemiluminescence Spectrometry"; Anal. Chem., vol. 76, No. 15; Aug. 15, 2004; pp. 4614-4634.

D. Abramavicius et al.; "Disentangling multidimensional femtosecond spectra of excitons by pulse shaping with coherent control"; J. of Chem. Phys., vol. 120, No. 18; May 8, 2004; pp. 8373-8378.

M.C. Chen et al.; "Coherent control multiphoton processes in semiconductor saturable Bragg reflector with freezing phase algorithm"; Appl. Phys. B 80; 2005; pp. 333-340.

W. Wohlleben et al.; "Coherent Control for Spectroscopy and Manipulation of Biological Dynamics"; Chem. Phys. Chem., 6; 2005; pp. 850-857.

T. Okada et al.; "Optical control of two-photon excitation efficiency of α-perylene crystal by pulse shaping"; Amer. Inst. of Phys., vol. 121, No. 13; Oct. 1, 2004; pp. 6386-6391.

V. Prokhorenko et al.; "Coherent control of the population transfer in complex sovated molecules at weak excitation. An experimental study"; The J. of Chem. Phys., 122; 2005; 184502-1-184502-11.

A. Prakelt et al.; "Phase control of two-photon transition with shaped femtosecond laser-pulse sequences"; Physical Review A 70; 2004; pp. 063407-1-06407-10.

B.J. Pearson et al.; "Control of Raman Lasing in the Nonimpulsive Regime"; Physical Review Letters, vol. 92, No. 24; Jun. 18, 2004; pp. 243003-1-243003-4.

Derryck T. Reid; "Algorithm for Complete and Rapid Retrieval of Ultrashort Pulse Amplitude and Phase from a Sonogram"; IEEE Journal of Quantum Electronics; vol. 35, No. 11, Nov. 1999; pp. 1584-1589.

I.G. Cormack et al.; "Rapid measurement of ultrashort-pulse amplitude and phase from a two-photon absorption sonogram trace"; J. Opt. Soc. Am. B; vol. 18, No. 9, Sep. 2001; pp. 1377-1382.

E. Tokunaga et al.; "Frequency-domain interferometer for femtosecond time-resolved phase spectroscopy"; Optics Letters, vol. 17, No. 16; Aug. 15, 1992, pp. 1131-1133.

Victor Wong et al.; "Analysis of ultrashort pulse-shape measurement using linear interferometers"; Optics Letters, vol. 19, No. 4; Feb. 15, 1994; pp. 287-289.

Victor Wong et al.; "Linear filter analysis of methods for ultrashort-pulse-shape measurements"; J. Opt.Soc. Am. B, vol. 12, No. 8; Aug. 1995; pp. 1491-1499.

David M. Jonas et al.; "Femtosecond Wavepacket Spectroscopy: Influence of Temperature, Wavelength and Pulse Duration"; J. Phys. Chem.; 1995; pp. 2594-2608.

J. Peatross et al.; "Temporal decorrelation of short laser pulses"; J. Opt. Soc. Am. B, vol. 15, No. 1; Jan. 1998; pp. 216-222.

McGraw-Hill Encyclopedia Of Science & Technology, 6th Ed.; "Mass spectrometry"; 1987; pp. 492-502 (12 pages).

Ocean Optics Inc.; "HR4000 High-resolution Spectrometer" http://oceanoptics.com/products/hr4000.asp; Jun. 25, 2005 (p. 1 of 4-p. 4 of 4).

Ocean Optics Inc.; "USB2000 Miniature Fiber Optic Spectrometer" http://oceanoptics.com/products/usb2000.asp; Jun. 25, 2005 (p. 1 of 7-p. 6 of 7).

Ocean Optics Inc.; "S2000 Miniature Fiber Optic Spectrometer" http://oceanoptics.com/products/s2000.asp; Jun. 25, 2005 (p. 1 of 4-p. 4 of 4).

M. Schurenberg et al.; "Abstract-Laser desorption/ionization mass spectrometry of peptides and proteins with particle suspension matrixes"; Analytical Chemistry; 71(1): 221-229; Jan. 1, 1999 (1 page).

F. Hillenkamp et al.;"Abstract-Matrix-assisted laser desorption/ionisation, an experience"; International Journal Of Mass Spectrometry; 200 (1-3): 71-77; Dec. 25, 2000 (1 page).

M.O. Scully, et al.; "Fast Cars: Engineering a laser spectroscopic technique for rapid identification of bacterial spores"; PNAS; vol. 99, No. 17; Aug. 20, 2002; pp. 10994-11001.

K.D. Belfield et al.; "Multiphoton-absorbing organic materials for microfabrication, emerging optical applications and non-destructive three-dimensional imaging"; J. of Phys. Organic Chem., 13; 2000; pp. 837-849.

B. Natarajan et al.; "Abstract-Innovative pulse shaping for high-performance wireless TDMA"; IEEE Communications Letters; 5 (9): 372-374; Sep. 2001 (1 page).

A. Pe're et al.; Optical Code-Division Multiple Access Using Broad-Band Parametrically Generated Light; J. of Lightwave Tech.; vol. 22, No. 6; Jun. 2004; pp. 1463-1471.

J.J. Garcia-Ripoll et al.; "Speed Optimized Two-Qubit Gates with Laser Coherent Control Techniques for Ion Trap Quantum Computing"; Physical Review Letters, vol. 91, No. 15; Oct. 10, 2003; pp. 157901-1-157901-4.

J. Ahn et al.; "Information Storage and Retrieval Through Quantum Phase"; Science Magazine, vol. 287; Jan. 21, 2000; pp. 463-465.

Greg Taft et al.; "Measurement of 10-fs Laser Pulses"; IEEE Journal of Selected Topics in Quantum Electronics, vol. 2, No. 3, Sep. 1996; pp. 575-585.

Daniel J. Kane et al.; "Simultaneous measurement of two ultrashort laser pulses from a single spectrogram in a single shot"; Optical Society of America; vol. 14, No. 4, Apr. 1997; pp. 935-943.

Peter J. Delfyett et al.; "Joint Time-Frequency Meaurements of Mode-Locked Semiconductor Diode Lasers and Dynamics Using Frequency-Resolved Optical Gating"; IEEE Journal of Quantum Electronics, vol. 35, No. 4, Apr. 1999; pp. 487-500.

David N. Fittinghoff et al.; "Frequency-Resolved Optical Gating Measurement of Ultrashort Pulses Passing Through a High Numerical Aperture Objective"; IEEE Journal of Quantum Electronics, vol. 35, No. 4, Apr. 1999; pp. 479-486.

Andrius Baltuska et al.; "Second-Harmonic Generation Frequency-Resolved Optical Gating in the Single-Cycle Regime"; IEEE Journal of Quantum Electronics, vol. 35, No. 4, Apr. 1999; pp. 459-478.

Hilary K. Eaton et al.; "Investigating Nonlinear Femtosecond Pulse Propagation with Frequency-Resolved Optical Gating"; IEEE Journal of Quantum Electronics, vol. 35, No. 4, Apr. 1999; pp. 451-458.

Craig W. Siders et al.; "Multipulse Interferometric Frequency-Resolved Optical Gating"; IEEE Journal of Quantum Electronics, vol. 35, No. 4, Apr. 1999; pp. 432-440.

Atsushi Yabushita et al.; "SHG FROG and XFROG methods for phase/intensity characterization of pulses propagated through an absorptive optical medium"; Optics Communications; Oct. 15, 2001; pp. 227-232.

Roger G.M.P. Koumans et al.; "Time-Resolved Optical Gating Based on Dispersive Propagation: A New Method to Characterize Optical Pulses"; IEEE Journal of Quantum Electronics, vol. 36, No. 2, Feb. 2000; pp. 137-144.

Daniel J. Kane et al.; "Convergence test for inversion of frequency-resolved optical gating spectrograms"; Optics Letters, vol. 25, No. 16, Aug. 15, 2000; pp. 1216-1218.

Julie A. Gruetzmacher et al.; "Time and Frequency-Gated FID: a New Approach to Study the Vibrational Dephasing of Water"; Ultrafast Phenomena XII, 66; pp. 530-532.

Juan L.A. Chilla et al.; "Analysis of a Method of Phase Measurement of Ultrashort Pulses in the Frequency Domain"; IEEE Journal of Quantum Electronics, vol. 27, No. 5, May 1991; pp. 1228-1235.

David N. Fittinghoff et al.; "Noise sensitivity in frequency-resolved optical-gating measurements of ultrashort pulses"; J. Opt. Soc. Am. B, vol. 12, No. 10, Oct. 1995; pp. 1955-1967.

Noriaki Tsurumachi et al.; "Interferometric observation of femtosecond free induction decay"; Optics Letters, vol. 19, No. 22, Nov. 15, 1994; pp. 1867-1869.

C. Dorrer et al.; "Characterization of chirped-pulse amplification systems with spectral phase interferometry for direct electric-field reconstruction"; Applied Physics B 70 (Suppl.), 2000; pp. S77-S84.

C. Radzewicz et al.; "A poor man's FROG"; Optics Communications, Dec. 15, 2000; pp. 329-333.

C. Dorrer et al.; "Spatio-temporal characterization of the electric field of ultrashort optical pulses using two-dimensional shearing interferometry"; Applied Physics B74 (Suppl.), 2002; pp. S209-S217.

K.H. Hong et al.; "Time-frequency analysis of chirped femtosecond pulses using Wigner distribution function"; Applied Physics B74 (Suppl), 2002; pp. S231-S236.

Christophe Dorrer et al.; "Accuracy criterion for ultrashort pulse characterization techniques: application to spectral phase interferometry for direct electric field reconstruction"; Appl. Phys. B 74, vol. 19, No. 5, May 2002; pp. 1019-1029.

Kazunori Naganuma et al; "General Method for Ultrashort Light Pulse Chirp Measurement"; IEEE Journal of Quantum Electronics, vol. 25, No. 5; Jun. 1989; pp. 1225-1233.

Y. Ding et al.; "Time-Domain Image Processing Using Dynamic Holography"; IEEE Journal of Selected Topics in Quantum Electronics, vol. 4, No. 2; Mar./Apr. 1998; pp. 332-341.

Chris Iaconis et al; "Self-Referencing Spectral Interferometry for Measuring Ultrashort Optical Pulses"; IEEE Journal of Quantum Electronics, vol. 35, No. 4; Apr. 1999; pp. 501-509.

Jung-Ho Chung et al.; "Ambiguity of Ultrashort Pulse Shapes Retrieved From the Intensity Autocorrelation and the Power Spectrum"; IEEE Journal on Selected Topics of Quantum Electronics, vol. 7, No. 4; Jul./Aug. 2001; pp. 656-666.

V. Kabelka et al.; "Time-frequency imaging of a single ultrashort light pulse from anularly resolved autocorrelation"; Optics Letters, vol. 20, No. 1; Jun. 1, 1995; pp. 1301-1303.

Paul R. Bolton et al.; "Propagation of intense, ultrashort laser pulses through metal vapor: refraction-limited behavior for single pulses"; J. Opt. Soc. Am. B, vol. 13, No. 2; Feb. 1996; pp. 336-346.

June-Koo Rhee et al.; "Real-time dispersion analyzer of femtosecond laser pulses with use of a spectrally and temporally resolved upconversion technique"; J. Opt. Soc. Am. B, vol. 13, No. 8; Aug. 1996; pp. 1780-1785.

Marco A. Krumbugel et al.; "Direct ultrashort-pulse intensity and phase retrieval by frequency-resolved optical gating and a computational neural network"; Optics Letters, vol. 21, No. 2; Jan. 15, 1996; pp. 143-145.

David N. Fittinghoff et al.; "Measurement of the intensity and phase of ultraweak, ultrashort laser pulses"; Optics Letters, vol. 21, No. 12; Jun. 15, 1996; pp. 884-886.

T. Feurer et al.; "Measuring the temporal intensity of ultrashort laser pulses by triple correlation"; Appl. Phys. B; 1998; pp. 163-168.

Alfred Kwok et al.; "Frequency-Resolved Optical Gating Using Cascaded Second-Order Nonlinearities"; Journal of Selected Topics in Quantum Electronics, vol. 4, No. 2; Mar./Apr. 1998; pp. 271-277.

Daniel J. Kane; "Real-Time Measurement of Ultrashort Laser Pulse Using Principal Component Generalized Projection"; IEEE Journal of Selected Topics in Quantum Electronics; vol. 4, No. 2; Mar./Apr. 1998; pp. 278-284.

Scott A. Diddams et al.; "Characterizing the Nonlinear Propagation of Femtosecond Pulses in Bulk Media"; IEEE Journal of Selected Topics in Quantum Electronics, vol. 4, No. 2; Mar./Apr. 1998; pp. 306-316.

Michael J. Stimson et al.; "Noisy-light correlation functions by frequency resolved optical gating"; J. Opt. Soc. Am. B, vol. 15, No. 2; Feb. 1998; pp. 505-514.

J. W. Nicholson et al.; "Full-field characterization of femtosecond pulses by spectrum and cross-correlation measurements"; Optics Letters, vol. 24, No. 23; Dec. 1, 1999; pp. 1774-1776.

F. Romstad et al.; "Measurement of Pulse Amplitude and Phase Distortion in a Semiconductor Optical Amplifier: from Pulse Compression to Breakup"; IEEE Photonics Technology Letters, vol. 12, No. 12; Dec. 2000; pp. 1674-1676.

Tzu-Ming Liu et al.; "Triple-optical autocorrelation for direct optical pulse-shape measurement"; Applied Physics Letters, vol. 81, No. 8; Aug. 19, 2002; pp. 1402-1404.

Yoshihiro Takagi et al.; "Multiple- and single-shot autocorrelator based on two-photon conductivity in semiconductors"; Optics Letters, vol. 17, No. 9; May 1, 1992; pp. 658-660.

Thomas J. Dunn et al.; "Experimental Determination of the Dynamics of a Molecular Nuclear Wave Packet via the Spectra of Spontaneous Emission"; Physical Review Letters, vol. 70, No. 22; May 31, 1993; pp. 3388-3391.

A.N. Naumov et al.; "Frequency-time and time-space mappings for single-shot coherent four-wave mixing with chirped pulses and broad beams"; Journal of Raman Spectroscopy, 2001; pp. 960-970.

E.T.J. Nibbering et al.; "Spectral determination of the amplitude and the phase of intense ultrashort optical pulses"; J. Opt. Soc. Am. B, vol. 13, No. 2; Feb. 1996; pp. 317-329.

Victor Wong et al.; "Ultrashort-pulse characterization from dynamic spectrograms by iterative phase retrieval"; J. Opt. Soc. Am. B, vol. 14, No. 4; Apr. 1997; pp. 944-949.

Sarah M. Gallagher et al.; "Heterodyne detection of the complete electric field of femtosecond four-wave mixing signals"; J. Opt. Soc. Am. B, vol. 15, No. 8; Aug. 1998; pp. 2338-2345.

C. Dorrer et al.; "Single-shot real-time characterization of chirped-pulse amplification systems by spectral phase interferometry for direct electric-field reconstruction"; Optics Letters, vol. 24, No. 22; Nov. 15, 1999; pp. 1644-1646.

C. Dorrer; "Implementation of spectral phase interferometry for direct electric-field reconstruction with a simultaneously recorded reference interferogram"; Optics Letters, vol. 24, No. 21; Nov. 1, 1999; pp. 1532-1534.

C.Y. Chien et al.; "Single-shot chirped-pulse spectral interferometry used to measure the femtosecond ionization dynamics of air"; Optics Letters, vol. 25, No. 8; Apr. 15, 2000; pp. 578-580.

J.W. Nicholson et al.; "Unbalanced third-order correlations for full characterization of femtosecond pulses"; Optics Letters, vol. 25, No. 24; Dec. 15, 2000; pp. 1801-1803.

Sergey Yeremenko et al.; "Frequency-resolved pump-probe characterization of femtosecond infrared pulses"; Optics Letters, vol. 27, No. 13; Jul. 1, 2002; pp. 1171-1173.

J. M. Dudley, et al.; "Direct measurement of pusle distortion near the zero-disperson wavelength in an optical fiber by frequency-resolved optical gating"; Optics Letters, vol. 22, No. 7; Apr. 1, 1997; 457-459.

M.C. Chen et al.; "Freezing phase scheme for fast adaptive control and its application to characterization of femtosecond coherent optical pulses reflected from semiconductor saturable absorber mirrors"; J. Opt. Soc. Am. B, vol. 22, No. 5; May 2005; pp. 1134-1142.

I. Amat-Roldan et al.; "Measurement of electric field by interferometric spectral trace observation"; Optics Letters, vol. 30, No. 9; May 1, 2005; pp. 1063-1065.

I. Amat-Roldan et al.; "Starch-based second-harmonic-generated colinear frequency-resolved optical gating pulse characterization at the focal plane of a high-numerical-aperture lens"; Optics Letters, vol. 29, No. 19; Oct. 1, 2004; pp. 2282-2284.

Gregory D. Goodno et al.; "Ultrafast heterodyne-detected transient-grating spectroscopy using diffractive optics"; Optical Society of America, vol. 15, No. 6, Jun. 1998; pp. 1791-1794.

L. Misoguti et al.; "Generation of Broadband VUV Light Using Third-Order Cascaded Processes"; Physical Review Letters, vol. 87, No. 1, Jul. 2, 2001; pp. 013601-1-013601-4.

D. Zeidler et al.; "Amplification of tailored white-light continuum"; Applied Physics, B74 (Suppl), 2002; pp. S51-S56.

T. Brixner et al.; "Generation and characterization of polarization-shaped femtosecond laser pulses"; Applied Physics B74 (Suppl), 2002; pp. S133-S144.

Jeffrey L. Krause et al.; "Creating and Detecting Shaped Rydberg Wave Packets"; Physical Review Letters, vol. 79, No. 25; Dec. 22, 1997; pp. 4978-4981.

S. Backus et al.; "16-fs, 1-µ J ultraviolet pulses generated by third-harmonic conversion in air"; Optics Letters, vol. 21, No. 9; May 1, 1996; pp. 665-667.

Julie A. Gruetzmacher et al.; "Few-cycle mid-infrared pulse generation, characterization and coherent propagation in optically dense media"; Review of Scientific Instruments, vol. 73, No. 6; Jun. 2002; pp. 2227-2236.

T. Kobayashi et al.; "Tunable visible and near-infrared pulse generator in a 5 fs regime"; Appl. Phys. B 70 (Suppl); 2000; pp. S239-S246.

A. Poppe et al; "Few-cycle optical waveform synthesis"; Applied Physics B 72; 2001; pp. 373-376.

Peifang Tian et al.; "Ultrafast measurement of two-photon absorption by loss modulation"; Optics Letters, vol. 27, No. 18; Sep. 15, 2002; pp. 1634-1636.

M. Hentschel et al.; "Generation of 0.1-TW optical pulses with a single-stage Ti:sapphire amplifier at a 1-kHz repetition rate"; Appl. Phys. B 70 [Suppl]; 2000; pp. S161-S164.

Photogen Technologies, Inc., "Photogen-Technology"; www.photogen.com/body/tech_body.html; Dec. 20, 2001 (19 pages).

W.M. Sharman et al.; "Photodynamic therapeutics: basic principles and clinical applications"; DDT, vol. 4, No. 11; Nov. 1991; pp. 507-517.

Allison Albrecht Ferro et al.; "Complete femtosecond linear free induction decay, Fourier algorithm for dispersion relations and accuracy of the rotating wave approximation"; Journal of Chemical Physics, vol. 114, No. 10; Mar. 8, 2001; pp. 4649-4656.

J.P. Ogilvie et al.; "Fourier transform measurement of two-photon excitation spectra: applications to microscopy and optimal control"; Optics Letters, vol. 30, No. 8; Apr. 15, 2005; pp. 911-913.

D. Lalovic et al.; "Quantum mechanics in terms of non-negative smoothed Wigner functions"; Physical Review A, vol. 46, No. 3; Aug. 1, 1992; pp. 1206-1212.

Christopher J. Bardeen et al.; "Using time-dependent rate equations to describe chirped pulse excitation in condensed phases"; Chemical Physics Letters 302; 1999; pp. 405-410.

Yu-Chen Shen et al.; "What can short-pulse pump-probe spectroscopy tell us about Franck-Condon dynamics?"; Journal of Chemical Physics, vol. 110. No. 20; May 22, 1999; pp. 9793-9806.

M. Ovchinnikov et al.; "Semiclassical molecular dynamics computation of spontaneous light emission in the condensed phase: Resonance Raman spectra"; Journal of Chemical Physics, vol. 114, No. 16; Apr. 22, 2001; pp. 7130-7143.

S. Yeremenko et al.; "The criterion of pulse reconstruction quality based on Wigner representation"; Applied Physics B 70 (Suppl); 2000; pp. S109-S117.

David C. Clary; "Quantum Theory of Chemical Reaction Dynamics"; Science, vol. 279, Mar. 20, 1998; p. 1879.

B.D. Fainberg; "Diagram Technique for Nonlinear Optical Spectroscopy in the Fast Electronic Dephasing Limit"; Journal of the Chinese Chemical Society, 47; 2000; pp. 579-582.

Chantal Daniel et al.; "Deciphering the Reaction Dynamics Underlying Optimal Control Laser Fields"; Science Magazine, vol. 299; Jan. 24, 2003; pp. 536-539.

T. Witte et al.; "Controlling molecular ground-state dissociation by optimizing vibrational ladder climbing"; Journal of Chemical Physics, vol. 118, No. 5; Feb. 1, 2003; pp. 2021-2024.

R.J. Levis et al.; "Closing the Loop on Bond Selective Chemistry Using Tailored Strong Field Laser Pulses"; The Journal of Physical Chemistry, vol. 106, No. 27; Jul. 11, 2002; pp. 6427-6444.

Mustafa Demirplak et al.; "Optical control of molecular dynamics in a liquid"; Journal of Chemical Physics, vol. 116, No. 18; May 8, 2002; pp. 8028-8035.

M. Bergt et al.; "Time-resolved organometallic photochemistry Femtosecond fragmentation and adaptive control of CpFe(CO)2X (X=Cl,Br,1)"; Journal of Organometallic Chemistry 661; 2002; pp. 199-209.

Ben R. Torralva et al; "Mechanisms for laser control of chemical reactions"; Journal of Modern Optics, vol. 49, No. 3/4; 2002; pp. 593-625.

N.H. Damrauer et al.; "Control of bond-selective photochemistry in CH2BrCl using adaptive femtosecond pulse shaping"; The European Physical Journal D, 20, 2002; pp. 71-76.

L. Windhorn et al.; "Molecular dissociation by mid-IR femtosecond pulses"; Chemical Physics Letters 357, May 3, 2002; pp. 85-90.

Robert J. Levis et al.; "Selective Bond Dissociation and Rearrangement with Optimally Tailored, Strong-Field Laser Pulses"; Science Magazine, vol. 292; Apr. 27, 2001; pp. 709-713.

T. Brixner et al.; "Problem complexity in femtosecond quantum control"; Chemical Physics 267; 2001; pp. 241-246.

O.M. Sarkisov et al.; "Control of elementary chemical reactions by femtosecond light pulses"; Quantum Electronics, vol. 31, No. 6; 2001; pp. 483-488.

Julie A. Mueller et al.; "Competing isomeric product channels in the 193 nm photodissociation of 2-chloropropene and in the unimolecular dissociation of the 2-propenyl radical"; Journal of Chemical Physics, vol. 114, No. 10; Mar. 8, 2001; pp. 4505-4521.

Chantal Daniel et al.; "Analysis and control of laser induced fragmentation processes in CpMn(CO)3"; Chemical Physics 267; 2001; pp. 247-260.

A. Glass et al.; "Control of the photodissociation of CsCl"; Applied Physics B 71; 2000; pp. 267-276.

T. Frohnmeyer et al.; "Femtosecond pump-probe photoelectron spectroscopy on Na2: a tool to study basic coherent control schemes"; Applied Physics B 71; 2000; pp. 259-266.

M. Bergt et al.; "Controlling the Femtochemistry of Fe(CO)5"; J. Phys. Chem. A, vol. 103, No. 49; 1999; pp. 10381-10387.

A. Assion et al.; "Coherent control by a single phase shaped femtosecond laser pulse"; Chemical Physics Letters 259; Sep. 13, 1996; pp. 488-494.

Langchi Zhu et al.; "Coherent Laser Control of the Product Distribution Obtained in the Photoexcitation of HI"; Science Magazine, vol. 270; Oct. 6, 1995; pp. 77-80.

Yu-hui Chiu et al.; "Vibrational mode effects, scattering dynamics and energy disposal in reaction of C2H2 with methane"; J. Chem. Phys., vol. 102, No. 3; Jan. 15, 1995; pp. 1199-1216.

J.S. Keller et al.; "Selective bond fission in methyl mercaptan at 193 nm via radial derivative coupling between the 21A" and 11A" adiabatic electronic states"; J. Chem. Phys. vol. 96, No. 6; Mar. 15, 1992; pp. 4324-4329.

I. Bar et al.; "Mode-selective bond fission: Comparison between the photodissociation of HOD (0,0,1) and HOD (1,0,0)"; J. Chem. Phys. vol. 95, No. 5; Sep. 1, 1991; pp. 3341-3346.

Michael J. Bronikowski et al.; "Bond-specific chemistry: OD:OH product ratios for the reactions H+HOD(100) and H+HOD(001)"; J. Chem. Phys., vol. 95, No. 11; Dec. 1, 1991; pp. 8647-8648.

I. Bar et al.; "Direct observation of preferential bond fission by excitation of a vibrational fundamental: Photodissociation of HOD (0,0,1)"; J. Chem. Phys., vol. 93, No. 3; Aug. 1, 1990; pp. 2146-2148.

R.L. VanderWal et al.; "Selectively breaking the O-H bond in HOD"; J. Chem. Phys., vol. 92, No. 1; Jan. 1, 1990; pp. 803-805.

Neil Shafer et al.; "Isotope effect in the photodissociation of HDO at 157.5 nm"; J. Chem. Phys., vol. 90, No. 11; Jun. 1, 1989; pp. 6807-6808.

L.J. Butler et al.; "The electronic state-selective photodissociation of CH2BrI at 248, 210 and 193 nm"; J. Chem. Phys. vol. 86, No. 4; Feb. 15, 1997; pp. 2051-2074.

L.J. Butler et al.; "Bond selective photochemistry in CH2BrI through electronic excitation at 210 nm"; J. Chem. Phys., vol. 84, No. 7; Apr. 1, 1986; pp. 4104-4106.

David J. Tannor et al.; "Control of selectivity of chemical reaction via control of wave packet evolution"; J. Chem. Phys., vol. 83, No. 10; Nov. 15, 1985; pp. 5013-5018.

Christopher J. Bardeen et al.; "Quantum Control of NaI Photodissociation Reaction Product States by Ultrafast Tailored Light Pulses"; J. Phys. Chem. A, vol. 101, No. 20; 1997; pp. 3815-3822.

V.A. Apkarian; 'Comment on "Time-resolved laser induced harpoon reactions"'; J. Chem. Phys. vol. 106, No. 12; Mar. 22, 1997; pp. 5298-5299.

R.B. Vrijen et al.; "Limitations on quantum ladder climbing in complex systems"; Physical Review A, vol. 56, No. 3; Sep. 1997; pp. 2205-2212.

Lutfur R. Khundkar et al.; "Ultrafast Molecular Reaction Dynamics in Real-Time: Progress Over a Decade"; Annu. Rev. Phys. Chem., 1990; pp. 15-60.

Stuart A. Rice; "Optical control of reactions"; Nature magazine, vol. 403; Feb. 3, 2000; pp. 496-497.

Richard N. Zare; "Laser Control of Chemical Reactions"; Science magazine, vol. 279; Mar. 20, 1998; pp. 1875-1879.

Stuart A. Rice; "Active Control of Molecular Dynamics: Coherence versus Chaos"; Journal of Statistical Physics, vol. 101, Nos. 1/2; 2000; pp. 187-212.

Herschel Rabitz et al.; "Whither the Future of Controlling Quantum Phenomena?"; Science magazine, vol. 288; May 5, 2000; pp. 824-828.

Yuri T. Mazurenko; "Spectral Holography and Spectral Nonlinear Optics of Ultrashort Pulses"; Journal of the Chinese Chemical Society, vol. 47, No. 4A; 2000; pp. 679-683.

Marcos Dantus; "Coherent Nonlinear Spectroscopy: From Femtosecond Dynamics to Control"; Annu. Rev. Phys. Chem. 2001; pp. 639-679, C1-C7.

Stuart A. Rice; "Interfering for the good of a chemical reaction"; Nature magazine; vol. 409; Jan. 18, 2001; pp. 422-426.

Wolfgang Kiefer et al.; "Femtosecond time-resolved spectroscopy of elementary molecular dynamics"; Naturwissenschaften; 2002; pp. 250-258.

Alois Renn et al.; "Multidimensional Holography by Persistent Spectral Hole Burning"; The Journal of Physical Chemistry A, vol. 106, No. 13; Apr. 4, 2002; pp. 3045-3060.

T.C. Weinacht et al.; "Using feedback for coherent control of quantum systems"; Journal of Optics B: Quantum and Semiclassical Optics; 2002; pp. R35-R52.

Niels E. Henriksen; "Laser control of chemical reactions"; Chem. Soc. Rev. 3137 42; 2002; pp. 37-42.

Stuart A. Rice et al.; "Active control of product selection in a chemical reaction: a view of the current scene"; Phys. Chem. Chem. Phys.; 2002; pp. 1683-1700.

Allen J. Bard et al.; "Holy Grails in Chemistry"; American Chemical Society, vol. 28, No. 3; Mar. 1995.

Marcos Dantus; "Ultrafast Probing and Control of Molecular Dynamics: Beyond the Pump-Probe Method"; pp. 169-188. Kuhn & Weyh SRZ Sep. 4, 2001.

Bern Kohler et al.; "Controlling the Future of Matter"; Acc. Chem. Res., vol. 28, No. 3; 1995; pp. 133-140.

M.R. Fetterman et al.; "Propagation of Complex Laser Pulses in Optically Dense Media"; The American Physical Society, Physical Review Letters, vol. 82, No. 20, May 17, 1999; pp. 3984-3987.

D. Yelin et al.; "Adaptive femtosecond pulse compression"; Optics Letters, vol. 22, No. 23, Dec. 1, 1997; pp. 1793-1795.

A.V. Sokolov; "Subfemtosecond compression of periodic laser pulses"; Optics Letters, vol. 24, No. 17, Sep. 1, 1999; pp. 1248-1250.

H.S. Eisenberg et al.; "Phase Defects in Self-Focusing of Ultrashort Pulses"; Physical Review Letters, vol. 83, No. 3, Jul. 19, 1999; pp. 540-543.

D.M. Villeneuve et al.; "Using frequency-domain manipulation of stretched femtosecond laser pulses to create fast rise and fall times on picosecond pulses"; Applied Physics B74 (Suppl), 2002; pp. S157-S161.

Dai-Sik Kim et al.; "Femtosecond-pulse distortion in quantum wells"; Appl. Phys B 74, vol. 48. No. 24; Dec. 15, 1993; pp. 17902-17905.

Anthony P. Peirce et al.; "Optimal control of quantum-mechanical systems: Existence, numerical approximation and applications"; Physical Review A, vol. 37, No. 12; Jun. 15, 1988; pp. 4950-4964.

J.M. Geremia et al.; "Incorporating physical implementation concerns into closed loop quantum control experiments"; Journal of Chemical Physics, vol. 113, No. 24; Dec. 22, 2000; pp. 10841-10848.

Thomas Hornung et al.; "Teaching optimal control theory to distill robust pulses even under experimental constraints"; Physical Review A, vol. 65; 2002; pp. 021403-1-021403-4.

Jianshu Cao et al.; "Intrapulse Dynamical Effects in Multiphoton Processes: Theoretical Analysis"; J. Phys. Chem. A; vol. 102, 1998; pp. 4284-4290.

Amichay Vardi et al.; "Laser catalysis with pulses"; Physical Review A, vol. 58, No. 2; Aug. 1998; pp. 1352-1360.

Kazuya Takasago et al.; "Evaluation of Femtosecond Pulse Shaping with Low-Loss Phase-Only Masks"; IEEE Journal of Selected Topics in Quantum Electronics, vol. 4, No. 2; Mar./Apr. 1998; pp. 346-352.

M.E. Fermann et al.; "Shaping of ultrashort optical pulses by using an integrated acousto-optic tunable filter"; Optics Letters, vol. 18, No. 18; Sep. 15, 1993; pp. 1505-1507.

V.L. da Silva et al.; "Nonlinear pulse shaping and causality"; Optics Letters, vol. 18, No. 8; Apr. 15, 1993; pp. 580-582.

E. Zeek et al.; "Adaptive pulse compression for transform-limited 15-fs high-energy pulse generation"; Optics Letters, vol. 25, No. 8; Apr. 15, 2000; pp. 587-589.

A. Apolonski et al.; "Controlling the Phase Evolution of Few-Cycle Light Pulses"; Physical Review Letters, vol. 85, No. 4; Jul. 24, 2000; pp. 740-743.

Christophe Dorrer et al.; "Phase Amplitude Coupling in Spectral Phase Modulation"; IEEE Journal of Selected Topics in Quantum Electronics, vol. 4, No. 2; Mar./Apr. 1998; pp. 342-345.

David J. Jones et al.; "Carrier-Envelope Phase Control of Femtosecond Mode-Locked Lasers and Direct Optical Frequency Synthesis"; Science magazine, vol. 288; Apr. 28, 2000; pp. 635-639.

Vladimir Kalosha et al.; "Generation of Single Dispersion Precompensated 1-fs Pulses by Shaped-Pulse Optimized High-Order Stimulated Raman Scattering"; Physical Review Letters, vol. 88, No. 10; Mar. 11, 2002; pp. 103901-1-13901-4.

Donna Strickland et al.; "Compression Of Amplified Chirped Optical Pulses"; Optics Communications; vol. 55, No. 6; Oct. 15, 1985; pp. 447-449.

H. Wang et al.; "Abstract-20-fs pulse shaping with a 512-element phase-only liquid crystal modulator"; IEEE Journal Of Selected Topics In Quantum Electronics; 7(4): 718-727; Jul./Aug. 2001 (1 page).

L. Xu et al.; "Abstract-Programmable chirp compensation for 6-fs pulse generation with a prism-pair-formed pulse shaper"; IEEE Journal Of Quantum Electronics; 36 (8): 893-899; Aug. 2000 (1 page).

CVI Laser Corporation; "TNM-2 Negative Group Velocity Dispersion Mirrors"; www.cvilaser.com/ultra-fast; Jan. 13, 2002 (2 pages).

H. Takada et al.; "Large-ratio stretch and recompression of sub-10-fs pulses utilizing dispersion managed devices and a spatial light modulator"; Appl. Phys. B 74 [Suppl.]; 2002; pp. S253-S257.

N. Karasawa et al.; "Optical pulse compression to 5.0 fs by by use only a spatial light modulator for phase compensation"; J. Opt. Soc. Am. B, vol. 18, No. 11; Nov. 2001; pp. 1742-1746.

C.P.J. Barty et al.; "Generation of 18-fs, multiiterawatt pulses by regenerative pulse shaping and chirped-pulse amplification"; Optics Letters, vol. 21, No. 9; May 1, 1996; pp. 668-670.

Marcos Dantus; GeneticAlgorithm-v4.nb to simulate an adaptive genetic algorithm;Oct. 2001; pp. 1-7.

M. Hacker et al.; "Iterative Fourier transform algorithm for phase-only pulse shaping"; Optics Express, vol. 9, No. 4, Aug. 13, 2001; pp. 191-199.

T. Brixner et al.; "Feedback-controlled optimization of amplified femtosecond laser pulses"; Applied Physics B 68; 1999; pp. 281-284.

A. Efimov et al.; "Minimization of dispersion in an ultrafast chirped pulse amplifier using adaptive learning"; Appl. Phys. B 70 (Suppl); 2000; pp. S133-S141.

D. Zeidler et al.; "Evolutionary algorithms and their application to optimal control studies"; Physical Review A, vol. 64; 2001; pp. 023420-1-023420-13.

C. Rangan et al.; "Optimally shaped terahertz pulses for phase retrieval in a Rydberg-atom data register"; Physical Review A, vol. 64; 2001; pp. 033417-1-033417-5.

T. Tanabe et al.; "Compensation for a Transfer Function of a Regenerative Amplifier to Generate Accurately Shaped Ultrashort Pulses in Both the Amplitude and Phase"; IEE J. of Selected Topics in QUantum Elecronics, vol. 10, No. 1; Jan./Feb. 2004; pp. 221-228.

Feurer, T., et al.; "Coherent Control Over Collective Polariton Excitations: The Dawn of Polaritonics;" 2002 Thirteenth International Conference on Ultrafast Phenomena, Technical Digest (Tops vol. 72); Opt. Soc. America; XP008086358; pp. 541-545.

Sato, Masamichi, et al.; "Adaptive Pulse Shaping of Femtosecond Laser Pulses in Amplitude and Phase Through a Single-Mode Fiber by Referring to Frequency-Resolved Optical Gating Patterns;" Jpn. J. Appl. Phys., vol. 41(2002); Part 1 No. 6A, Jun. 2002; XP-002436366; pp. 3704-3709.

Gee, S., et al.; "Ultrashort Pulse Generation by Intracavity Spectral Shaping and Phase Compensation of External-Cavity Modelocked Semiconductor Lasers;" IEEE Journal of Quantum Electronics, vol. 36, No. 9, Sep. 2000; XP-002462407; pp. 1035-1040.

Anderson, M.E. et al.; "The effects of noise on ultrashort-optical-pulse measurement using SPIDER"; Appl. Phys. B 70 (Suppl.); 2000; pp. S85-S93.

Assion, A. et al.; "Control of Chemical Reactions by Feedback-Optimized Phase-shaped Femtosecond Laser Pulses"; Science Magazine, vol. 282; Oct. 30, 1998; pp. 919-922.

Baltuska, Andrius et al.; "Amplitude and phase characterization of 4.5-fs pulses by frequency-resolved optical gating"; Optics Letters, vol. 23, No. 18, Sep. 15, 1998; pp. 1474-1476.

Baltuska, Andrius et al.; "Visible pulse compression to 4 fs by optical parametric amplification and programmable dispersion control"; Optics Letters, vol. 27, No. 5, Mar. 1, 2002; pp. 306-308.

Baumert, T. et al.; "Femtosecond pulse shaping by an evolutionary algorithm with feedback"; Appl. Phys. B 65 (1997); pp. 779-782.

Belfield, K.D. et al.; "Two-photon photoinitiated polymerization"; J. Phys. Org. Chem. 13(12): 837-849 (Dec. 2000).

Bhattacharya, N. et al.; Phys. Rev. Lett. 88 (2002) 137901-1.

Brattke, S. et al.; "Generation of Photon Number States on Demand via Cavity Quantum Electrodynamics"; Phys. Rev. Lett.; Apr. 16, 2001; vol. 86, No. 16; pp. 3534-3537.

Brixner, T. et al.; "Feedback-controlled femtosecond pulse shaping"; Appl. Phys. B 70 (Suppl.) 2000; pp. S119-S124.

Broers, B. et al.; "Diffraction and focusing of spectral energy in multiphoton processes"; Phys. Rev. A; 1992; 46, 2749.

Broers, B. et al.; "Large interference effects of small chirp observed in 2-photon absorption"; Opt. Commun. 1992, 91, 57.

Bucksbaum, Philip; "An atomic dimmer switch"; Nature; Nov. 19, 1998; vol. 396; pp. 217-219.

Buist, A.H. et al.; "Probing microscopic chemical environments with high-intensity chirped pulses"; Optics Letters 24, 244-246 (1999).

Chilla, Juan L.A. et al.; "Direct determination of the amplitude and the phase of femtosecond light pulses"; Jan. 1, 1991, vol. 16, No. 1; Optics Letters; pp. 39-41.

Chu, K.C. et al.; "Direct measurement of the spectral phase of femtosecond pulses"; Optics Letters, vol. 20, No. 8; Apr. 15, 1995; pp. 904-906.

Clara et al.; "Femtosecond laser mass spectroscopy of ferrocenes: photochemical stabilization by bridged cyclopentadienyl rings?"; International Journal of Mass Spectrometry, Elsevier Science Publishers; vol. 203, No. 1-3; Dec. 26, 2000; pp. 71-81.

Clement, Tracy Sharp et al.; "Single-Shot measurement of the amplitude and phase of ultrashort laser pulses in the violet"; Jan. 1, 1995; Optics Letters, vol. 20, No. 1; pp. 70-72.

Cormack, I.G. et al.; "Practical measurement of femtosecond optical pulses using time-resolved optical gating"; Optics Communications 194 (Jul. 15, 2001); pp. 415-424.

Cumpston, B.H. et al.; "New Photopolymers based on Two-Photon Absorbing Chromophores and Application to Three-Dimensional Microfabrication and Optical Storage"; Mat. Res. Soc. Symp. Proc.; vol. 488.

Cumpston, B.H. et al.; "Two-photon polymerization initiators for three-dimensional optical data storage and microfabtrication"; Letters to Nature, pp. 51-54.

Dela Cruz, J.M. et al.; "Multiphoton intrapulse interference 3: Probing microscopic chemical environments"; J. Phys. Chem. A 2004.

Dietrich, P. et al.; "Determining the absolute carrier phase of a few-cycle laser pulse"; Optics Letters, vol. 25, No. 1, Jan. 1, 2000; pp. 16-18.

Ding, Y.; "Femtosecond pulse shaping by dynamic holograms in photorefractive multiple quantum wells"; Optics Letters; May 15, 1997; vol. 22, No. 10; pp. 718-720.

Dorrer, C. et al.; "Direct space-time characterization of the electric fields of ultrashort optical pulses"; Optics Letters, vol. 27, No. 7, Apr. 1, 2002; pp. 548-550.

Dorrer, Christophe et al.; "Precision and consistency criteria in spectral phase interferometry for direct electric-field reconstruction"; J. Opt. Soc. Am. B, vol. 19, No. 5, May 2002; pp. 1030-1038.

Drexler, W. et al.; In vivo ultrahigh-resolution optical coherence tomography; Optics Letters; Sep. 1, 1999; vol. 24, No. 17; pp. 1221-1223.

Dudley, John M. et al.; "Complete Characterization of Ultrashort Pulse Sources at 1550 nm"; IEEE Journal of Quantum Electronics, vol. 35, No. 4; Apr. 1999; pp. 441-450.

Dudovich, N. et al.; "Transform-limited pulses are not optimal for resonant multiphoton transitions"; Phys. Rev. Lett. 86, 47-50 (2001).

Gallmann, L. et al.; "Spatially resolved amplitude and phase characterization of femtosecond optical pulses"; Optics Letters, vol. 26, No. 2, Jan. 15, 2001; pp. 96-98.

Gallmann, L. et al.; "Techniques for the characterization of sub-10-fs optical pulses: a comparison"; Appl. Phys. B 70 (Suppl), 2000; pp. S67-S75.

Garcia-Ripoll, J.J. et al.; "Speed Optimized Two-Qubit Gates with Laser Coherent Control Techniques for Ion Trap Quantum Computing"; Physical Review Letters; vol. 91, No. 5; Oct. 10, 2003; p. 157901-1-157901-4.

Geindre, J.P. et al.; "Single-shot spectral interferometry with chirped pulses"; Optics Letters, vol. 26, No. 20, Oct. 15, 2001; pp. 1612-1614.

Goswami, D.; "Optical pulse shaping approaches to coherent control"; Physics Reports; 374 (2003); p. 385-481.

Goswami, D.; "Ultrafast Pulse Shaping approaches to Quantum Computing"; Indian Institute of Technology; Dec. 24, 2003.

Hacker, M. et al.; "Frequency doubling of phase-modulated, ultrashort laser pulses"; Appl. Phys. B 73; (2001); pp. 273-277.

Hasan, T. et al.; "Photodynamic Therapy of Cancer"; Chapter 40 in Holland Frei Cancer Medicine, BC Dekker Inc. (2003).

Hillegas, C.W. et al.; "Femtosecond laser pulse shaping by use of microsecond radio-frequency pulses"; Optics Letters; May 15, 1994; vol. 19, No. 10; pp. 737-739.

Hornung, Thomas et al.; "Adapting optimal control theory and using learning loops to provide experimentally feasible shaping mask patterns"; Journal of Chemical Physics, vol. 115, No. 7; Aug. 15, 2001; pp. 3105-3111.

Hosseini, S. Abbas et al.; "Coherent control of multiphoton transitions with femtosecond pulse shaping"; Physical Review A, pp. 033410-1-033410-7.

Iaconis, C. et al.; "Direct Interferometric Techniques for Characterizing Ultrashort Optical Pulses"; IEEE Journal of Selected Topics in Quantum Electronics, vol. 4, No. 2; Mar./Apr. 1998; pp. 285-294.

Iaconis, C. et al.; "Spectral phase interferometry for direct electric-field reconstruction of ultrashort optical pulses"; Optics Letters, vol. 23, No. 10, May 15, 1998; pp. 792-794.

Imeshev, G. et al.; "Engineerable femtosecond pulse shaping by second-harmonic generation with Fourier synthetic quasi-phase-matching gratings"; Optics Leters; Jun. 1, 1998; vol. 23, No. 11; pp. 864-866.

Kaindl, Robert A. et al.; "Generation, shaping, and characterization of intense femtosecond pulses tunable from 3 to 20 um"; J. Opt. Soc. Am. B, vol. 17, No. 12, Dec. 2000; pp. 2086-2094.

Kakehata, Masayuki et al.; "Single-shot measurement of carrier-envelope phase changes by spectral interferometry"; Optics Letters, vol. 26, No. 18, Sep. 15, 2001; pp. 1436-1438.

Kane, Daniel J. et al.; "Single-shot measurement of the intensity and phase of an arbitrary ultrashort pulse by using frequency-resolved optical gating"; May 15, 1993, vol. 18, No. 10 Optics Letters; pp. 823-825.

Kane, Daniel J. et al.; "Single-shot measurement of the intensity and phase of a femtosecond UV laser pulse with frequency-resolved optical gating"; Jul. 15, 1994, vol. 19, No. 14; Optic Letters; pp. 1061-1063.

Kim, D.S. et al.; "Femtosecond pulse distortion in GaAs quantum wells and its effect on pump-probe or four-wave-mixing experiments"; Dec. 15, 1994; Physical Review B, vol. 50, No. 24, pp. 18 240-18 249.

Kohler, Bern et al.; "Phase and intensity characterization of femtosecond pulses from a chirped-pulse amplifier by frequency-resolved optical gating"; Mar. 1, 1995, vol. 20, No. 5, Optics Letters; pp. 483-485.

Kosik, Ellen M. et al.; "The effects of noise on ultrashort optical pulse measurement using SPIDER"; The Institute of Optics, University of Rochester, Rochester, NY; pp. 21-23.

Kovtoun et al.; "Mass-correlated pulsed extraction: theoretical analysis and implemetation with a linear matrix-assisted laser desorption/ionization time of flight mass spectrometer"; Journal of the American Society for Mass Spectrometry, Elsevier Science Inc.; vol. 11, No. 10; Oct. 2000; pp. 841-853.

Lange, H. Rudiger et al.; "Reconstruction of the Time Profile of Femtosecond Laser Pulses Through Cross-Phase Modulation"; IEEE Journal of Selected Topics in Quantum Electronics, vol. 4, No. 2; Mar./Apr. 1998; pp. 295-300.

Larson, D.R. et al.; "Water soluble quantum dots for multiphoton imaging in vivo", Science 300 1434-6, (May 30, 2003).

Leibfried, D. et al.; "Quantum information with trapped ions at NIST"; Journal of Modern Optics; Apr.-May 2003; vol. 50, No. 6/7; p. 1115-1129.

Lozovoy, V.V.; "Multiphoton intrapulse interference II: Control of two- and three-photon laser induced fluorescence with shaped pulses"; J. Chem. Phys. 118 (7): 3187-3196 (Feb. 15, 2003).

Lu, Y.M. et al.; "Highly sensitive two-photon chromophores applied to three dimensional lithographic microfabrication: design, sysnthesis and characterization towards two-photon absorption cross section"; J. Mater Chem. 14(1): 75-80 (2004).

Matuschek, N.; "Back-side-coated chirped mirrors with ultra-smooth broadband dispersion characteristics"; Applied Physics B; 71, pp. 509-522.

Meshulach, D. et al.; "Adaptive real-time femtosecond pulse shaping"; J. Opt. Soc. Am. B; May 1998; vol. 15, No. 5; pp. 1615-1619.

Meshulach, D. et al.; "Adaptive ultrashort pulse compression and shaping"; Optics Communications 138 (1997); pp. 345-348.

Meshulach, M. et al.; "Coherent quantum control of multiphoton transitions by shaped ultrashort optical pulses"; Phys. rev. A 60, 1287-1292 (1999).

Michelmann, K. et al.; "Measurement of the Page function of an ultrashort laser pulse"; Optics Communications, Oct. 15, 2001; pp. 163-170.

Mitra et al.; "Nonlinear Limits to the Information Capacity of Optical Fibre Communications"; Nature, vol. 411, pp. 1027-1030 (Jun. 28, 2001).

Nicholson, J.W. et al.; "Noise sensitivity and accuracy of femtosecond pulse retrieval by phase and intensity from correlation and spectrum only (PICASO)"; J. Opt. Soc. Am. B; vol. 19, No. 2; Feb. 2002; pp. 330-339.

Osborn, D.L. et al.; "Spectral and intensity dependence of spatially resolved two-photon conductivity defects on a GaAsP photodiode"; J. Appl. Phys. 89, 626-633 (2001).

Panasenko, Dmitriy et al; "Single-shot sonogram generation for femtosecond laser pulse diagnostics by use of two-photon absorption in a silicon CCD camera"; Aug. 15, 2002, vol. 27, No. 16; Optics Letters; pp. 1475-1477.

Pastirk, I. et al.; "Selective two-photon microscopy with shaped femtosecond pulses"; Opt. Express 11, 1695-1701 (2003).

Paye, J.; "How to Measure the Amplitude and Phase of an Ultrashort Light Pulse with an Autocorrelator and a Spectrometer"; IEEE Journal of Quantum Electronics, vol. 30, No. 11; Nov. 1994; pp. 2693-2697.

Postnikova, B.J. et al.; "Towards nanoscale three-dimensional fabrication using two-photon initiated polymerization and near-field excitation"; Microelectron. Eng. 69(2-4): 459-465 (Sep. 2003).

Reid, D.T. et al.; "Amplitude and phase measurement of mid-infrared femtosecond pulses by using cross-correlation frequency-resolved optical gating"; Optics Letters, vol. 25, No. 19, Oct. 1, 2000; pp. 1478-1480.

Roy, I. et al.; "Ceramic-based nanoparticles entrapping water-soluble photosensitizing drugs: A novel drug carrier system for photodynamic therapy"; J. Am. Chem. Soc. 125:7860-7865 (2003).

Schreier, F. et al.; "Femtosecond pulse shaping with a stratified diffractive structure"; Optics Communications 185 (2000); pp. 227-231.

Sharman, W.M. et al.; "Photodynamic therapy: basic principles and clinical applications"; Drug Discovery today 4(11):508-517 (1999).

Sharman, W.M. et al.; "Targeted photodynamic therapy via receptor mediated delivery systems"; Adv. Drug Delivery Rev. 56(1):53-76 (Jan. 2004).

Spielmann, C. et al.; "Ultrabroadband Femtosecond Lasers"; IEEE Journal of Quantum Electronics; Apr. 1994; vol. 30, No. 4; pp. 1100-1114.

Stobrawa, G. et al.; "A new high-resolution femtosecond pulse shaper"; Appl. Phys. B 72 (2001); pp. 627-630.

Sullivan, A. et al.; "Quantitative investigation of optical phase-measuring techniques for ultrashort pulse lasers"; J. Opt. Soc. Am. B, vol. 13, No. 9, Sep. 1996; pp. 1965-1978.

Sun, H.B. et al.; "Two-photon laser precision microfabrication and its applications to micro-nano devices and systems"; J. Lightwave Technol. 21(3): 624-633 (Mar. 2003).

Sweetser, John N. et al.; "Transient-grating frequency-resolved optical gating"; Apr. 15, 1997, vol. 22, No. 8; Optics Letters; pp. 519-521.

Trebino, R. et al.; "Measuring Ultrashort Laser Pulses Just Got a Lot Easier!"; Optics & Photonics News; Jun. 2001; p. 22-25.

Trebino, Rick et al.; "Measuring ultrashort laser pulses in the time-frequency domain using frequency-resolved optical gating"; Rev. Sci. Instrum. 68 (9), Sep. 1997; pp. 3277-3295.

Trebino, Rick et al.; "The Dilemma of Ultrashort-Laser-Pulse Intensity and Phase Measurement and Applications"; IEEE Journal of Quantum Electronics, vol. 35, No. 4, Apr. 1999; pp. 418-420.

Tull, J.X. et al.; "High-Resolution, Ultrafast Laser Pulse Shaping and Its Applications"; Advances in Magnetic and Optical Resonance; vol. 20;pp. 1-65.

VandenBout, D.A. et al.; "Discrete intensity jumps and intramolecular electronic energy transfer in the spectroscopy of single conjugated polymer molecules"; Science 277, 1074-1077 (1997).

Walmsley, Ian A. et al.; "Characterization of the electric field of ultrashort optical pulses"; J. Opt. Soc. Am. B, vol. 13, No. 11; Nov. 1996; pp. 2453-2463.

Walowicz, K.A. et al.; "Multiphoton intrapulse interference 1: Control of multiphoton processes in condensed phases"; J. Phys. Chem. A 106 (41): 9369-9373 (Oct. 17, 2002).

Warren, W.S.; "Chemistry with Photons"; Science; vol. 262; Nov. 12, 1993; pp. 1008-1009.

Weinacht, T.C. et al.; "Controlling the shape of a quantum wavefunction"; Nature; Jan. 1999; vol. 397; p. 233-235.

Weiner, A.M. et al.; "Programmable Shaping of Femtosecond Optical Pulses by Use of 128-Element Liquid Crystal Phase Modulator"; IEEE Journal of Quantum Electronics; vol. 28, No. 4; Apr. 1992; p. 908-920.

Weiner, A.M.; "Femtosecond pulse shaping using spatial light modulators"; Rev. Sci. Instrum. vol. 71(5); pp. 1929-1960 (2000).

Weiner, Andrew M. et al.; "Femtosecond Pulse Shaping for Synthesis, Processing and Time-to-Space Conversion of Ultrafast Optical Waveforms"; IEEE Journal of Selected Topics in Quantum Electronics, vol. 4, No. 2; Mar./Apr. 1998; pp. 317-331.

Xu, C. et al.; "Two photon optical beam induced current imaging throughout backside of integrated circuits"; Appl. Phys. Lett. 71, 2578-2580 (1997).

Yan, Y.J. et al.; "Electronic dephasing, vibrational relaxation, and solvent friction in molecular nonlinear optical line shapes"; J. Chems. Phys., Oct. 15, 1988; pp. 5160-5176.

Yang, W. et al.; "High-ratio Electro-optical Data Compression for Massive Accessing Networks Using AOM-based Ultrafast Pulse Shaping"; Journal of Optical Communications; 2001; vol. 22, No. 1; p. 694-697.

Yelin, D. et al.; "Laser scanning third-harmonic-generation microscopy in biology"; Optics Express; Oct. 11, 1999; vol. 5, No. 8; pp. 169-175.

Zeidler, D. et al.; "Adaptive compression of tunable pulses from a non-collinear-type OPA to below 16 fs by feedback-controlled pulse shaping"; Appl. Phys. B 70[Suppl.]; 2000; pp. S125-S131.

Zheng, Z. et al.; "Coherent control of second harmonic generation using spectrally phase coded femtosecond waveforms"; Chem. Phys. 267, 161-171 (2001).

Zheng, Z. et al.; "Spectral phase corelation of coded femtosecond pulses by second-harmonic generation in thick nonlinear crystals"; Opt. Lett. 25, 984-986 (2000).

Zipfel, W.R. et al.; "Nonlinear magic: multiphoton microscopy in the biosciences"; Natire Biotechnology, 121 (11): 1369-1377 (Nov. 2003).

M. Wefers et al., "Generation of High-Fidelity Programmable Ultrafast Optical Waveforms", Optics Letters, May 1, 1995, vol. 20, No. 9, pp. 1047-1049.

I. Pastirk et al., "Selective Two-Photon Microscopy with Shaped Femtosecond Pulses", Optics Express, Jul. 14, 2003, vol. 11, No. 14, pp. 1695-1701.

H. Zang et al., "Study on Frequency-Doubling Effect of the Dually Doped KTP Crystals", Journal of Synthetic Crystals, May 2000, vol. 29, No. 2, 3 pages.

English Translation of First Office Action from the Chinese Intellectual Property Office for Chinese Patent Application No. 200580006841.2, dated May 9, 2008, 27 pages.

He-gui, Zang et al.; "Study On Frequency-Doubling Effect of the Dually Doped KTP Crystals;" Journal of Synthetic Crystals, vol. 29, No. 2, May 2000; pp. 157-159.

Baltuška, Andrius et al.; "Visible Pulse Compression To 4 fs By Optical Parametric Amplification And Programmable Dispersion Control;" Optics Letters, vol. 27, No. 5, Mar. 1, 2002, pp. 306-308.

Zeek, Erik; "Pulse Shaping For High-Harmonic Generation;" Dissertation Submitted in Partial Fulfillment of the Requirements for the Degree of Doctor of Philosophy (Applied Physics) in the University of Michigan, 2000; 126 pages.

* cited by examiner

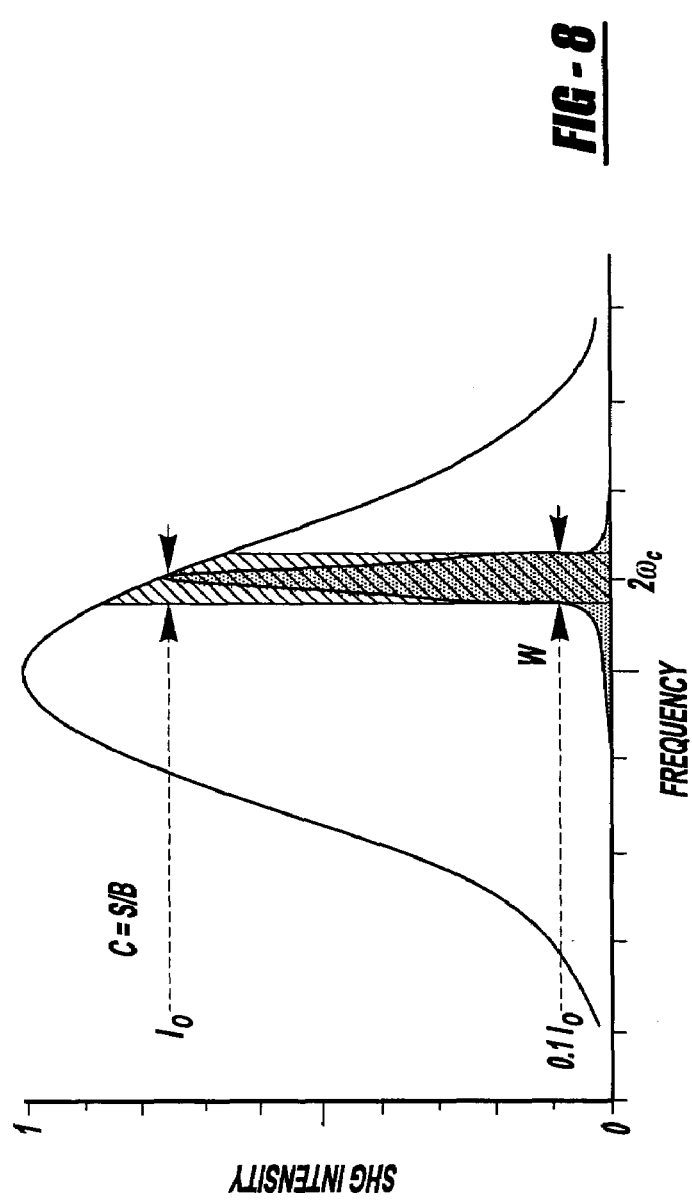
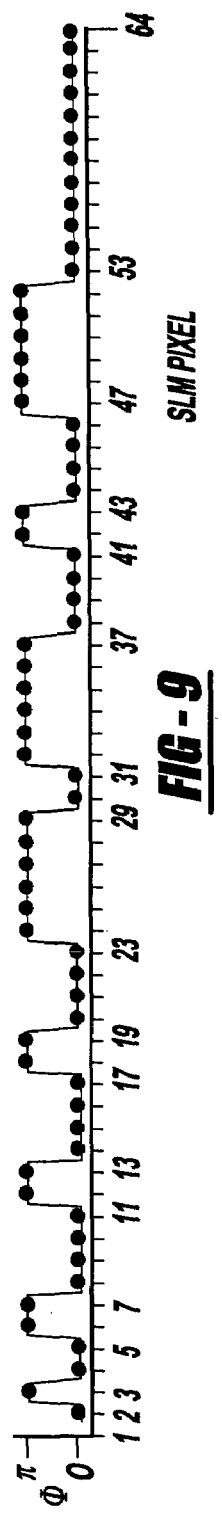
FIG-8
FIG-9

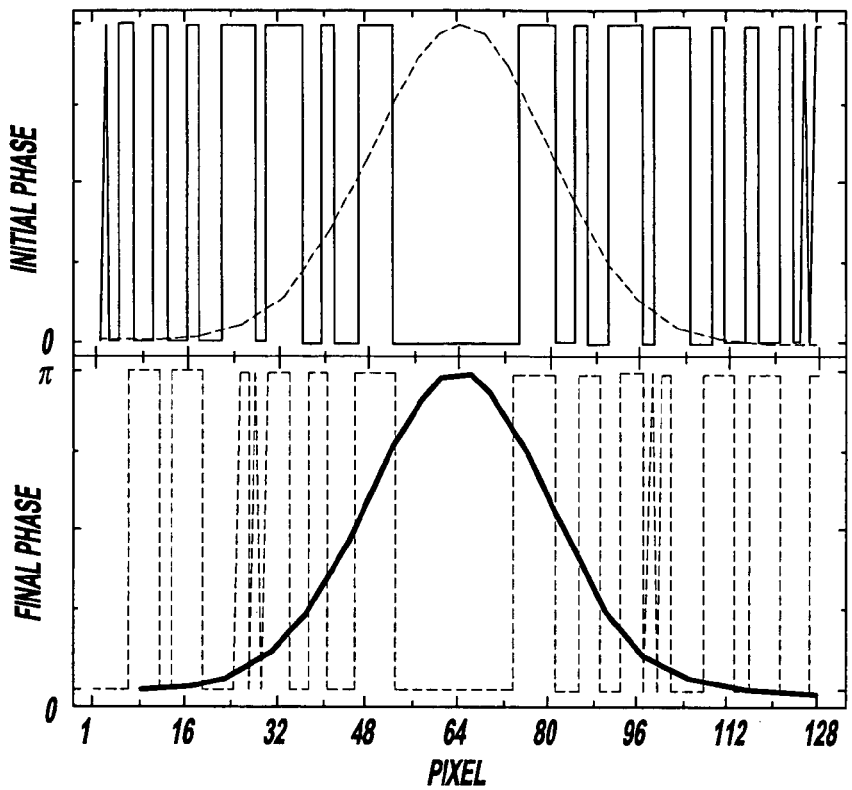
FIG - 12b
FIG - 12c
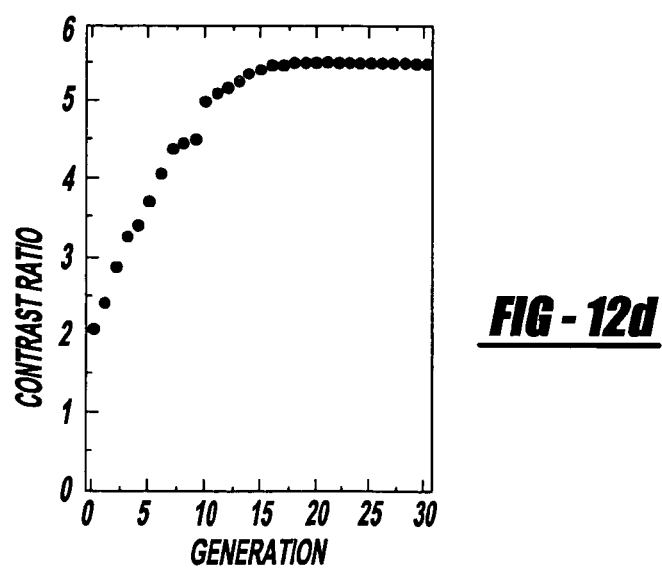
FIG - 12d

50 μm pH = 6     pH = 10

LASER SYSTEM USING ULTRA-SHORT LASER PULSES

CROSS REFERENCE TO RELATED APPLICATIONS

This is a continuation-in-part of U.S. patent application Ser. No. 10/265,211, filed Oct. 4, 2002 now U.S. Pat. No. 7,450,618, which is a continuation-in-part of PCT Serial No. PCT/US02/02548, filed on Jan. 28, 2002, which claims priority to U.S. provisional application Ser. No. 60/265,133, filed Jan. 30, 2001, which are all incorporated by reference herein.

STATEMENT OF GOVERNMENT INTEREST

A portion of this invention was made with U.S. Government support under Contract No. DE-FG02-01ER15143 awarded by the Department of Energy. The Government may have certain rights in this invention.

BACKGROUND

The present invention generally relates to a laser system and more particularly to a laser system using ultra short laser pulses and a pulse shaper.

Commercially practical femtosecond lasers have been unavailable until recently. For example, lasers which can generate 10 femtosecond or less laser pulse durations have traditionally been extremely expensive, required unrealistically high electrical energy consumption (for extensive cooling, by way of example) and depended on laser dyes that had to be replenished every month thereby leading to commercial impracticality. The efficiency of sub-10 femtosecond lasers was not practical until the year 2000 because of the prior need for dyes and flash lamps instead of YAG and Ti: Sapphire crystals pumped by light or laser emitting diodes.

Ultrashort pulses are prone to suffer phase distortions as they propagate through or reflect from optics because of their broad bandwidth. There have been recent experimental attempts to shape the phase of ultrashort pulses since shaped pulses have been shown to increase the yield of certain chemical reactions and multiphoton excitation. Pulse shaping methods allowing synthesis of complex femtosecond optical waveforms are known. As usually practiced, the output waveform is determined by the Fourier transform (FT) of a spatial pattern transferred by a mask or a modulator array onto the dispersed optical spectrum. As an example, the FT optical pulse shaper is widely used for synthesis of complex femtosecond waveforms. In this geometry, the temporal profile of the output waveform is given by the FT of the mask pattern that is transferred onto the optical frequency spectrum of the pulse. FT pulse shaping was first demonstrated for use in simple pulses of tens of picoseconds in duration. Pulse shaping was then extended to the sub-100 femtosecond (fs) ($10^{-15}$ second) time scale and demonstrated highly structured waveforms using microlithographically patterned pulse shaping masks. The introduction of liquid crystal modulator arrays and acousto-optic (A/O) modulators into FT pulse shapers led to computer programmable pulse shaping, with millisecond and microsecond reprogramming times, respectively, and widespread adoption of this technique.

These shaped pulses require a very large data set and in many cases, complex learning calculations for determining the pulse shaping characteristics for a particular application. The optimal pulse for the particular application is not known in advance. Since the variation shape of the possible pulse shapes is huge, scanning the entire parameter space is impossible and as such the optimized pulse shape could not have been predicted by theory. For a pulse shaper with N pixels, one can generate $(P*A)^N$ shaped pulses, where P and A are the number of different phases and amplitudes a pixel can take. If it is assumed 100 pixels, each taking 10 different amplitude values and 100 different phase values, the number of different pulses is of order of magnitude $10^{300}$. This dataset is extremely large, therefore, while in principle, the field exists to achieve the desired photonic transformation or excitation, finding it is a great challenge. It would be desirable for a system to control ultrashort pulses with a smaller dataset and operable to generate very complex pulse shapes that are optimal for the particular application.

SUMMARY OF THE INVENTION

In accordance with the present invention, a laser system using ultrashort laser pulses is provided. In another aspect of the present invention, the system includes a laser, pulse shaper and detection device. A further aspect of the present invention employs a femtosecond laser and binary pulse shaping (BPS). Still another aspect of the present invention uses a laser beam pulse, a pulse shaper and a SHG crystal. In yet another aspect of the present invention, a multiphoton intrapulse interference phase scan (hereinafter "MIIPS") system and method characterize the spectral phase of femtosecond laser pulses. In another aspect of the present invention, a system employs electromagnetic pulse shaping design to take advantage of multiphoton intrapulse interference. Fiber optic communication systems, photodynamic therapy, functional imaging, and pulse characterization tests use the laser system with additional aspects of the present invention.

The present invention also improves the encoding-decoding functionality of pulses by adding considerably more information to each pulse by obtaining the entire phase function directly from a phase scan. Intrapulse interferences of the present invention causes self separation (for example, inherent communication signal routing address differentiation) thereby allowing use of inexpensive receivers in an asynchronous manner, in other words, without the need for synchronous detection such as by traditional autocorrelation or interferometers. The control of nonlinear optical processes using multiphoton intrapulse interference can be applied in diverse fields such as photochemistry, communications, and medicine.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 8 is a graphical illustration of the contrast ratio C that can be obtained by two-photon excitation using BPS;

FIG. 9 is a graphical illustration of a pseudo-random number generated BPS using prime numbers;

FIGS. 12a-12d a graphical illustration showing experimental results and theoretical results from BPS employed in the present invention, before and after optimization with an evolutionary learning;

DETAILED DESCRIPTION OF THE PREFERRED EMBODIMENTS

Figure 1:
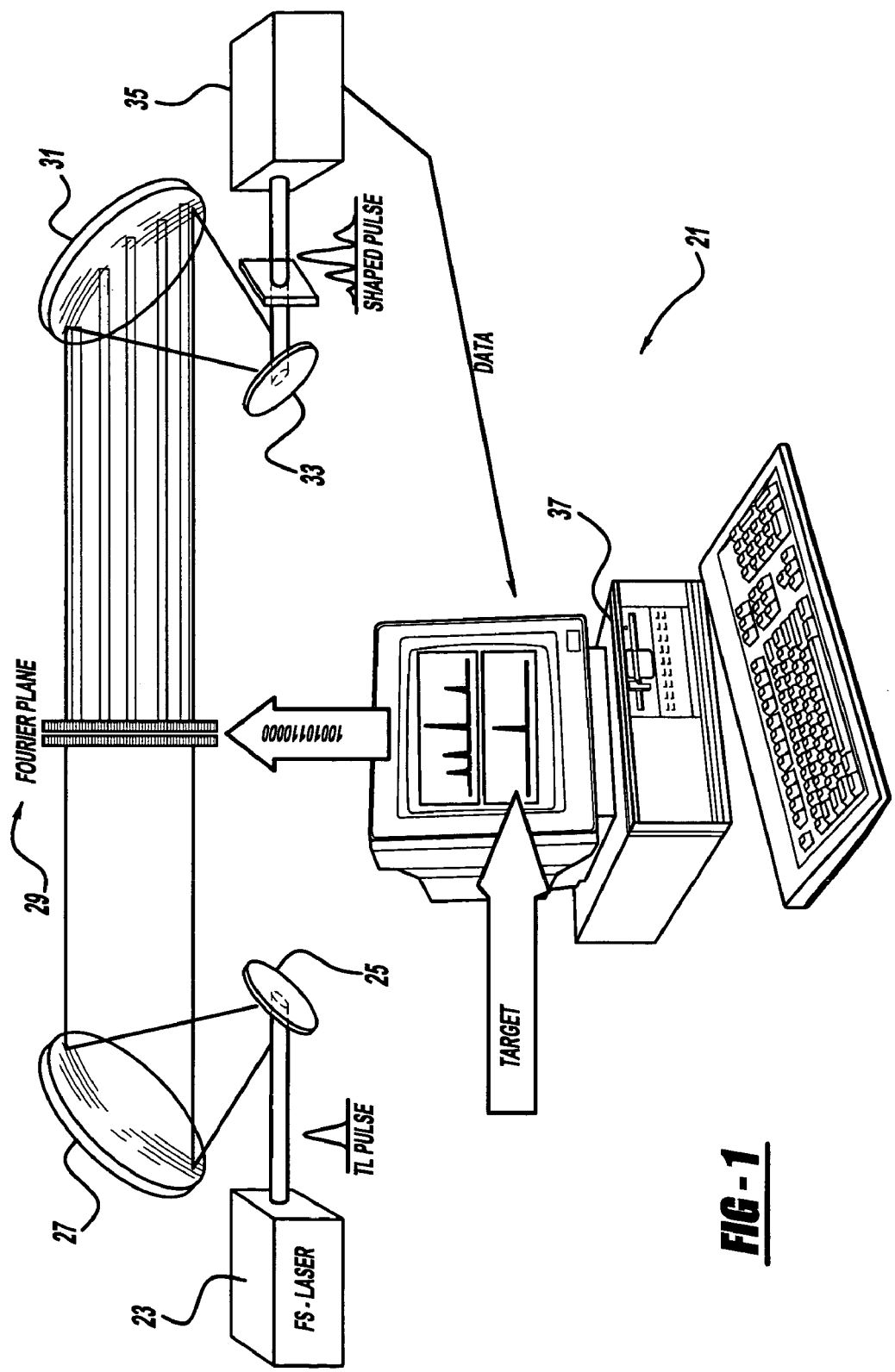
FIG. 1 is a diagrammatic view showing a preferred embodiment of a laser system of the present invention.
Figure 2A:
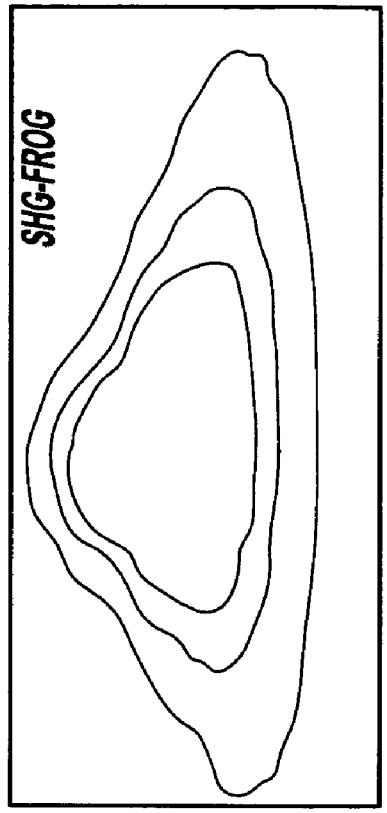
FIGS. 2a-2d illustrate phase scans from MIIPS as compared to FROG.
Figure 2B:
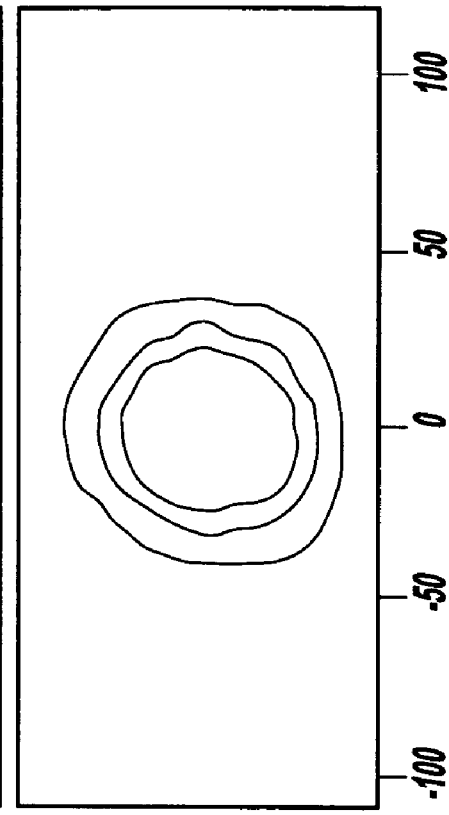
Figure 2C:
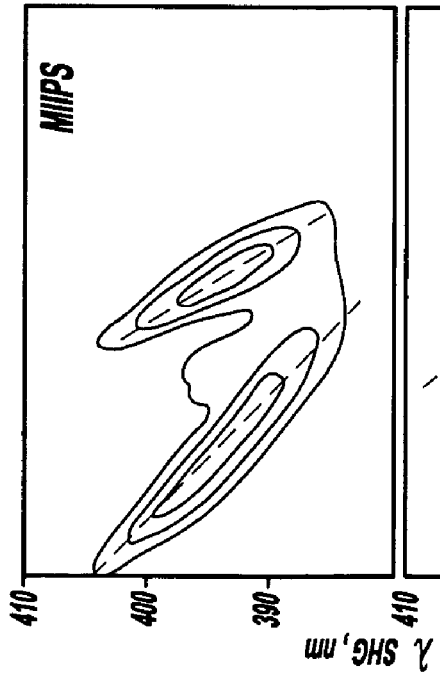
Figure 2D:
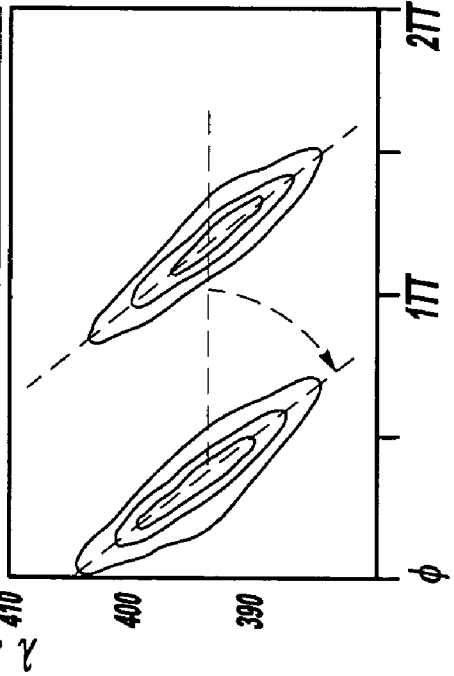
Figure 3:
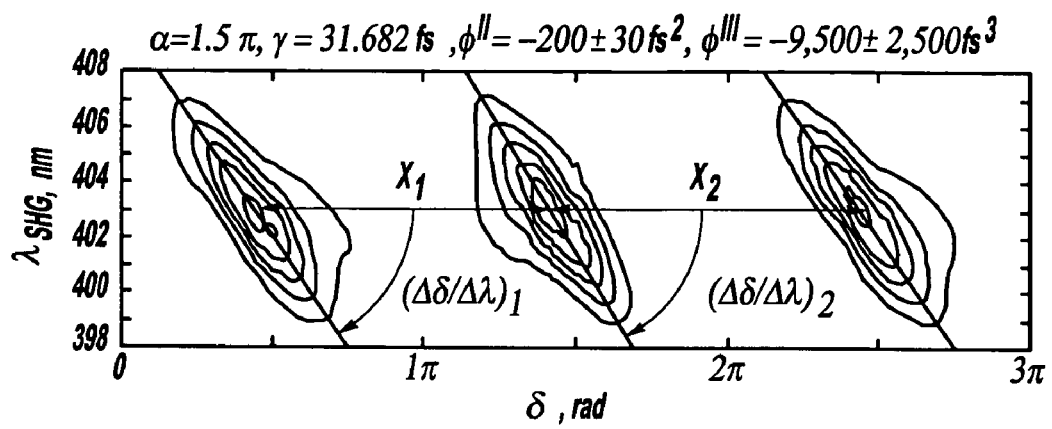
FIG. 3 is a graph showing phase scans.

The following description of the preferred embodiments is merely exemplary in nature and is in no way intended to limit the invention, its application, or uses.

The present invention provides methods and apparatus for a laser system using ultra short pulses. Pulse shaping essentially involves control over the amplitude, phase, frequency and/or inter-pulse separation. Complex pulse shaping aims to control one or more of the above-mentioned parameters in a programmable manner, such that the user has complete control. In other words, complex pulse shaping allows generation of complicated ultrafast optical waveforms according to user specification.

Coherent control is the ability to control the dynamics at various stages of a process as it evolves under the effect of a coherent source. Many of the frequencies constituting the ultrafast pulse can simultaneously excite many coherent transitions to the excited states, and a capability to manipulate them with the shaped pulses lead to the results. The term "coherent control" refers to the manipulation of molecular states coherently and thus avoids the issue of uncertainty principle for situations involving ultrafast timescales taking advantage of constructive and destructive interference.

One of the easiest available pulse modulation schemes is frequency chirping. "Chirping" essentially refers to the process of arranging the frequency components in a laser pulse with certain phase ordering. Linear "ordering" can be easily achieved by dispersing the ultrafast pulses through a pair of grating or through pulse propagation in optical fiber. Due to the uncertainty principle, this "ordering" of frequency components results in the lengthening of an otherwise bandwidth-limited ultrafast pulse. Typically, linear frequency chirping is the most often used shaped pulses, although higher-order chirp generation and some of their recent experimental uses have also been predicted.

Multiphoton Intrapulse Interference

A multiphoton intrapulse interference phase scan (hereinafter "MIIPS") system and method of the present invention characterize the spectral phase of femtosecond laser pulses. The phase across the spectrum of an ultrafast pulse can affect the multiphoton process in a number of ways. Phase can increase the pulse length and hence reduce the peak intensity of the pulse, thereby preventing saturation, a common result under high intensity excitation. Phase can also be used to synchronize changes in the electric field with intramolecular wave packet dynamics. This idea has been explored theoretically and invoked to explain some gas and condensed phase experiments. Finally, phase can be used to cause interference in the way multiple frequencies combine to achieve multiphoton excitation. This process also known as multiphoton intrapulse interference (MII) has been demonstrated under sharp resonance conditions such as transitions in isolated atoms (See Broers, B., et al., "Large interference effects of small chirp observed in 2-photon absorption," *Opt. Commun.* 1992, 91, 57; and Broers, B., et al. "Diffraction and focusing of spectral energy in multiphoton processes," *Phys. Rev. A* 1992, 46, 2749.)

The technique of MII and its application to control multiphoton processes is based on rationally designing an electric field required to achieve an articular target with a minimum number of parameters. The method is based on calculating the amplitude of the nth-order electric field and comparing it to the absorption spectrum of the molecules being controlled. This provides a strong physical understanding of the control process, which can be very useful in the interpretation of experiments where the field is optimized by computer programs based on evolutionary learning or similar methods.

Two-photon transitions can focus the energy from an ultrafast pulse into a narrow frequency distribution; just like Fresnel diffraction can be used to construct a focusing lens. Conceptually, MII takes advantage of the interference term that is associated with the phase of each frequency vi within the pulse that contributes to the multiphoton process and can enhance or what may be as valuable, suppress a multiphoton transition. The effective electric field that drives the two-photon process through the induced (nonlinear) polarization is proportional to $E^2(t)$ (in the absence of intermediate resonance at the one-photon level). Its Fourier transform $E^{(2)}(v)$ determines the frequency response at the two-photon level.

A new method known as multiphoton intrapulse interference phase scan (MIIPS) is capable of both pulse characterization and compensation of subsequent pulses. Within minutes, the pulses are characterized and compensated to yield transform-limited (TL) or user-specified shaped pulses at the sample. This capability is extremely practical and can be incorporated in any laser setup.

MIIPS is a single-beam method that does not require an interferometer (see FIG. 1). To make a precise and accurate measurement of the spectral phase using MIIPS, a known phase delay is imposed on the frequencies that make up the pulse using a calibrated pulse shaper. The pulse shaper essentially behaves as two back-to-back spectrometers. In one embodiment, the pulse is dispersed with a prism and collimated with a 200-mm cylindrical mirror. At the Fourier plane, where all the frequencies are isolated, their phases are manipulated by a computer-controlled LCD spatial light modulator (SLM). The SLM applies the reference phase function to the input pulse, and the resulting pulse is then reconstituted to the time domain by a second cylindrical mirror and prism. The SLM can be updated every pulse (presently limited to 1 kHz). The LCD has a 250-ms response time, so in principle it can be updated at 4 kHz. The output beam is analyzed by placing a 0.01-mm-thick beta barium borate crystal for second-harmonic generation (SHG) in its path, usually at the place where optimum pulses are required. The use of the second harmonic is critical to the method. In a sense, the pulse autocorrelates itself at the SHG crystal. For each reference phase function that is introduced by the computer-controlled SLM, the output spectrum from the SHG is dispersed in a spectrometer and recorded.

Pulse characterization involves the introduction of a reference phase-modulation function of the form $\phi=\alpha\cos(\gamma\Omega-\delta)$, where $\phi$ is the magnitude of the phase delay, $\gamma$ is the periodicity $\Omega$ is the frequency detuning from the carrier frequency of the pulse, and $\delta$ is the position in the spectrum at which the cosine function is equal to one. The reference phase function, with typical values $\phi=2\pi$, and $\gamma=$pulse duration, is programmed into the SLM and scanned for different values of $\delta$ ranging from 0 to $2\pi$. For each value of $\delta$, the spectrum of the frequency-doubled pulse changes, achieving a maximum in the spectral region over which the SLM compensates for the phase distortions. The MIIPS trace corresponds to the collection of spectra as a function of $\delta$ (see FIG. 2). MIIPS-generated trace of wavelength as a function of $\delta$ shows changes in the SHG spectrum of the laser pulse intensity. In general, the distance between the diagonal features is proportional to linear chirp and the angular deviation is proportional to quadratic chirp. Computer analysis of the trace is used to retrieve the spectral phase of the input pulse (a). The FROG (frequency resolved optical gating herein known as "FROG") trace clearly shows the spectral phase distortion of the pulse by its deviation from an oval (b). After three iterations of characterization and compensation, the output pulses are transform-limited as evidenced by the parallel features in the MIIPS data (c) and the oval feature in the SHG-FROG (d).

Qualitatively, the distance between the diagonal features determines linear chirp while the angle between the features determines the quadratic chirp. The full quantitative determination of the spectral phase by integration can be obtained. Once the MIIPS system has characterized the pulse and retrieved the phase distortions inherent to the pulses, it can use that information to drive the SLM such that it compensates for the distortions. The first step in compensation is to take the phase determined from the first scan and program it into the SLM with a negative sign so that it subtracts the distortions. The system carries out a new phase scan to determine the remaining spectral phase modulation (usually about 10% of the original). Typically, three such iterations will yield transform-limited pulses. Because the laser is not focused in the pulse shaper, the method can be used with pulses that are relatively high in energy. Pulses ranging from about 100 pJ to about 1 mJ and pulse durations from less than 5 to about 500 fs can be used. Once the pulses are compensated (transform-limited), the laser can be focused to produce peak intensities from about $10^{12}$ to about $10^{18}$ W/cm$^2$, depending on the input energy.

This single beam method is capable of retrieving the magnitude and sign of second and third order phase modulation (in other words, linear and quadratic chirp) directly, without iteration or inversion procedures. MIIPS achieves accurate phase retrieval from chirped ultrashort pulses. For MIIPS, no synchronous autocorrelation, beam splitting, or time delays are required because the second harmonic spectrum depends on the relative phases of all frequencies within the pulse. The amplitude of the pulse is obtained directly from a spectrometer in a communications receiver. In order to precisely determine all of the phase of all frequency components in a pulse from a fs laser 123 (see FIG. 1), a pulse shaper, such as the one described in A. M. Weiner, "Femtosecond pulse shaping using spatial light modulators," Rev. Sci. Instrum. 71, pp. 1929-1960 (2000), is employed to introduce a reference phase function designed to yield this information directly, as further described hereinafter. The shaped pulses are frequency doubled by a thin SHG crystal 507 (see FIG. 1) and the output is directed to spectrometer 503.

In addition to laboratory testing and specimen optic distortion analysis, the MIIPS system and method employing this single shot construction can also be applied to some communication situations in order to add considerably more encoded information into each pulse phase to supply additional encoding variables.

The MIIPS method is based on the principle that second harmonic generation, as well as other nonlinear optical processes, depend on the phase function $\phi(\omega)$ across the spectrum of the laser pulse. The phase function can be expanded in a Taylor series around carrier frequency $\Omega=\omega-\omega_0$ as follows:

$$\phi(\omega)=\phi(\omega_0)+\phi'(\omega_0)\Omega+\tfrac{1}{2}\phi''(\omega_0)\Omega^2+\tfrac{1}{6}\phi'''(\omega_0)\Omega^3+\ldots, \qquad [1]$$

where the first two terms provide only the relative (common) phase and a time delay, respectively. Only the third and higher terms are responsible for phase distortion. These higher terms are retrieved in MIIPS by superimposing a reference phase function on the pulse to obtain, $$\phi(\Omega)=\alpha\cos(\gamma\Omega-\delta)+\phi(\Omega) \qquad [2]$$

where the first term is the reference phase function introduced by the shaper with maximum phase amplitude $\alpha$, period $\gamma$ and the absolute position in the spectral window $\delta\phi(\Omega)$ is given by Equation 1.

The maximum SHG signal as a function of $\Omega$ is obtained when $d^2\phi(\Omega)/d\Omega^2=0$. A parameter in the reference phase function can be varied to obtain a plot from which the phase distortions ($\phi''$, $\phi'''$) can be obtained in the laser pulse. The maximum signal in a (wavelength, $\delta$) MIIPS trace describes a series of lines given by $$\delta_{max}=\delta_0+(\lambda_{max}-\pi c/\omega_0)\omega_0^2/(\pi c)\{\gamma-\phi'''/(\alpha\gamma^2\sin\delta_0)\}, \qquad [3]$$

where $\delta_{max}$ is the position where maximum SHG signal is obtained, $\delta_0=\arccos[\phi''/(\alpha\gamma^2)]$, and $\lambda_{max}$ is the position of the maximum SHG signal.

A complete data set, from which a phase function can be retrieved, consists of a series of spectra obtained as a function of the parameter δ. The resulting experimental MIIPS trace shown in FIG. 16, contains the required information to extract $\phi''$, $\phi'''$ and higher order terms as follows. First the data is fit to a series of lines which follow $\lambda_{max}(\delta_{max})$ as expected from Equation 3. The quadratic phase modulation (responsible for linear chirp) is determined directly from the distances $x_1$ and $x_2$ between the SHG maxima (see FIG. 16), according to $$\phi'' = \alpha\gamma^2 \arcsin[(x_1-x_2)/4]. \quad [4]$$

Note that the magnitude and sign of $\phi''$ are obtained directly from the MIIPS trace. Furthermore, the accuracy of the measurement can be improved for small phase distortion by decreasing the reference phase function parameters $\alpha\gamma^2$.

Figure 16:
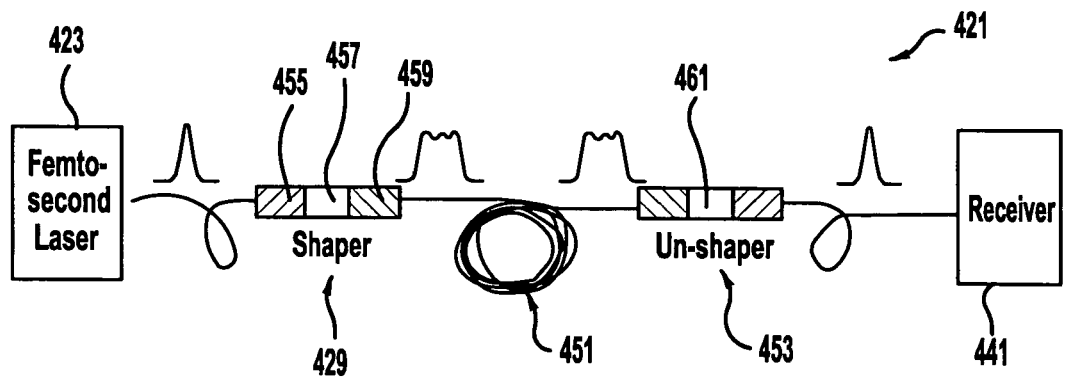
FIG. 16 is a diagrammatic view showing an another preferred embodiment of the invention applied to communications.
Figure 17:
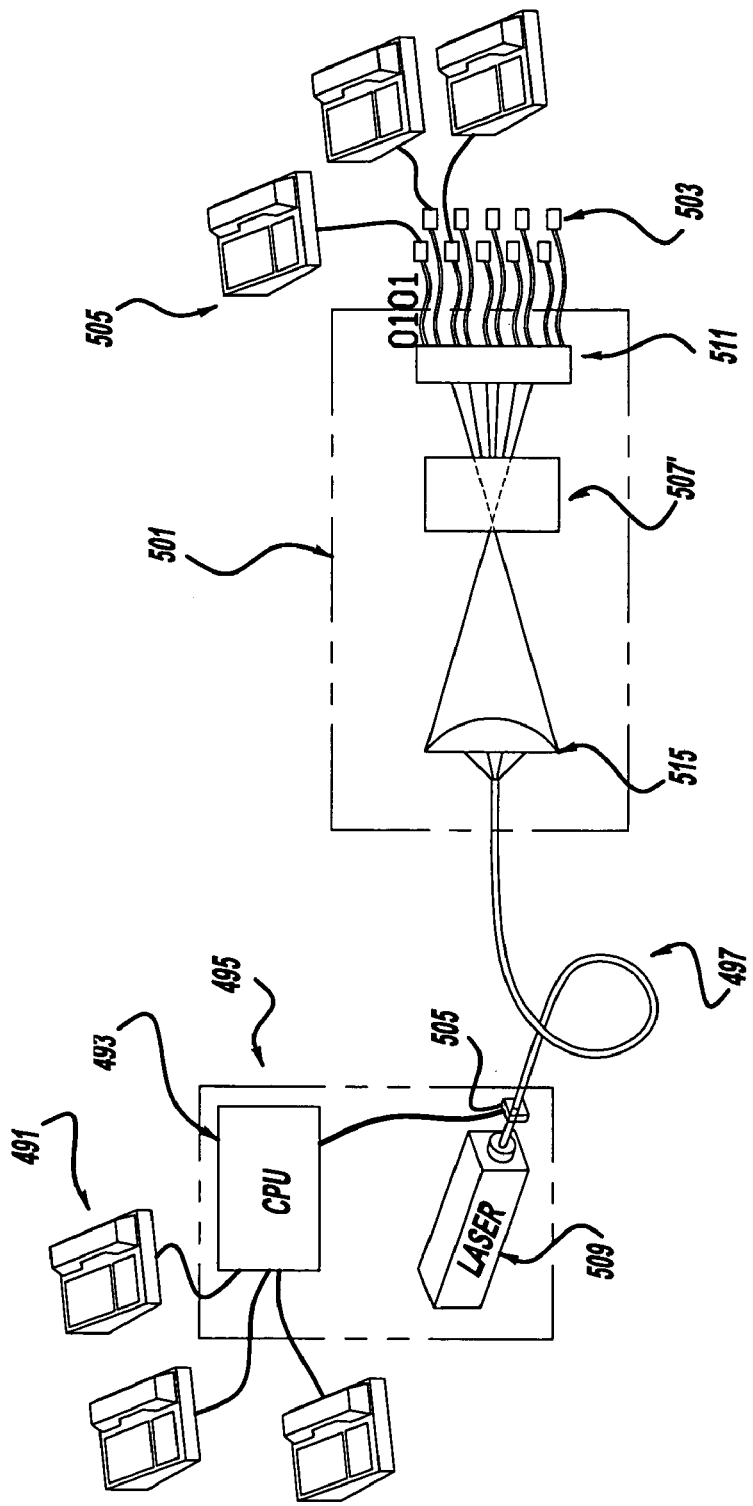
FIG. 17 is a diagrammatic view showing another preferred embodiment of the present invention applied to communications.

The cubic phase modulation (quadratic chirp) is determined by the slope $\Delta\delta/\Delta\gamma$ that the maximum SHG features make in the λ δ plane. Analytically, cubic phase modulation is given by $$\phi''' = 0.5\alpha\gamma^2\pi c/\omega_0^2 \cos[(x_1-x_2)/4]\{(\Delta\delta/\Delta\gamma)_1-(\Delta\delta/\Delta\gamma)_2\}, \quad [5]$$

where the slopes are measured in $nm^{-1}$ (see FIG. 16). Higher order phase distortions, such as self-phase modulation and quadratic phase components can be obtained from the curvature of the line defined by the maximum SHG response. The MIIPS can be programmed to find the phase distortions on the laser pulses directly by integration and to introduce a compensation phase function that eliminates the distortions. This mode of operation can be used to find arbitrary phase deformations and yield transform limited pulses, which in a MIIPS scan look like straight parallel lines separated by π. The fit to the experimental data shown in FIG. 16-17C is given by Equation 3, and the phase parameters are extracted with Equations 4 and 5.

Figure 13:
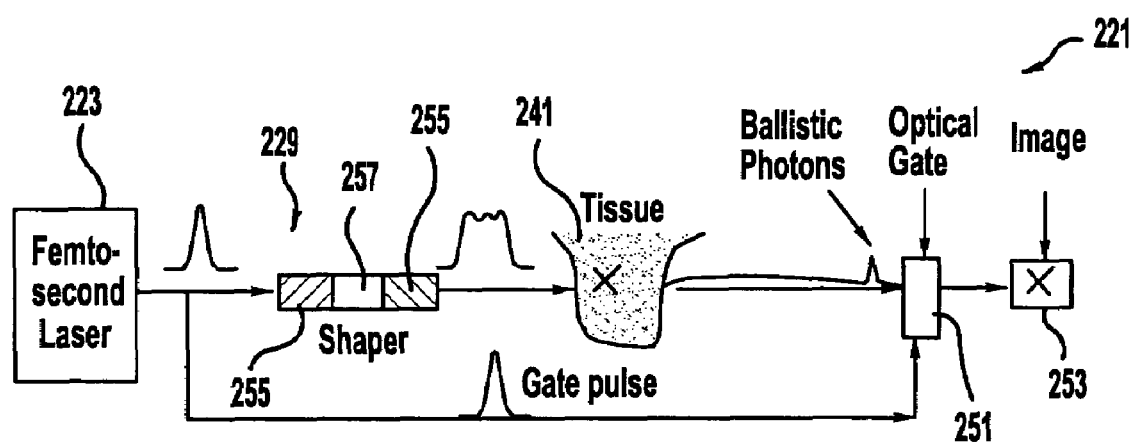
FIG. 13 is a diagrammatic view showing embodiments of the present invention applied to optical coherent tomography and photo dynamic therapy.
Figure 14:
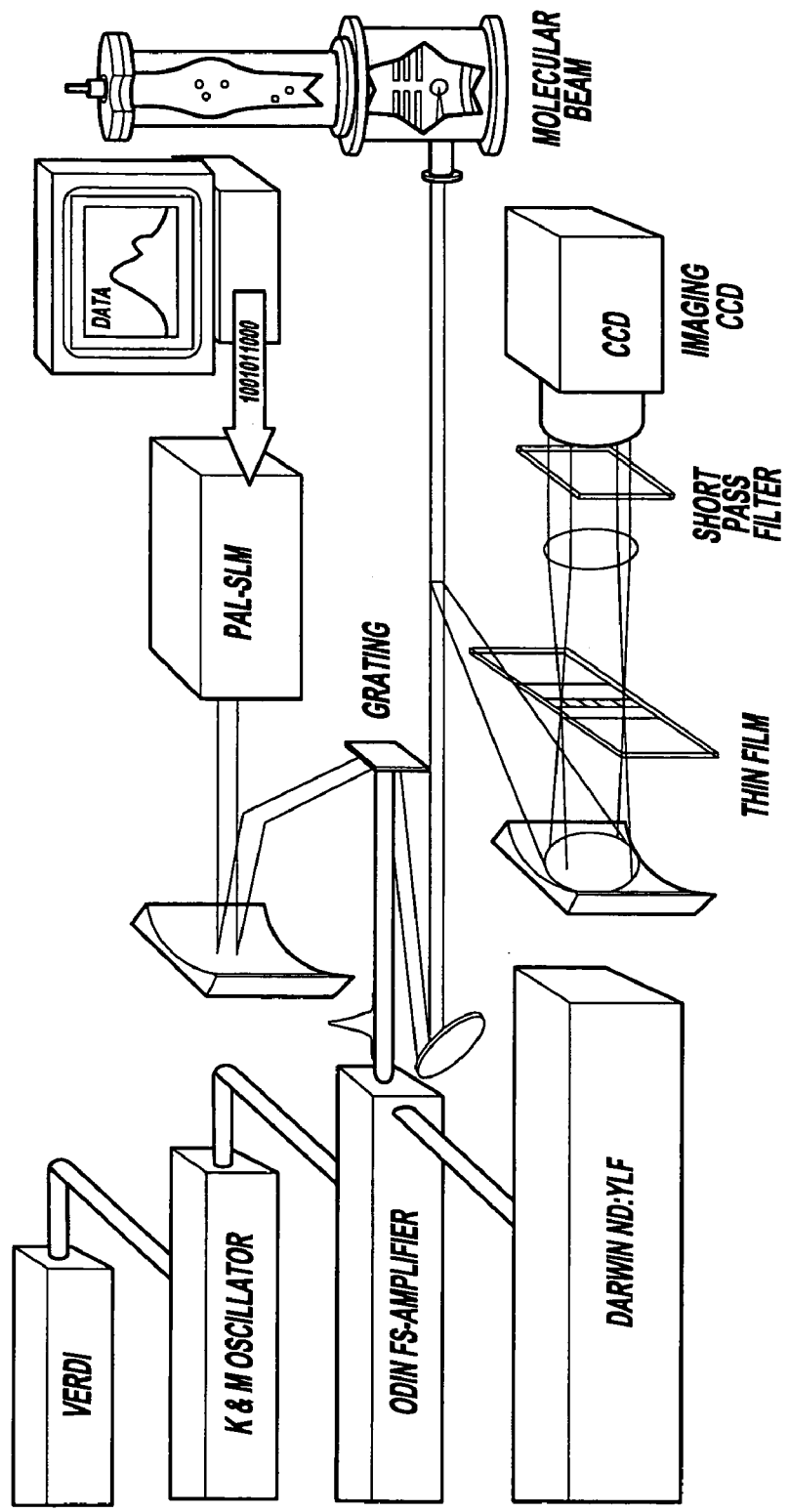
FIG. 14 is a diagrammatic view showing another preferred embodiment of the invention applied to spectroscopy.
Figure 15:
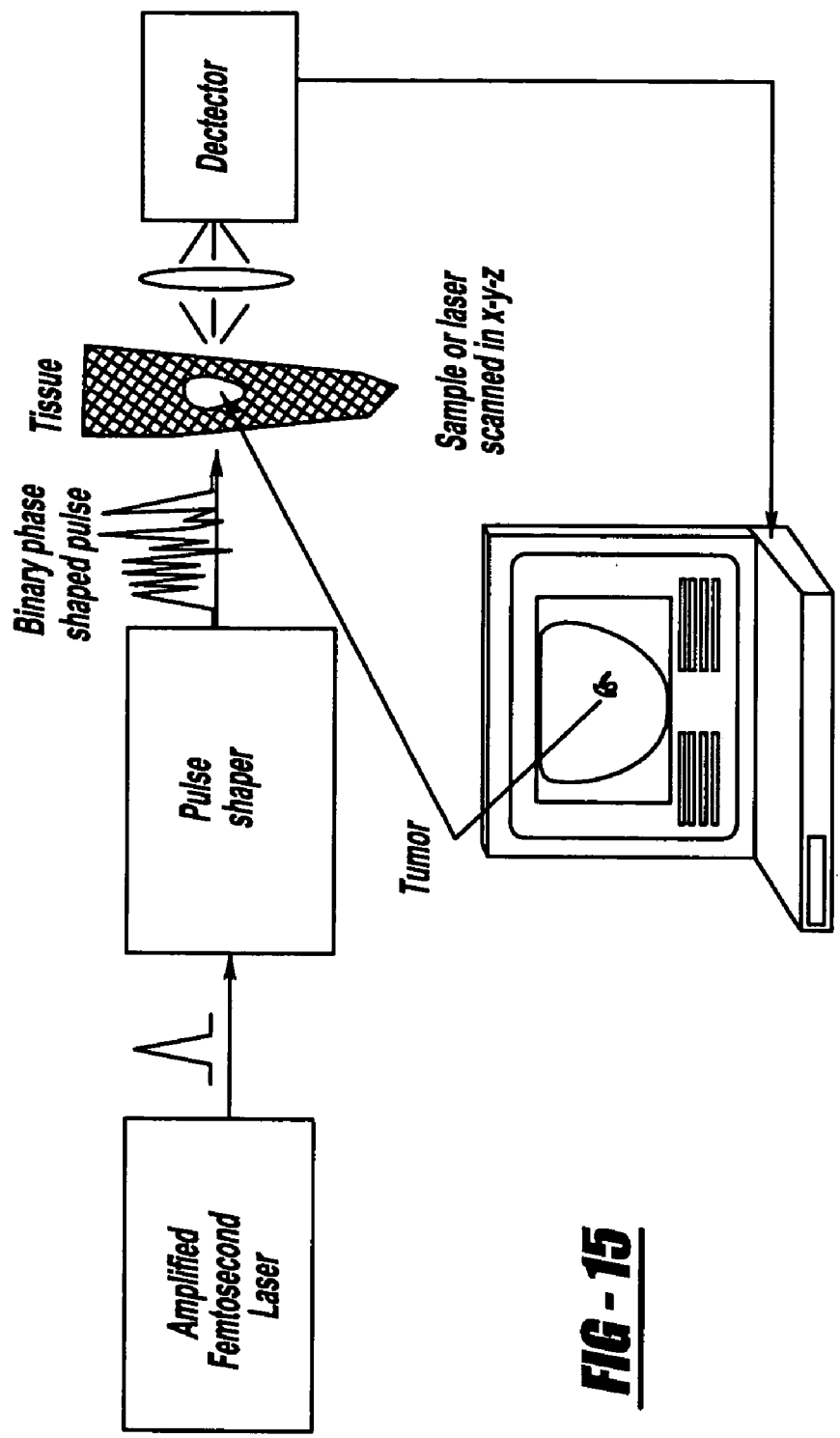
FIG. 15 is a diagrammatic view showing a preferred embodiment system of the present invention using BPS applied to optical coherent tomography and photodynamic therapy.

The version of MIIPS illustrated in FIG. 15 uses a thin SHG crystal 507, spectrometer 503, pulse shaper 129 and a femtosecond laser 123. A fs laser pulse is preferred but, for test data disclosed herein, 50 fs pulses from a regeneratively amplified Ti:Sapphire laser are employed wherein the pulse energy is attenuated down to ~5 μJ. For the test data herein, A 0.3 mm βBBO type I crystal is used for SHG 507 and the output is attenuated and directed to spectrometer 503 with a cooled CCD detector 511. System 121 further has a redirecting mirror 513, two quartz cylindrical lenses 515 (200 mm focal length, the upstream one for focusing and the downstream one for collimating). For the tests, a spatial light modulator was used for pulse shaper 129 consisting of two 128 LCD elements (which can be obtained from CRI Inc. as model number SLM-256). For the test, the pulse shaper is carefully calibrated to provide accurate phase delays (better than one degree) with no changes to polarization or amplitude. The phase distortions used to obtain the data are generated at the pulse compressor after regenerative amplification. Referring now to FIGS. 13 and 14, self-ultrafast switching is based on pulse phase modulation in pulse shaper 505, a thin SHG crystal 507 causing multiphoton intrapulse interference, dispersive optics 523, and CCD camera detector 511. The simplicity and accuracy of this method make it practical for the evaluation of laser pulses close to transform limit and for the evaluation of phase distortion from optical elements.

Additional information about MII and MIIPS is disclosed in U.S. Patent Publication No. 2003-0099264 entitled "Laser system using ultrashort pulses" invented by Dantus, et al., and PCT Publication No. WO 02061799 entitled "Laser system using ultrashort pulses" invented by Dantus, et al.; I. Pastirk, J. M. Dela Cruz, K. A. Walowicz, V. V. Lozovoy, M. Dantus, "Selective two-photon microscopy with shaped femtosecond pulses," Opt. Express 11, 1695-1701 (2003); J. M. Dela Cruz, I. Pastirk, V. V. Lozovoy, K. A. Walowicz, M. Dantus, "Multiphoton intrapulse interference 3: Probing microscopic chemical environments," J. Phys. Chem. A 2004; Lozovoy V. V., Pastirk I., Walowicz K. A., Dantus M., "Multiphoton intrapulse interference II: Control of two- and three-photon laser induced fluorescence with shaped pulses," J. Chem. Phys. 118 (7): 3187-3196 (Feb. 15, 2003); and Walowicz K. A., Pastirk I., Lozovoy V. V., Dantus M., "Multiphoton intrapulse interference 1: Control of multiphoton processes in condensed phases," J. Phys. Chem. A 106 (41): 9369-9373 (Oct. 17, 2002); all of the patent applications of which are incorporated by reference herein.

Multiphoton intrapulse interference is not just about focusing the energy. The goal is to determine the field that the molecules experience. The control of nonlinear optical processes, using multiphoton intrapulse interference can be applied in diverse fields such as photochemistry, communications, and medicine.

Figure 6A:
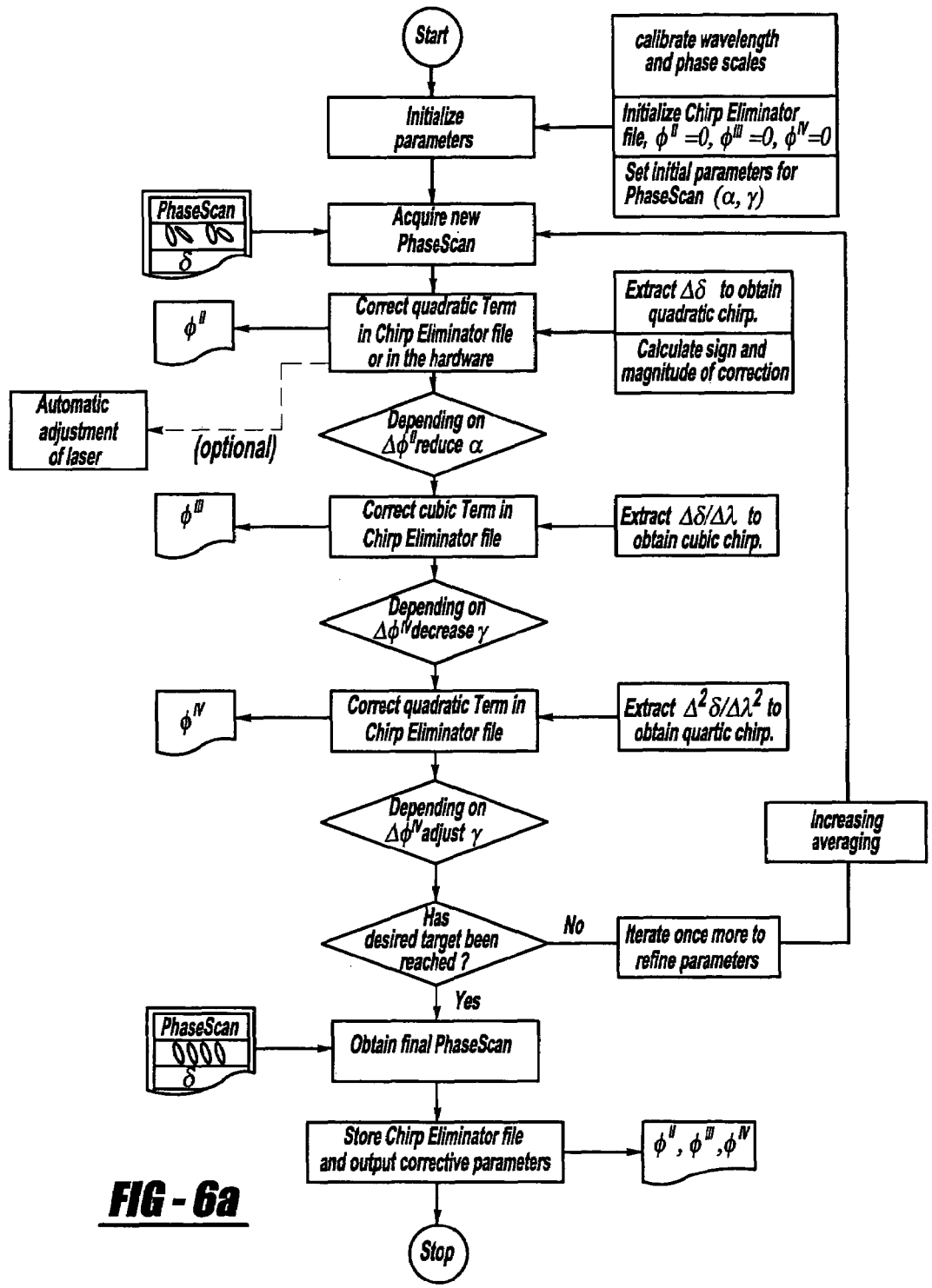
FIG. 6a is a flowchart of computer software that is used in some of the preferred embodiments of the invention.

The present invention provides a system and method to characterize the spectral phase of femtosecond pulses. This single beam method is capable of retrieving the magnitude and sign of linear and quadratic chirp with high resolution. Pulse retrieval is based on analytical expressions that yield the phase distortion, without iteration or inversion procedures. Linear and quadratic chirp values, and to some extent cubic chirp values, are important because there are knobs on the laser that can be used to correct for this distortion by mechanically adjusting the grating spacing in the laser beam amplifier compressor. The method can be used with very short pulses. This adjustment can be automatically controlled with the computer controlled software as disclosed in FIG. 6a. The method is very versatile, and can be used with high or very low intensity pulses for any wavelength for which low cost, off-the-shelf SHG crystals exist. MIIPS can also be used by obtaining third or higher order harmonics in gases. The maximum signal will also agree with Equation 35, making the method useful for the characterization of pulses in wavelength regions for which SHG crystals are not available. In summary, uses of MII and MIIPS are as follows:

- MII can be used to make self-switching pulses as long as they undergo one non-linear optical process, such as SHG, sum frequency generation, difference frequency generation or four-wave mixing;
- MIIPS can be used to allow automated laser optimization, specifically quadratic and cubic phase distortions;
- MIIPS can be used for pulse characterization of arbitrary phase distortions;
- MIIPS can be used to measure the phase modulation induced by optical elements and similarly it can be used to measure the thickness of a substrate;
- MIIPS can be used for decoding information (address and/or message) stored in the phase;
- Shapers operating to optimize the MII phenomenon can encode self-decoding messages;
- MII can be used to prevent three photon damage of DNA from fs pulses; and
- MII can be used to optimize the selective activation of PDT agents specifically at a particular depth, avoiding collateral damage.

Figure 6B:
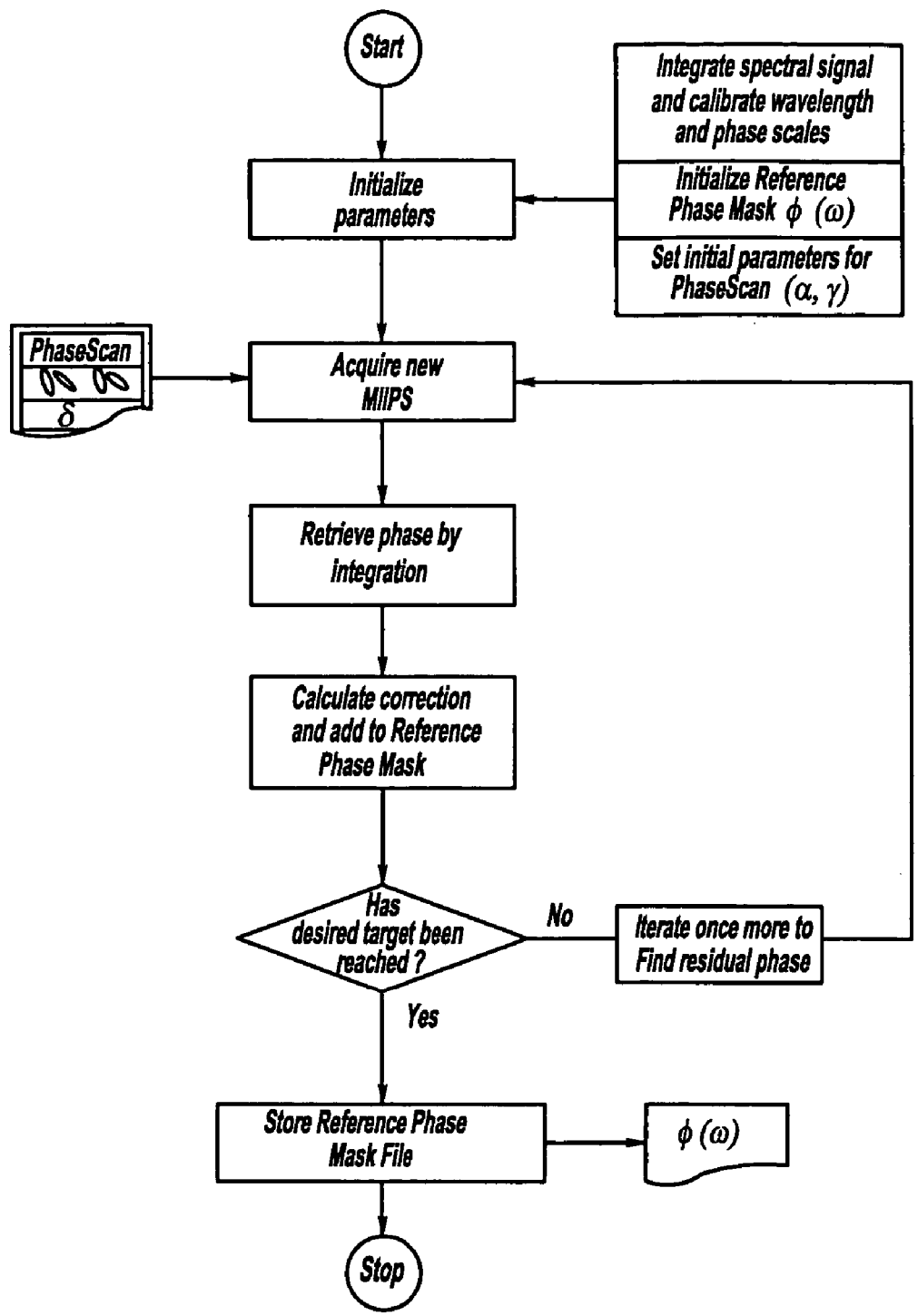
FIG. 6b is a flow chart of computer software that is used in an automated spectral phase determination of some of the preferred embodiments of the present invention.

FIG. 6b is a flow chart showing an automated pulse chirp determination for arbitrary smooth phase distortions. This method is based on the use of a pulse shaper and obtaining a phase scan, wherein the spectrum of the SHG is a function of phase parameter δ for $\phi(\omega)=\alpha \cos(\gamma\omega+\delta)$. This method is non-iterative and it directly obtains the desired values without evolutionary learning calculations. Therefore this method is very stable. This method does not depend on overlap between two pulses in space and time. Moreover, the pulse analyzes itself in a thin SHG crystal.

Second—Harmonic Generation with Powders

Chemical powders, adhered onto transparent quartz carriers, are employed in place of thin SHG crystals. The powder embodiment is presently preferred to significantly reduce cost in high energy (for example, one nanojoule or greater) applications such as for MIIPS, nonlinear optical characterizations and FROG analysis. The chemical powder is preferably Potassium Dihydrogen Phosphate (KDP or KD*P) or Beta Barium Borate, which is glued onto a glass, microscope slide using a silicone-rubber or cyanoacrylate ($C_5H_5NO_2$) adhesive. Type I phase matching is used. The power particle size is preferably between about 0.5 to 20 microns, depending on the focusing length, intensity of the laser and the sensitivity of the detector. For microscopy, even smaller particles can be employed as long as a very sensitive detector is used. Furthermore, the powder approach is advantageous by having large variety of random crystal orientations therein which creates improved average results for laser pulses shorter than 20 fs.

Pulse Shaping System

The first preferred embodiment of a laser system 21 using ultrashort laser pulses of the present invention is generally shown in FIG. 1. System 21 includes a femtosecond laser 23, an upstream grating 25, an upstream concave mirror 27, a laser beam pulse shaper 29, a downstream concave mirror 31, a downstream grating 33, a detection device 35, and a personal computer 37. Personal computer 37 has a microprocessor based electrical control system, memory, an output screen, a data storage device, an input keyboard, and a removable disk. More specifically, the detection device is a spectrometer 39. Bursts or pulses of a laser beam 43 are emitted from laser 23, through the optics 25, 27, 31 and 33, as well as through pulse shaper 29 for detection and sensing by spectrometer 39 for further evaluation, analysis, comparison and subsequent control by personal computer 37.

The laser is preferably an ultra-short femtosecond laser that can deliver high peak intensity (with a typical peak greater than $10^{10}$ watts/cm$^2$) which preferably emits laser beam pulses of less than 100 femtosecond duration, and more preferably at or less than 50 femtoseconds, and for certain applications even more preferably at or less than 10 femtosecond duration, for each pulse burst or shot. The intense optical pulses that are required to modify material are formed in a Kerr-Lens mode locked titanium sapphire oscillator. Such lasers are capable of producing hundreds of nanometers of coherent bandwidth, although only about 50 nm are typically used. The output may be amplified in a 1 kHz regenerative chirped pulsed amplifier. The output pulse is typically 100 fs long with a central wavelength of 800 nm and total pulse energy of 0.1 to 1 mJ. Preferred lasers include: the Kapteyn and Murnane femtosecond laser oscillator, which can produce less than 15 fs pulses at 100 MHz; the Hurricane model from Spectra Physics Inc., which is diode pumped and gives 0.8 mJ per pulse with sub-50 fs pulses at 1 kHz; and the CPA-2001+ model from Clark-MXR Inc., which gives 1.3 mJ per pulse with sub-150 fs pulses at 1 kHz, pumping a Clark-MXR Inc. non-collinear parametric amplifier (hereinafter "NOPA") which produces 0.2 mJ per pulse, and is capable of generating sub-20 fs pulses. This NOPA system can even produce pulses between 10 fs and 4.5 fs.

A Fourier plane pulse shaper is preferably used with the present invention for the transmissive construction illustrated with this embodiment. Ultra-fast laser pulses contain from one to fifty optical cycles, and last only a few femtoseconds. This is much faster than most current electronics and therefore shaping with fast time gates is very difficult. On the other hand, because of the uncertainty principle, the optical spectrum spans tens to hundreds of nanometers. Such a large bandwidth is relatively easy to measure and to filter, and there are several techniques to shape the spectrum in the frequency domain, and thereby shape the temporal pulse upon recompression.

In order to access the frequency domain and the individual frequency components that comprise the pulse, a geometric arrangement is employed, using two back-to-back spectrometers. The spectrometers are especially designed to introduce no net temporal dispersion: that is, all colors pass through the spectrometers within the same amount of time. The first spectrometer (including grating 25 and mirror 27) spreads the unshaped pulse spectrum along a line according to its dispersion function $y(\alpha)$. The light intercepts spatial amplitude and phase mask pulse shaper 29 at this point. The mask output then forms the entrance to a second spectrometer (including grating 33 and mirror 31) which recombines the colors into a single shaped pulse.

The heart of pulse shaper 29 is the programmable 256 pixel liquid-crystal mask (consisting of two overlapping 128 pixel liquid crystal arrays) that is placed at the Fourier plane. For the applications envisioned herein, the mask must be capable of shifting the phase of individual frequencies. For alternate embodiment pulse shapers, a different electronically programmable mask that is capable of controlling phase has been demonstrated: a liquid crystal display (hereinafter "LCD"), an acousto-optic modulator (hereinafter "AOM"), a deformable mirror, and a permanently deformed mirror. A LCD pulse shaper can be obtained from CRI Co. and has a modulator electronic driver.

Figure 23:
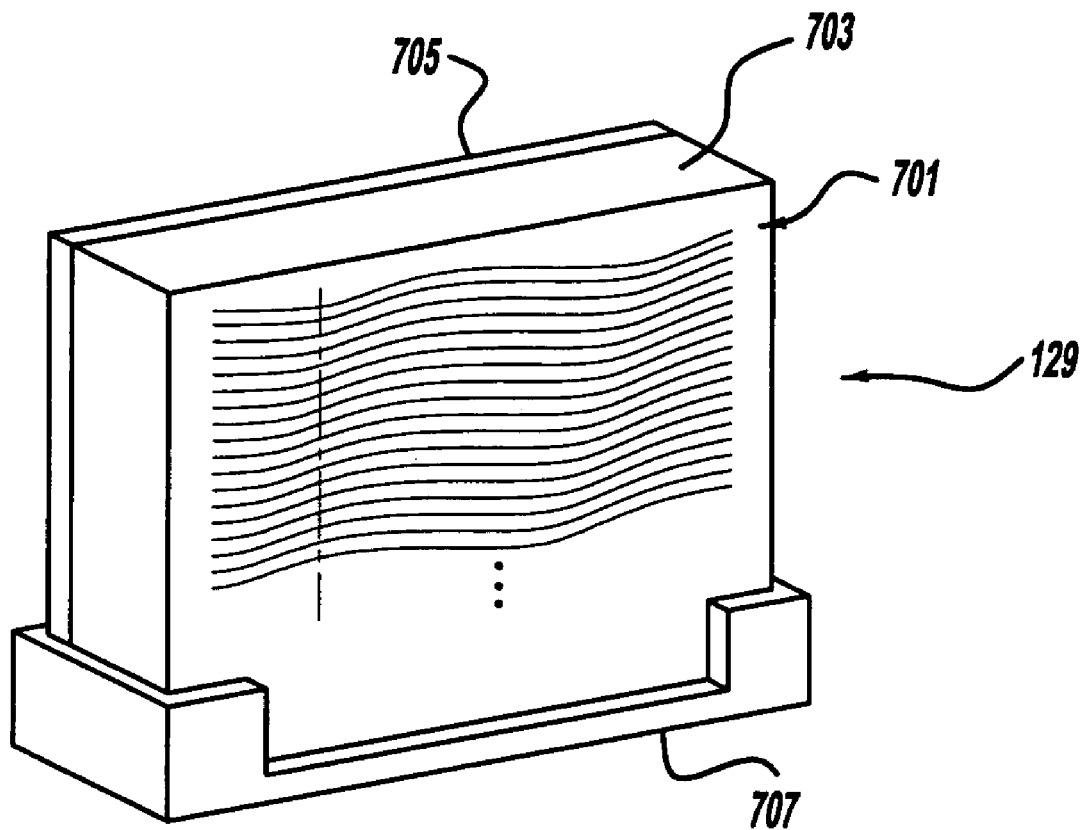
FIG. 23 is a perspective view showing a preferred embodiment of a fixed, two dimensional shaper employed in the present invention.

The AOM consists of an anti-reflection coated Tellurium Dioxide (TeO$_2$) crystal with a piezo electric transducer glued onto one end. The central frequency of the acoustic wave is $\alpha c/2\pi=200$ MHz. The acoustic velocity vs in the crystal is 4.2 km/s and the light pulse spends less than 10 ps in the crystal, so the acoustic wave moves less than 0.002 $\lambda$ acoustic during the transit of the light field through the crystal. Since the acoustic wave is essentially frozen as the optical pulse travels through the crystal, the complex amplitude of the acoustic wave traveling through the crystal in the y direction, $A(t)\cos \alpha ct = A(y/vs)\cos \alpha ct$, is mapped onto the optical field $E(\alpha)$ as it passes through the AOM. If some of the dispersed optical field encounters a weak acoustic wave, that frequency is attenuated; if the acoustic wave carrier is shifted by phase angle ø, that phase shift is imposed on the optical field. This pulse shaper has a total efficiency of about 20% including the diffraction efficiency of the AOM and the diffraction efficiency of the gratings. The diffracted light is used and the undiffracted "zero order" beam is blocked, to allow full modulation of both amplitude and phase in the shaped beam. The shaped beam than has the form $$E_{shaped}(\omega)=E_{input}(\omega)\times a(\omega)\times e^{i\phi(\omega)t} \quad [6]$$

where $a(\omega)e^{i\phi(\omega)}=A[y(\omega)/v_s]$; $\alpha$ is the frequency, and e is a constant. Fixed pulse shaping optics, such as chirped mirrors, can also be employed as will be discussed further hereinafter with regard to FIG. 23.

The transform-limited pulses (hereinafter "TL"), having all their frequencies in phase, are fed into the pulse shaper where curved mirror 27 focuses the spectrum onto Fourier plane 29. Changes in the phase ø and amplitude A of the spectral components indicated by the computer are used to tailor the laser pulse before reconstruction with second curved mirror 31 and grating 33. Once compressed, the shaped pulse is directed to spectrometer 39 for evaluation. The Fourier transform relationship between the time and the frequency domain allows us to calculate the necessary mask to create a certain shaped pulse. These calculations are based on $$f(v) = \frac{1}{2\pi} \int_{\infty}^{0} f(t) e^{i2\pi vct} dt \qquad [7]$$

and $$f(t) = \int_{\infty}^{0} f(v) e^{-i2\pi vct} dv \qquad [8]$$

where v is the frequency in wave numbers, t is the time, and c is the speed of light.

In this embodiment, the phase and amplitude masks of the pulse shaper are controlled by the computer wherein the laser pulse shape takes a dynamic role. The microprocessor within personal computer 37 will then control laser 23, receive an essentially real time feedback input signal from spectrometer 39, and then perform calculations, comparisons and evaluations, and possibly automatic variation of subsequent pulse shapes. These automated steps can be substituted with manual user calculations and decisions if desired based on personal computer outputs.

Figure 5:
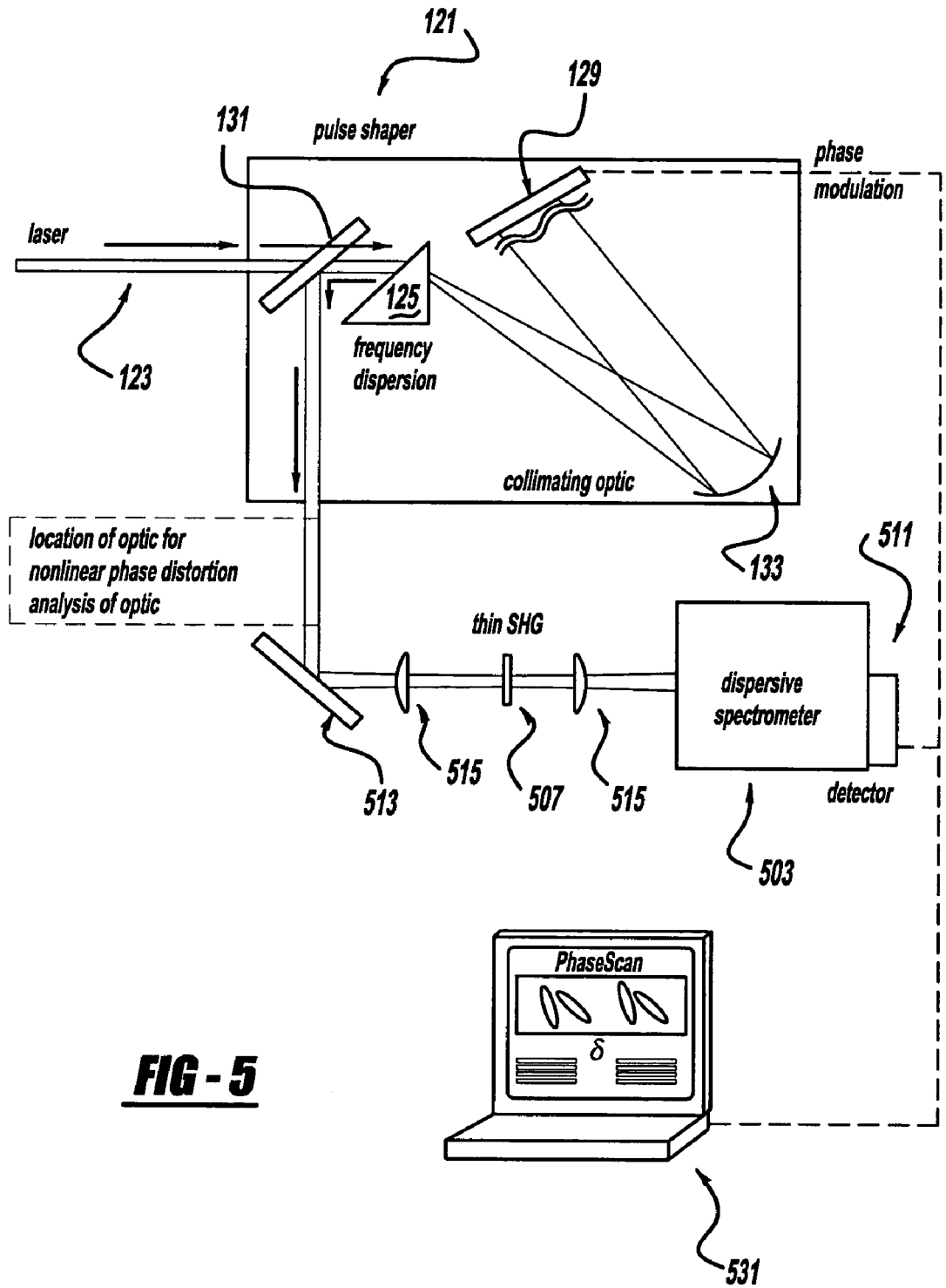
FIG. 5 is a diagrammatic view showing a preferred embodiment of the present invention that employs MIIPS.

As applied to all of the applications herein, selective control of one and multiphoton processes in large molecules, including proteins, is possible using a simple pulse shaping method that is based on taking maximum advantage of the multiphoton intrapulse interference caused in short pulses with large bandwidths. The results show an extraordinary level of control that is robust and sample independent, with contrast ratios near two orders of magnitude (clearly visible with the naked eye). Such large contrast ratios allow for more precise cancellation control of undesired photons and other laser beam characteristics, such that nonlinear transitions induced by each pulse are controlled. Because simple phase functions can be incorporated into a passive optical component such as mirror 129 (see FIG. 5), these applications do not require the complexity and expense of computer controlled pulse shapers after initial set up, although systems can still be employed.

A fs-pulse shaper arrangement can be used to achieve background free functional imaging (pH, Na or Ca concentration gradients, electric fields, charge, fluorescent probes, nanoclusters, or quantum dots, chemical composition) by taking advantage of the selective excitation afforded by multiphoton intrapulse interference. For example, A. H. Buist, et al., "Probing microscopic chemical environments with high-intensity chirped pulses," Optics Letters 24, 244-246 (1999). Buist, et al., showed that linear chirp can be used to crudely distinguish the pH environment of a pH-sensitive dye. With phase modulation, and specifically taking advantage of multiphoton intrapulse interference, the present invention can achieve much more sensitive pH sensitivity with a greater number of pH-sensitive dyes. Using the same principle, dyes that are sensitive to sodium, calcium or other chemical gradients including also charge and can also be probed selectively. Alternatively, multiple probes such as dyes, nanoclusters or quantum dots can be selectively excited through two- or three-photon excitation.

Binary Phase Shaping

In the low intensity regime, laser control is dominated by interference of different nonlinear optical pathways connecting the initial and final states. The challenge is finding the proper phase for each frequency within the pulse to achieve constructive interference at the desired pathway and destructive interference elsewhere. Consider two-photon excitation of fluorescent probes, as used in two-photon microscopy, as the target for optimization and envision two chromophores with different two-photon absorption spectra. The goal is to achieve selective excitation by "focusing" the energy available at a specific region of the two-photon spectrum, while minimizing the energy outside of the desired spectral window as shown in FIG. 8.

The broad bandwidth second harmonic spectrum from transform-limited pulses is represented by a Gaussian curve (thin line). The objective is to introduce phase modulation to cause the two-photon spectrum to be intense only inside the window defined by frequency $2\omega_c$ and width W, and to minimize the background B outside the window. The contrast ratio C is defined as the intensity inside the window divided by the intensity of light outside the window The phase between photons of different frequencies takes only two values preferably 0 or preferably π to maximize or minimize a given pathway. Any two values whose difference is π work equivalently well. Based on the theoretical and experimental confirmation of this, the method is defined as binary phase shaping (BPS). In a preferred embodiment, BPS is used to solve the problem of selective multiphoton excitation with ultrashort laser pulses.

In order to control two-photon excitation, one needs to control the non-linear power spectrum of the laser $E^{(2)}(\omega)$, which can be measured by obtaining the second harmonic spectrum generated using a thin second harmonic generation (SHG) crystal. Selective two-photon excitation is possible when one is able to tune the narrowed non-linear power spectrum to optimize excitation of one chromophore versus another.

The effect of spectral phase modulation on SHG has been studied by a number of groups and can be divided into broad and narrow phase matching bandwidth. Sinusoidal phase modulation, a common function used for laser control, cannot produce contrast ratios greater than 0.5, and as the window is tuned away from the central frequency the contrast drops below 0.1.

Consider two phases, 0 and π, then the symmetry becomes clear. To maximize the SHG intensity at a frequency $2\omega_C$, the spectral phase needs to be symmetric or antisymmetric about $\omega_C$, such that the frequencies interfere constructively. To minimize the background intensity at all other frequencies, the spectral phase must be asymmetric with respect to all other frequencies away from $\omega_C$, so that destructive interference is maximized. As described by others, binary phase filters masks or deformable mirrors or SLMs produce waveforms with symmetrical intensities only. (See A. M. Wiener, "Femtosecond pulse shaping using spatial light modulators," Rev. Sci. Instrum., Vol. 71(5), page 1934.) In another preferred embodiment, prime numbers are used to generate the quasi-random phase changes required. The mask that is used to modulate the pulses is shown in FIG. 9, and is designed for a 128-pixel modulator. As shown in FIG. 9, a phase mask proposed based on the symmetry requirements of the problem, using the quasi-randomness of prime numbers. This mask is reflected about pixel 64 to obtain the values of pixels 65-128, and is designed to obtain a narrow second harmonic signal at the center of the spectrum, for example. Other preferred embodiments employ a 128-pixel SLM and still other embodiments employ a SLM with greater than 256 pixels.

A titanium-sapphire oscillator which can be obtained from K&M Labs laser system capable of generating pulses as short as 10 fs after a double pass prism compressor is preferably employed. The spectral phase of the pulse is tailored using a computer-controlled pulse shaper. Preferably, the pulses are centered near 800 nm. The spectral phase of each pulse was corrected using the MII phase-scan (MIIPS) method, which compensates phase distortions to obtain transform-limited (TL) pulses. The binary phase was introduced as an addition to the compensation phase.

The shaped laser pulses, with energy ~0.5 nJ per pulse and 87 MHz repetition rate, are focused mildly, to a spot size of ~100 microns in diameter, on a 20 micron thin beta barium borate ($\beta$BBO) type I SHG crystal. The frequency-doubled light was collected with an optical fiber and dispersed on a compact spectrometer, preferably obtainable from Ocean Optics.

Figure 10A:
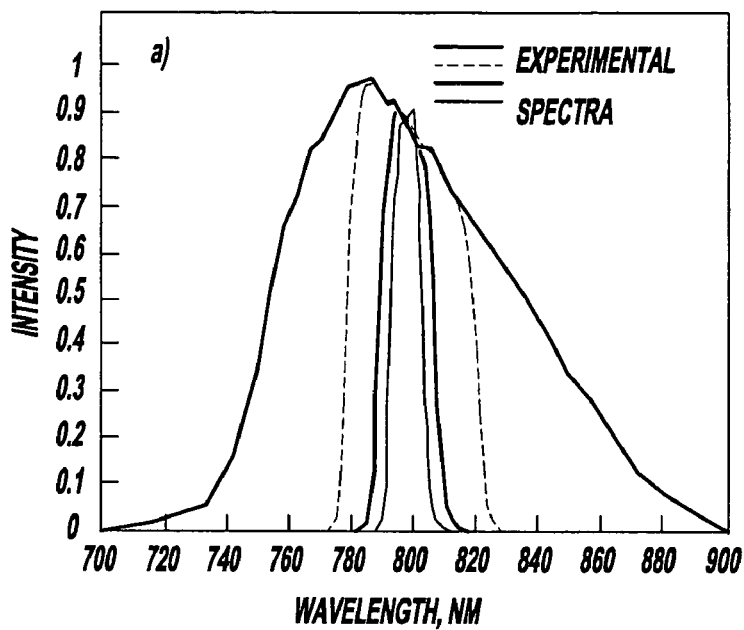
FIGS. 10a and 10b demonstrate experimental results and theoretical predictions of a method based on amplitude masking not using BPS.
Figure 10B:
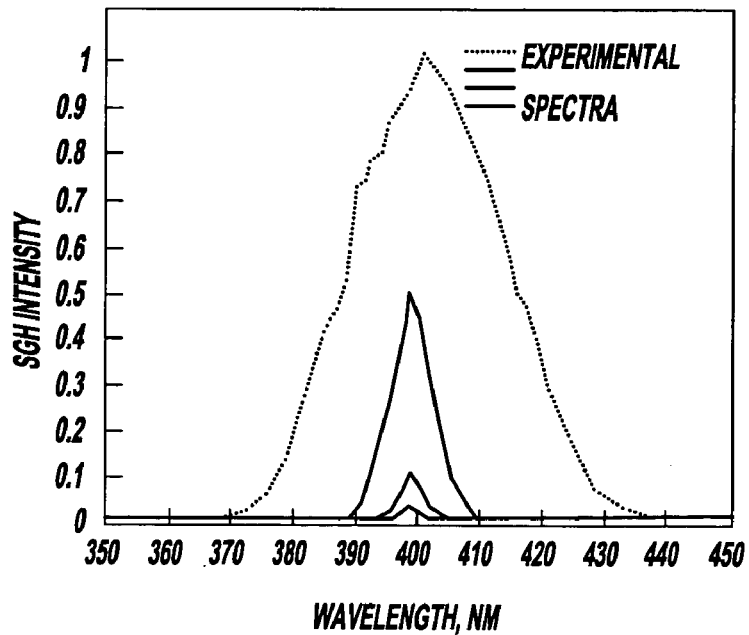

Before introducing phase modulation, spectral amplitude restriction was considered and the spectrum of the laser was narrowed using a slit at the Fourier plane. The resulting spectra are shown in FIG. 10a. In FIG. 10b the SHG intensity obtained after amplitude restriction is shown and note that the energy inside the window depends on the spectral width squared. For a spectral width of 10% of the available bandwidth, amplitude restriction produces 100 times less second harmonic intensity than TL pulses. Although the contrast ratio for this case is favorable, the low intensity obtained at the desired wavelength makes this method experimentally impractical.

Figure 4A:
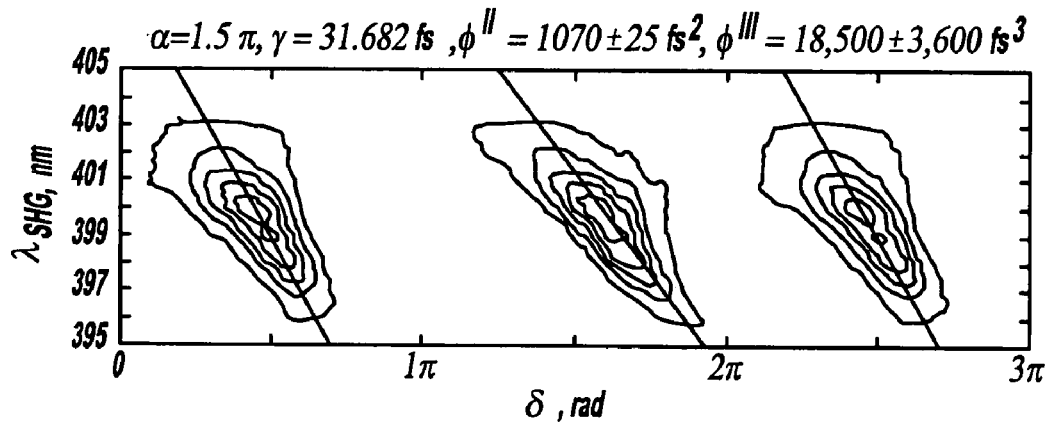
FIGS. 4a-4c are graphs showing phase scans.
Figure 4B:
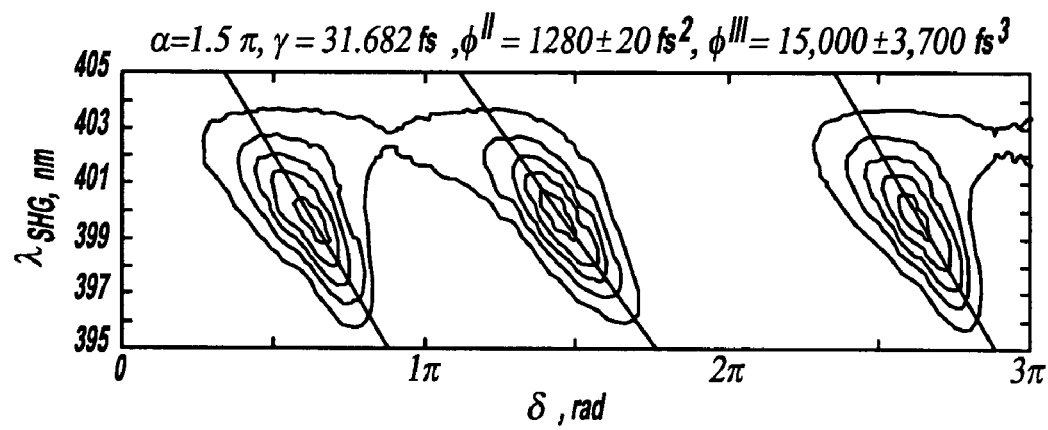
Figure 4C:
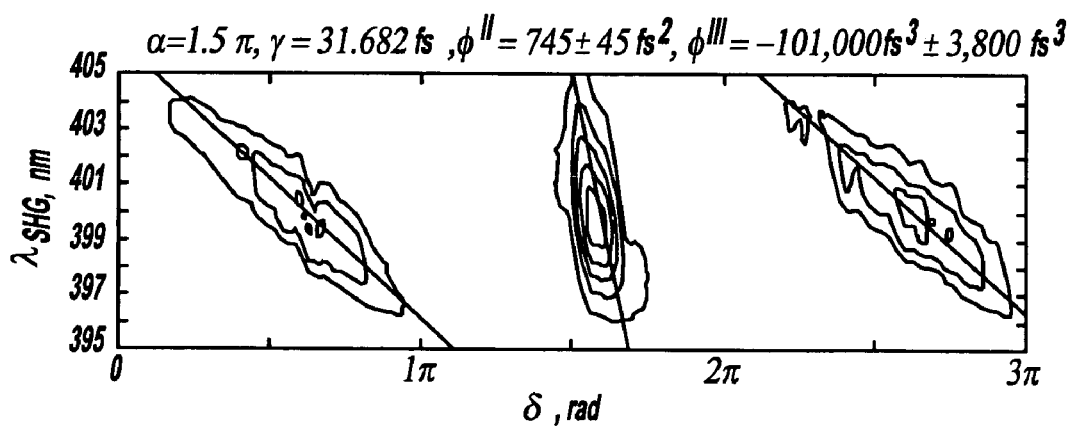

The phase mask shown in FIG. 9 is programmed on the SLM and it shows dramatic narrowing of the SHG spectrum as illustrated in FIG. 4. The contrast ratio as defined in FIG. 1 for this mask is 2.5 when the SHG peak is centered. By shifting the position of the mask on the SLM, hence tuning the center of symmetry, and thus tuning the SHG spectrum as shown in FIG. 11.

Figure 11A:
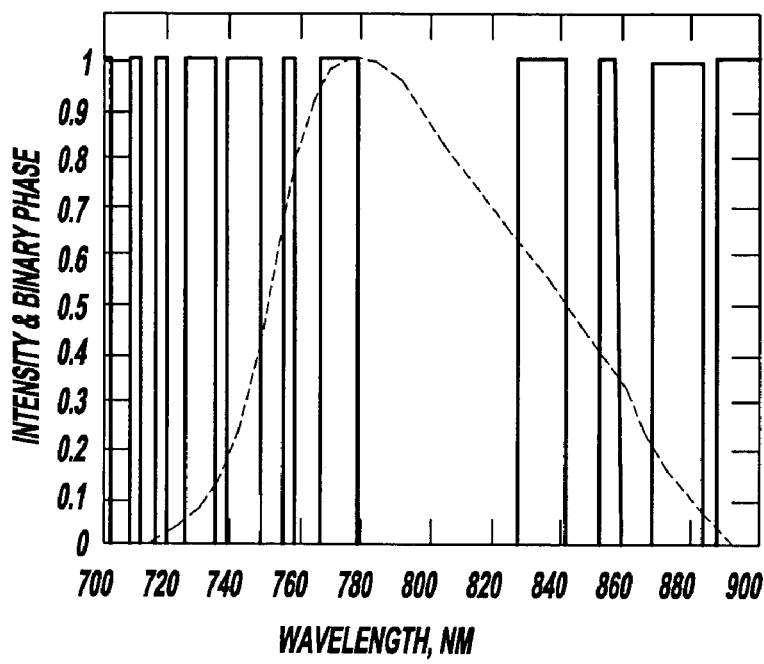
FIGS. 11a-11b are graphical representations of the pseudo-random number generation BPS and an output after second harmonic generation.
Figure 11B:
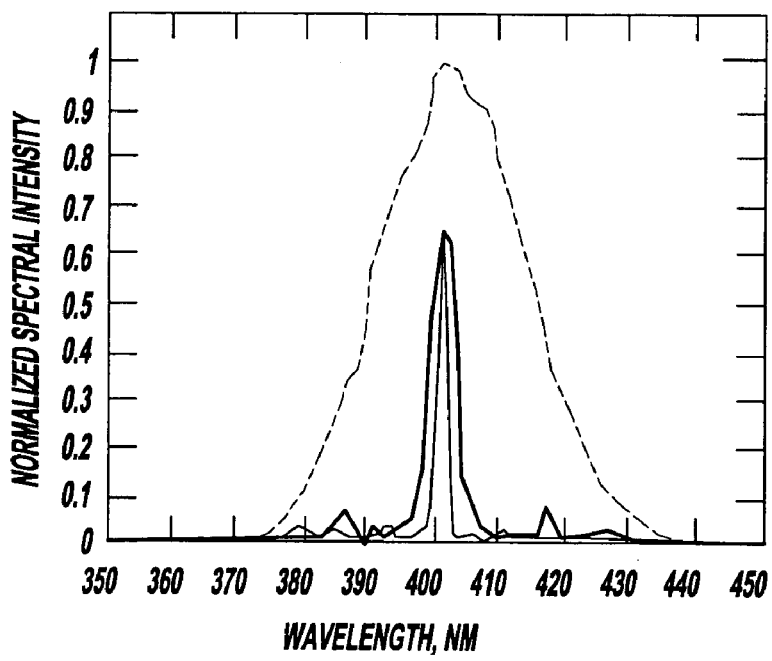

The dashed line in FIG. 11 corresponds to theoretical calculations. The absolute value of the spectral amplitude $|E(\omega)|$ of the electric field is calculated from the experimental power spectrum of the fundamental pulse $I(\omega)$ using $|E(\omega)|=I(\omega)^{0.5}$. To simulate the experimental results a double Fourier Transform method is used. The electric field in the time domain $E(t)$ is calculated as the Fourier image of the complex spectral amplitude in the spectral domain, with the formula $$E(t)=\int |E(\omega)|\exp[i\phi(\omega)]\exp(-i\omega t)d\omega, \quad [8]$$

where the spectral phase $\phi(\omega)$ is the function that is introduced by the SLM. The power spectrum of the SHG is calculated using $$I_{SHG}(\omega)=|\int E(t)^2 \exp(i\omega t)dt|^2. \quad [9]$$

The SHG amplitude is normalized using the maximum of the SHG intensity calculated for TL pulses, $\phi(\omega) \equiv 0$.

A simple evolutionary learning computer program (ELC) is programmed and it assumed a Gaussian electric field $|E(\omega)|$ corresponding to a 10 fs pulse centered at 800 nm. Eight points are used to represent each pixel in order to simulate more closely the experimental resolution of our setup. The second harmonic intensity is calculated according to $$I_{SHG}(2\omega_c)=|\int E(\omega_c-\omega)E(\omega_c+\omega)d\omega|^2 \quad [10]$$

normalized to the maximum SHG amplitude for TL pulses.

BPS simplifies the calculations, especially if it is assumed the amplitude of the electric field to be a constant, that is, the spectral power is set equal to 1 in the allowed spectral region. Each spectral component of the electric field, linearly dispersed in the frequency domain, can be represented as a binary value ($\pm 1$) determined by $b_k=\exp(i\phi_k)$, for $\phi_k=0$ or $\pi$ respectively. The intensity of the SHG signal measured at frequency $2\omega_k$ can be calculated with the formula $$S_k = \left| \sum_{j=0}^{N} b_{k-j}b_{k+j} \right|^2 / N^2 \quad [11]$$

where the integral in Equation 10 is now replaced by a discrete sum, N is a parameter that depends on details of the model such as number of pixels. The problem of spectral selectivity can now be formulated as finding a vector $b_k$ such that $S_k=1$ for $\omega_k=\omega_C$ and $S_k$ is minimized at all other frequencies.

Figure 12A:
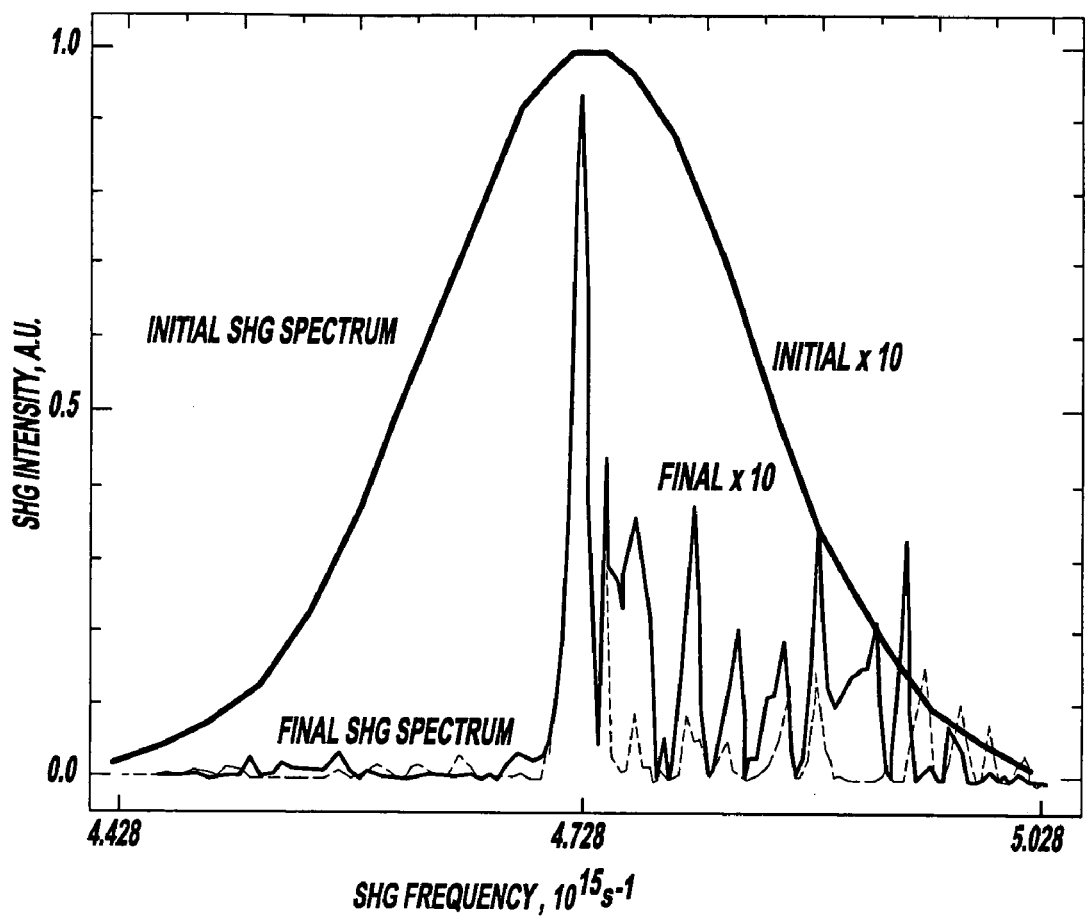

In FIG. 12, theoretical results from the phase described in FIG. 9 (black) are compared to the results of the ELC (dashed) which was initiated with the proposed phase. The evolutionary calculations used 100 individuals and one parent through 30 generations using single double and triple symmetric bit flips. The result from the ELC gives ~2.5 greater contrast. Using an SLM with more pixels, and grouping those pixels such that each group covers the same frequency range, improves the implementation and result in greater contrast, an observation based on our calculations. The goal of narrowing the SHG spectrum was motivated by the possibility of selective two-photon microscopy. To achieve this goal two conditions had to be satisfied, maximizing the nonlinear power spectrum at $2\omega_c$, and minimizing it elsewhere. Maximization has been investigated previously by Silberberg and coworkers, who identified the condition $\phi(\omega_c-\omega)=-\phi(\omega_c+\omega)$ for continuous functions. (See: N. Dudovich, B. Dayan, S. M. G. Faeder, Y. Silberberg, "Transform-limited pulses are not optimal for resonant multiphoton transitions," Phys. Rev. Lett. 86, 47-50 (2001) and D. Meshulach, Y. Silberberg, "Coherent quantum control of multiphoton transitions by shaped ultrashort optical pulses," Phys. Rev. A 60, 1287-1292 (1999)). Zheng and Weiner explored the narrow phase matching bandwidth SHG output at a single frequency, a problem that is analogous to two-photon excitation of an atom, using binary encoded pulses as used in communications. They found that limiting the phase to values of zero and $\pi$ led to the condition $\phi(\omega_c-\omega)=\phi(\omega_c+\omega)$. (See: Z. Zheng, A. M. Weiner, "Spectral phase correlation of coded femtosecond pulses by second-harmonic generation in thick nonlinear crystals," Opt. Lett. 25, 984-986 (2000) and Z. Zheng, A. M. Weiner, "Coherent control of second harmonic generation using spectrally phase coded femtosecond waveforms," Chem. Phys. 267, 161-171 (2001)). Under both shaping conditions the maximum signal approached that is obtained with TL pulses.

The problem of spectral narrowing by pulse shaping under broad phase matching SHG conditions, or selective excitation of large organic dyes and chromophores requires minimization of the nonlinear power spectrum away from $2\omega_c$. As expressed in Equation 11, there is an analogy with convolution. In this case, some binary functions have the property of giving a sharp 'delta function' convolution signal in one location and very low background elsewhere.

In principle, the solutions found are members of the set of solutions that could be obtained by arbitrary phase and amplitude pulse shaping. For a pulse shaper with N pixels, one can generate $(P*A)^N$ shaped pulses, where P and A are the number of different phases and amplitudes a pixel can take. If it is assumed 100 pixels, each taking 10 different amplitude values and 100 different phase values, the number of different pulses is of order of magnitude $10^{300}$. This number is extremely large, therefore, while in principle, the field exists to achieve the desired photonic transformation or excitation, finding it is a great challenge.

The periodic nature of electromagnetic waves results in a great deal of redundancy in pulse shaping because nonlinear optical processes do not depend on the absolute phase or a linear variation of the spectral phase. This equivalence is expressed by $\phi\omega \Leftrightarrow \phi(\omega)a+b\omega$, where a and b are constants. This redundancy is filtered out by programming an ELC that works on the second derivative of the phase. The actual phase that is used in the SLM is obtained by integration setting a=b=0. An ELC was used to optimize smooth phase functions for spectral narrowing, but could not obtain a contrast ratio greater than unity.

The advantage of BPS is that computational redundancies are greatly reduced. For BPS and 128 active pixels the search space is reduced to $2^{128}$. If there is two-fold symmetry, for example two-photon excitation, then the number is reduced to $2^{64}$. The final search space is of size $10^{19}$, a number that is at least 281 orders of magnitude smaller than would be considered for arbitrary phase and amplitude pulse shaping as discussed above. The resulting space is small enough that all possible outcomes could be computed, and a large portion evaluated experimentally. A simple ELC, such as the one used here can quickly converge towards significantly improved solutions.

BPS may have significant technological advantages. A retardation equivalent to $\pi$ is easy and fast to obtain and calibrate. Permanently etched masks can be made in advance and used for specific applications such as selective two-photon microscopy. Scanning the mask can yield two-photon excitation spectra.

It has been demonstrated that laser control, especially with two-photon transitions, can be addressed with binary phase shaping. BPS makes it simple to analyze the problem and to propose rational solutions, as demonstrated here with a phase mask fabricated by the quasi-random gaps between prime numbers. Thus, a simple ELC is used to improve on the proposed solution efficiently because of the greatly reduced search space.

Applications Using Binary Phase Shaping

Nonlinear optical processes, having a high-order dependence on light intensity, play a central role in a number of key technologies, among them multiphoton microscopy, multiphoton photodynamic therapy, multiphoton microlithography, optical switching, chemical sensors, and selective photochemistry. A sizable research effort is underway to improve the efficiency of these processes, focusing primarily on materials with large nonlinear optical susceptibility. Being able to enhance the efficiency for nonlinear excitation, or, in some cases, being able to suppress nonlinear optical distortion, remains a top priority in the design of photonic technologies. Research groups have been using laser systems with characterization and shaping technology to control nonlinear optical processes in large molecules, including proteins. Using the amplitude of the pulse and the spectral phase across its bandwidth, the power spectrum of the field can be determined. The spectral phase introduced by the shaper controls the way frequencies in the pulse add up to produce the higher nonlinear frequency components. The phase-dependent probability is used to manage the frequencies over which nonlinear optical processes are induced by a laser pulse.

Phase modulation introduces changes in the power spectrum of multiphoton processes. If the phase function $\phi$ in introduced in the SLM and scanned $\delta$ from 0 to $2\pi$, the power spectrum responsible for two-photon induced fluorescence changes accordingly. This approach is usable to achieve selective multiphoton microscopy. The system produces selective excitation of microscopic polystyrene beads doped with blue or green fluorescent dyes. Transform-limited pulses excite multiphoton transitions from both types of beads; however, the spectral phase of the laser pulse is modulated such that the pulse excited only specific types of molecules, providing selectivity. For these experiments, the output from the pulse shaper is focused directly on the sample being imaged by a microscope; the spectrum and intensity of the incident pulses remains unchanged in all cases.

Applications for this method include all the techniques that use multiphoton excitation. This method is used for pulse characterization and compensation, selective control of two and three-photon excitation, selective microscopic environment sensing and imaging, and selective multiphoton microscopy and imaging. MIIPS and BPS offer a powerful method for pulse characterization and compensation of ultrashort laser pulses. All applications involving nonlinear optical processes will benefit from the control that spectral phase manipulation brings through multiphoton intrapulse interference.

Multi-Photon Microscopy

Two-photon microscopy provides significant possibilities for fluorescence imaging and photochemistry. It offers attractive advantages, including higher resolution, background-free signal, lower background scattering, better penetration in thick samples, and reduced photon-induced damage, which arise from the basic physical principle that the absorption depends on the square of the excitation intensity. Two-photon microscopy is amenable to multiple-probe staining, whereby two-photon transitions excite different probe molecules that emit at different wavelengths, and for functional imaging of living cells. See U.S. Pat. No. 5,034,613 which issued to Denk, on Jul. 23, 1991; U.S. Pat. No. 6,166,385 which issued to Webb, on Dec. 26, 2000; U.S. Pat. No. 6,344,653 which issued to Webb, on Feb. 5, 2002; U.S. Pat. No. 5,759,767 which issued to Lakowicz, on Jun. 2, 1998; and W. R. Zipfel, et al., "Nonlinear magic: multiphoton microscopy in the biosciences," Nature Biotechnology, 121 (11): 1369-1377 (November 2003); all the above patents are incorporated herein by reference. Phase-modulated femtosecond pulses can selectively excite one type of probe molecule only, leaving the others in their ground state. Multiphoton excitation is achieved by multiphoton intrapulse interference (MII) and this can be accomplished efficiently using binary phase shaping. Selective excitation is used to enhance contrast and achieves functional imaging of samples stained with fluorescent probes sensitive to their microscopic chemical environment.

Figure 7:
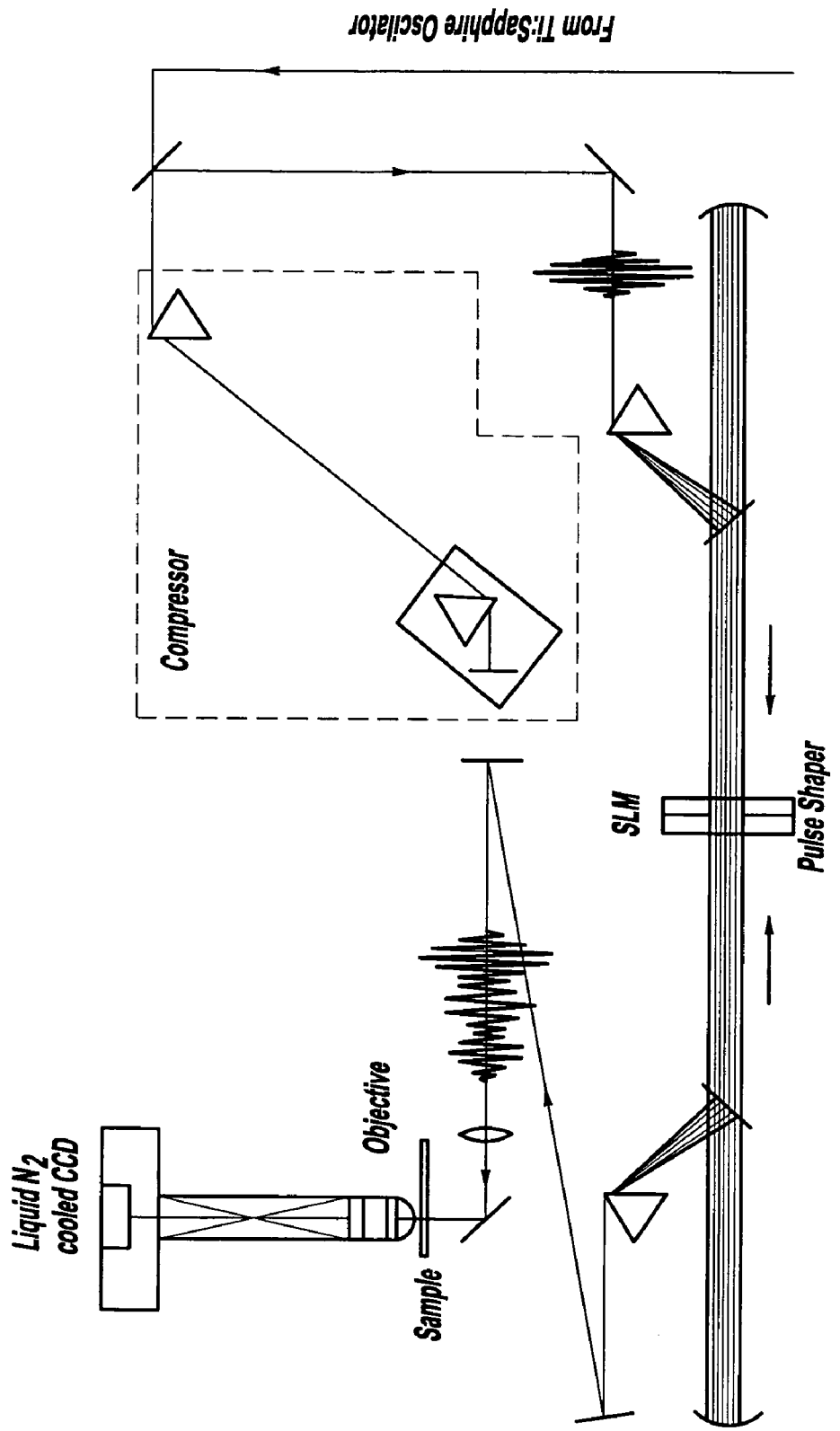
FIG. 7 is a diagrammatic view of a preferred embodiment of the present invention applied to multi-photon microscopy.

Preferably, a titanium-sapphire oscillator, which can be obtained from K&M Labs, is employed in the present invention laser system and is capable of generating pulses as short as 10 fs after a double pass prism compressor. The amplitude profile and spectral phase of the pulse is tailored using a computer-controlled pulse shaper of a design as described above. The shaper uses a pair of SF-10 prisms as the dispersion elements and 0.4 m cylindrical mirrors for collimation. A schematic of the experiment is shown in FIG. 7. Phase modulation is introduced by a computer-controlled spatial light modulator (SLM-256, CRI Inc.), located at the Fourier plane of the shaper setup. The pulses are centered near 800 nm. The spectral phase of each pulse is calibrated using the multiphoton intrapulse interference phase-scan method (MIIPS), first to obtain transform-limited (TL) pulses and then to introduce the desired phase. The spectral phase function used for this experiment is given by $$\phi(\Omega) = \alpha \cos(\gamma\Omega - \delta) \quad [12]$$

where $\Omega$ is the frequency detuning measured in $s^{-1}$ from the center wavelength of the laser pulse. The shaped laser pulses, with an energy of 0.2-1 nJ per pulse and 87 MHz repetition rate, are focused mildly, to a spot size of ~200 microns in diameter, on the different samples. Two-photon induced fluorescence is collected by an infinity corrected apochromatic microscope objective (APO 100X, Mitutoyo) and imaged into a liquid nitrogen cooled CCD detector using an Infini-Tube, preferably a Proximity Series model obtained from Infinity Photo-Optical. Experiments were carried out on three different types of samples. The first sample is prepared with acrylonitrile-vinylidene chloride polymer cured in acidic (pH 6) or basic (pH 10) buffered conditions and stained with the pH-sensitive fluorescent probe 8-hydroxypyrene-1,3,6-trisulfonic acid (HPTS) ($10^{-3}$ M) (Sigma-Aldrich). The second sample consists of pieces of polymethylmethacrylate (PMMA) doped with C540 and R6G fluorescent probes ($10^{-4}$ M). The third sample consists of a mixture of 10 μm blue and 15 μm green fluorescent FluoSpheres (Molecular Probes). The images are shown in black and white without optical filters in the collection optics or post image manipulation. The background, detector counts when the laser is off, is subtracted.

Figure 19A:
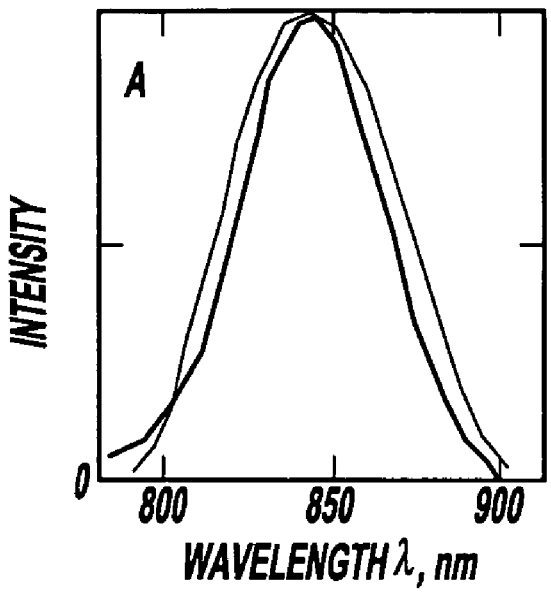
FIGS. 19a and 19b are experimental results and theoretical predictions of selective two photon excitation.

FIG. 19 shows the experimentally measured and theoretically predicted dependence of the contrast ratio of intensity of two-photon laser induced fluorescence between samples with pH 10 and pH 6 for the solutions of pH sensitive dye in order to demonstrate the MII principle. FIG. 19 shows the experimental results and theoretical predictions of selective two-photon excitation of HPTS solutions at different pH: (a) the laser spectrum plus a phase function; (b) calculated power spectrum of $E^2(t)$ for TL pulse; absorption spectra of HPTS at pH 10 (right side) and pH 6 (left side).

Figure 19B:
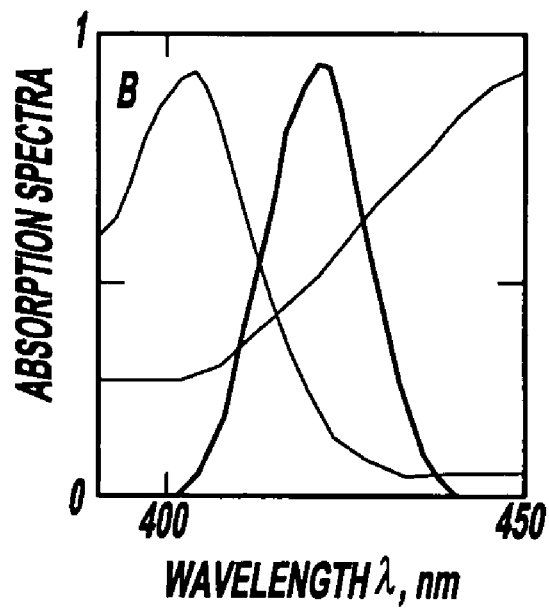

$10^{-5}$ M aqueous solutions of HPTS salt in different pH buffers are the exemplary samples. The laser spectrum remains unchanged throughout the experiments as spectral phase is modulated. The excitation spectra of HPTS exhibits large pH dependent differences while the emission spectrum centered at 515 nm is independent of pH. These measurements are obtained using 23 fs transform-limited pulses that were shaped to have a Gaussian spectrum centered at 842.6 nm with a bandwidth of 48 nm and spectral phase defined by Eq. [12] with α=1.5π, γ=20 fs. Spectral intensity $|E(\Omega)|^2$ and phase $\phi(\Omega)$ of laser pulse are presented in FIG. 19a. FIG. 19b shows the calculated spectrum of the electric field squared $E^{(2)}(\Delta) = E(\Delta/2+\Omega)E(\Delta/2-\Omega)d\Omega$ [13] where $\Omega = 2\pi c(1/\lambda - 1/\lambda_0)$ is the spectral detuning from the carrier frequency $2\pi c/\lambda 0$ of the laser pulse and $E(\Omega) = |E(\Omega)|e^{i\phi(\Omega)}$. Simulations of the experimental signal are performed using the following equation with no adjustable parameters:

$$S^{(2)} \alpha \int g^{(2)} |E^{(2)}(\Delta)|^2 d\Delta \quad [14]$$

where $\gamma^{(2)}(\Delta)$ is two-photon absorption spectra of HPTS at different pH (single photon spectra are shown in FIG. 19b. The spectrum of the pulse $|E(\Omega)|^2$ and the absorption spectra $g(\Delta)$ of HPTS are measured experimentally. Intramolecular dynamics, such as molecular vibrations, are neglected because they have a minimum contribution to MII. Because HPTS does not have inversion symmetry, its one-photon absorption spectrum $g(\Delta)$ is expected to be similar to its two-photon absorption spectrum $\gamma^{(2)}(\Delta)$. The contrast ratio between the measured intensity of fluorescence at pH 10 and pH 6 is presented as a function of δ. The experimental data obtained by excitation of the dye solutions in methanol ($10^{-3}$ M in water) generally agree with the calculated response.

Figure 20A:
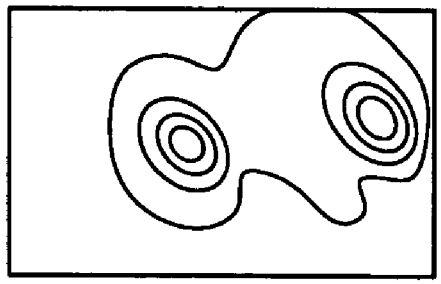
FIGS. 20a-20f are experimental results of pH-sensitive two photon microscopy.
Figure 20D:
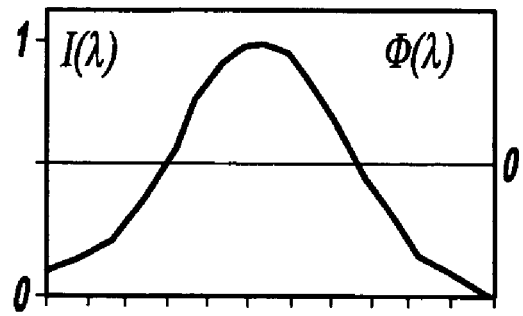
Figure 20B:
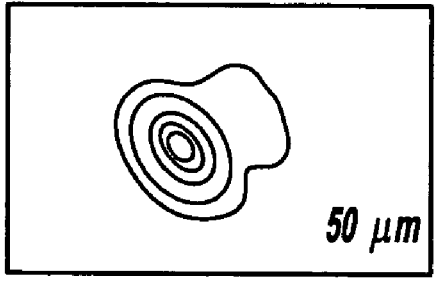
Figure 20E:
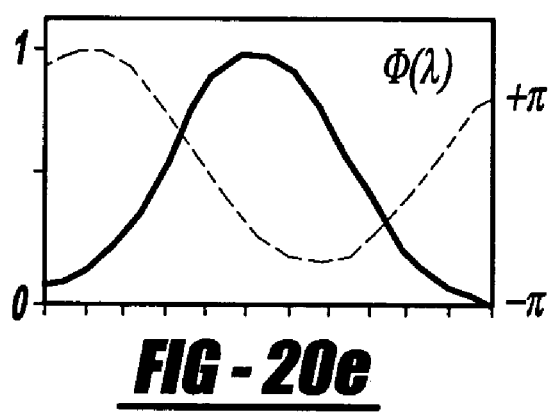
Figure 20C:
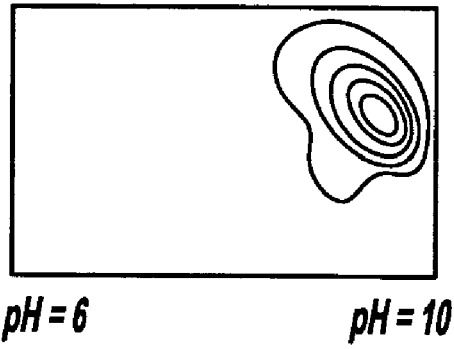
Figure 20F:
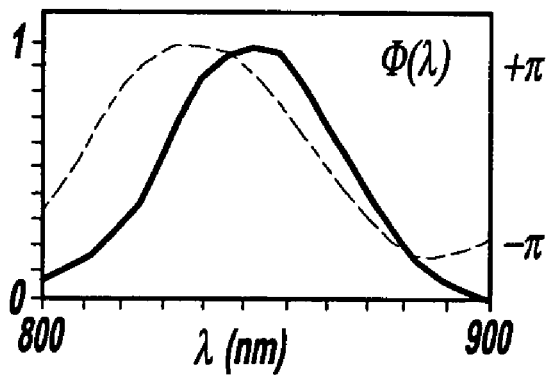
Figure 21D:
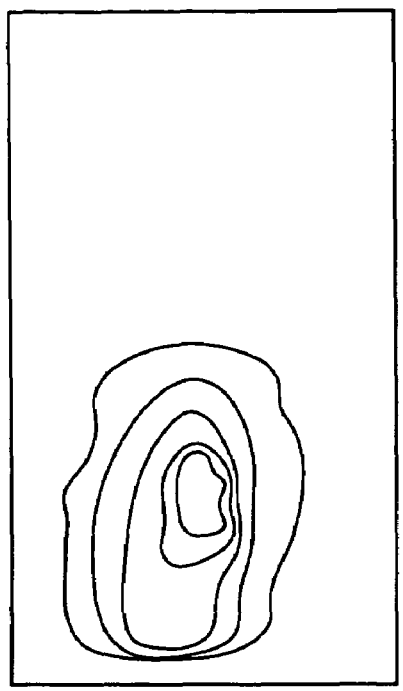
FIGS. 21a-21d are experimental results of selective two photon microscopy sample doped with different fluorescent probes.
Figure 21C:
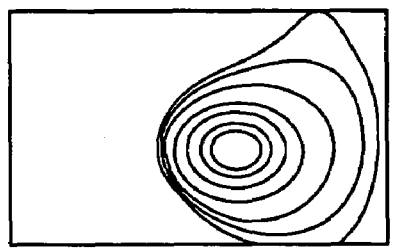
Figure 21B:
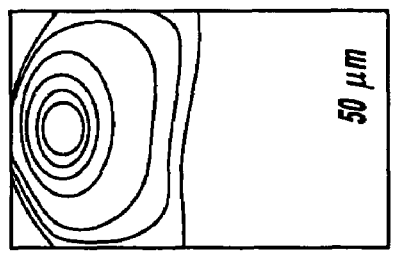
Figure 21A:
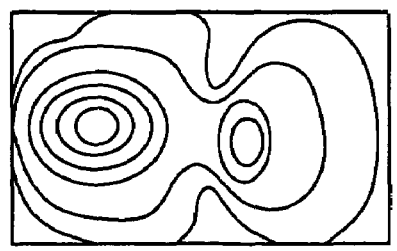

MII modulates the amplitude of the power spectrum of $E^2(t)$ as the spectral phase of the laser pulse $\phi(\lambda)$ is scanned. Note that the maximum amplitude in the power spectrum in FIG. 19d shifts from longer to shorter wavelengths, giving the possibility for selectively exciting the fluorescent probe in different pH environments. A solid sample of HPTS is prepared with different pH regions and imaged using a microscope. FIG. 20a shows an image obtained with TL pulses. The spectrum of the pulse and the spectral phase (flat line) are shown in the right panels. FIG. 20b shows an image obtained with laser pulses optimally shaped for selective excitation of HPTS under acidic environment. The spectral phase used to acquire this image is shown in the middle panel.

The experimental results in FIG. 21 show selective excitation of different fluorescent probes. FIG. 21a shows the data obtained using TL pulses. The two pieces of PMMA being imaged show similar amounts of two-photon laser induced fluorescence. When the spectral phase of the pulse is modified to optimize selective excitation of the C540-doped sample, only the top fragment fluoresces were observed, as shown in FIG. 21d. When the spectral phase of the pulse is optimized for selective excitation of the R6G-doped sample, FIG. 21c, strong fluorescence was observed from the bottom fragment while the other side, containing the C540 probe, does not fluoresce. Note that the spectrum and intensity of the laser remain constant during the experiment for all three cases. The only change is the subtle modulation of the spectral phase of the pulse, which controls multiphoton intrapulse interference. Contrast ratio (IR6G/IC540) (normalized intensities corrected to background) ranges from 1:9 for pulses optimized for C540 to 8:1 for pulses optimized for R6G. Selective multiphoton excitation minimizes the cross talk between different fluorescent probes and does not require the use of multiple filters and detectors for imaging.

The previous experiment shows selective two-photon excitation of different probe molecules. To further illustrate the potential of coherent control for functional imaging, selective excitation of microspheres is shown which is typically used for targeted staining of biological samples. Fluorescence from two different microspheres is shown in FIG. 22. The top image shows the green-fluorescent microsphere which has an absorption maximum at 450 nm, while the bottom image represents the blue-fluorescent microsphere, which has an absorption maximum at 365 nm. The image in FIG. 22a is acquired with TL pulses. Under these conditions, large two-photon induced fluorescence signal is observed from both spheres. For the image in FIG. 22d, the phase of the pulses is modulated such that the intensity of fluorescence from the blue microsphere is maximized and that of the green one minimized.

Figure 22D:
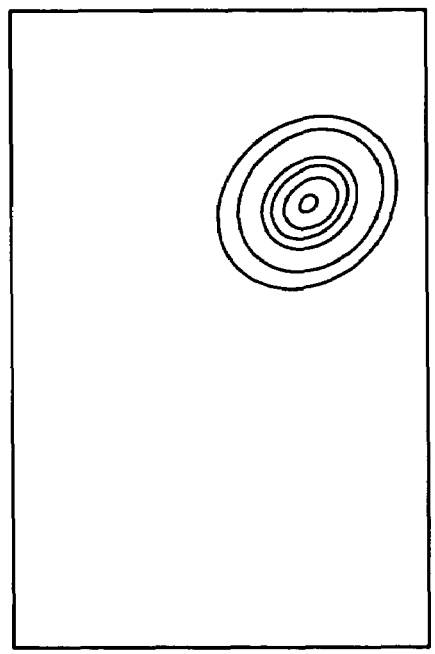
FIGS. 22a-22d are experimental results of selective two photon microscopy of microspheres.
Figure 22C:
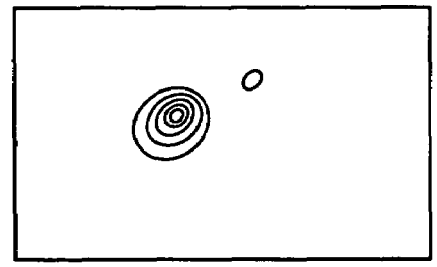
Figure 22B:
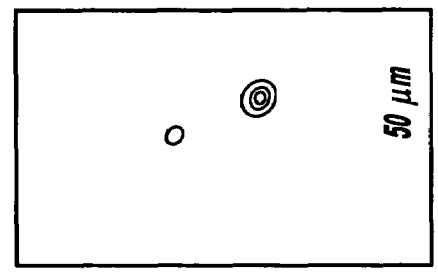
Figure 22A:
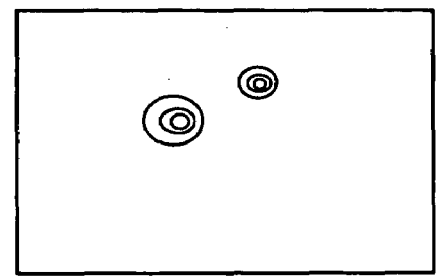

For the image in FIG. 22c, the phase of the pulses is modulated such that the fluorescence from the green microsphere is maximized and that of the blue one minimized. The observed contrast ratios ($I_{BLUE}/I_{GREEN}$) are 1:3 and 4:1 for the different phases.

Selective excitation with significant contrast ratios has been achieved here by optimizing the overlap between the power spectrum of $E^2(t)$ and the two-photon absorption spectrum. The addition of a computer-controlled pulse shaper to the multiphoton microscope provides a number of important advantages. First, the pulse shaper is used to compensate unwanted phase distortions at the sample. Linear chirp, for example, has been shown to reduce signal intensity in two-photon microscopy. With a pulse shaper, linear, quadratic, cubic and higher order chirp is compensated to obtain the most efficient excitation. Second, the pulse shaper is used to control the output spectrum of the laser pulses by amplitude modulation. Third, the pulse shaper is used for selective probe excitation as shown here. Because the spectrum of the laser remains constant, phase modulation does not affect one photon processes such as absorption, reflection and scattering. Selective excitation minimizes possible cross talk between different fluorescent probes in the sample. Finally, the pulse shaper is used to prevent three-photon and higher order nonlinear optical processes such as continuum generation. Higher order processes usually lead to sample degradation, and in the case of living samples to DNA damage. Suppression of three-photon transitions of four orders of magnitude has been achieved using the MII and BPS methods and this suppression can be coupled with optimization of two-photon signal from living specimens.

This method can be used to selectively excite either different probe molecules or identical probe molecules in different environments. In addition, this method can be used for selective excitation of luminescent probes such as quantum dots, metallic nanoparticles, and single molecules. For example, see, D. R. Larson, et al. "Water soluble quantum dots for multiphoton imaging in vivo," Science 300 1434-6, (May 30, 2003); and D. A. VandenBout, et al., "Discrete intensity jumps and intramolecular electronic energy transfer in the spectroscopy of single conjugated polymer molecules," Science 277, 1074-1077 (1997). The same principle can be extended to achieve functional imaging of semiconductor microchips by two-photon laser induced conductivity. For examples see: C. Xu, et al., "Two photon optical beam induced current imaging throughout backside of integrated circuits," Appl. Phys. Lett. 71, 2578-2580 (1997) and D. L. Osborn, et al., "Spectral and intensity dependence of spatially resolved two- photon conductivity defects on a GaAsP photodiode," J. Appl. Phys. 89, 626-633 (2001). Having a pulse shaper for multiphoton microscopy provides the flexibility of selective probe excitation or maximum signal enhancement by controlled modulation of the spectral phase of the femtosecond pulses. Even when for fluorescent labels with very similar absorption spectra, pulse shaping is shown capable of selective excitation. This level of selective excitation and enhancement can be adapted to different modes of two-photon and three-photon microscopy.

Multi-Photon Photo Polymerization

Microlithography involves the use of UV light to initiate polymerization. Two-photon induced polymerization has the advantage that it permits 3D polymerization of smaller features (down to 100 nm). Photonic band gap materials (PBGM) are 3D constructions with features similar to the wavelength of light that exhibit very interesting behavior. Two-photon microlithography is one convenient method for the preparation of very sophisticated PBGMs.

Two-photon absorption can be used in three-dimensional lithographic microfabrication (3DLM) through two-photon-induced polymerization (TPIP). This is due to the fact that simultaneous two-photon absorption requires a very high photon flux, which is only present at the point of the focus. Thus the TPI polymerization is confined to the focal volume. This high spatial resolution contributes to the ability of TPIP not only to scan the laser in the x and y direction but also to change the focal plane (z) without overwriting existing features. Therefore, 3DLM is obtained by a single processing step. 3D polymeric structures include a photonic band gap structure, waveguide structures and a micro-channel structure.

Examples of molecules that can be used in 3DLM have the general structure D-π-A-π-D, wherein D is a terminal group, π is a phenylimine function and A is an electron-accepting cyano group. Since cyano groups are used as the side groups, the increase of electron transfer leads to a significant increase in the δ value relative to electron-donating methoxy groups. Additionally, the change of the conjugated backbone through the introduction of the polar imino groups will allow the tuning of the linear and nonlinear optical responses of quadrupolar derivatives as a result of the influence of the chromophoric two-photon absorption properties. Both polar groups (—CHLN—) will enhance the extent of the charge transfer from the terminal groups to the center, correlated with the two cyano-groups. Upon chromophoric excitation, the p-conjugated center acts as an electron acceptor, and intramolecular energy and electron transfer will occur more readily from the terminal R2N— groups than via intermolecular energy and electron transfer. Radical forms can be easily generated in the terminal groups. Moreover, the solubility of the chromophore improves with the replacement of —CHLCH— by the polar flexible —CHLN— group. Due to the fact that they can be synthesized in one-step with a high yield and initiate polymerization of triacrylate monomer at a high level of sensitivity, makes application in two-photon-induced polymerization possible.

The following references disclose two-photon photopolymer initiators: "New Photopolymers based on Two-Photon Absorbing Chromophores and Application to Three-Dimensional Microfabrication and Optical Storage," B. H. Cumpston, et al., Mat. Res. Soc. Symp. Proc., Vol. 488, "Electrical, Optical, and Magnetic Properties of Organic Solid-State Materials IV," (MRS, Warrendale, 1998) p. 217; and "Two-Photon Polymerisation Initiators for Three-Dimensional Optical Data Storage and Microfabrication," B. H. Cumpston, et al., Nature, in press. It is envisioned that multiphoton intrapulse interference can be advantageously used to enhance this non-linear photopolymerization.

The following references are examples multi photon techniques for microlithography and microfabrication: Y. M. Lu, et al. "Highly sensitive two-photon chromophores applied to three dimensional lithographic microfabrication: design, synthesis and characterization towards two-photon absorption cross section" J. Mater Chem. 14 (1): 75-80 (2004); K. D. Belfield, et al., "Two-photon photoinitiated polymerization," J. Phys. Org. Chem. 13 (12): 837-849 (December 2000); B. J. Postnikova, et al., "Towards nanoscale three-dimensional fabrication using two-photon initiated polymerization and near-field excitation," Microelectron. Eng. 69 (2-4): 459-465 (September 2003); H. B. Sun, et al., "Two-photon laser precision microfabrication and its applications to micro-nano devices and systems," J. Lightwave Technol. 21 (3): 624-633 (March 2003); U.S. Pat. No. 6,316,153 to Goodman, issued Nov. 13, 2001; U.S. Pat. No. 6,259,104 to Baer, issued Jul. 10, 2001; and U.S. Pat. No. 6,288,782 to Worster, issued Sep. 11, 2001; all of the above patents are incorporated herein by reference.

Currently, two-photon microlithography and related techniques can only initiate one type of polymer. If two different types were needed, one would need to rinse, change the monomer mixture, find the position of the feature with nanometer accuracy, and make the new feature.

In one embodiment, BPS is used in microlithography and related techniques such as micromachining and microfabrication to control the polymerization of two different polymers. Being able to alternate two different polymers allows greater flexibility in the construction of nanometer features such as, but not limited to, microelectromechanical systems (MEMS). Controlling the deposition of two different polymers is enabled by the control of what wavelength two-photon excitation takes place.

Quantum Computing

One such important application of the concepts of coherent control is emerging in the area of quantum computing. The selectivity in excitation, which is offered by shaped laser techniques, may also serve as the building blocks for the development of the first practicable quantum computer. In a prior optical scheme for quantum computing, computer controlled pulse shaping where information storage and retrieval through quantum phase is required. In case of an eight-state Rydberg atom wavepacket, the prior scheme can store information as a quantum phase in one or more flipped state, which could be subsequently retrieved in a single step in agreement with the Grover's; this prior scheme is disclosed in J. Ahn, et al., Science 287 (2000), p. 463; and N. Bhattacharya, et al., Phys. Rev. Lett. 88 (2002) 137901-1.

A typical visualization of a traditional quantum computer network would have nodes consisting of quantum storage devices, where information can be stored for very long times either in ground or in some metastable excited states of atoms, molecules or ions. The quantum information can be transferred from one node of the network to the other using photons. The nodes would carry out the required computations and also serve as a storage or memory unit. The storage time is limited by decoherence time. Transferring quantum information between the two nodes without allowing for decoherence is very difficult. There are already some proposals in quantum communication to transmit and exchange quantum information between distant users, which includes distribution of quantum secure key information for secure communication. Teleportation allows an arbitrary unknown quantum state to be conveyed from one distant part to another with perfect fidelity by the establishment of a maximal entangled state of two distant quantum bits. However, the bottleneck for communication between distant users is the scaling of the error probability with the length of the channel connecting the users. The error results from amplitude and phase damping.

Advantageously, optical pulse shaping of the present invention is an attractive route to quantum computing since shaped pulses can be transmitted over optical hardware and the same infrastructure can be used for computation and optical information transfer. The shaped pulses are split into a number of different parts which can carry different train of pulses at different timescales. This provides leverage to control the various nodes where molecular systems interact with shaped pulses to carry out various instructions and perform quantum computing activity at each node during the pulse duration. This further enables the processing of different quantum computational steps at various nodes simultaneously, such that the code is transmitted in parallel for distribution of the task over the network. At the end of the computation the results are read by sending in a "read pulse" and recombining the results. Essentially, this is distributed quantum computing over the network using shaped pulses. Currently, 106 bits can be transmitted/encoded in a single burst of light with the present day optical pulse shaping technology. The repetition rate from the laser source is about 50 to 100 MHz. Thus, one would be able to use terabit/sec bit of communication channel through the existing infrastructure available with the optical community. Once such a quantum computer is available at remote site, these packets acting as "quantum software" can be transferred through high-speed communication channels. Thus, it is possible to carry out quantum computation at a remote distance with the proposed scheme of shaped pulses for terabit/sec communication and molecular control. For examples, see, Goswami D, Quantum Physics 0312192 (Dec. 24 2003); Garcia-Ripoll JJ, et al., Phys. Rev. Let., 91(15) 157901 (2003); Yang W, et al., J. Opt. Comm. Vol. 22, No. 1, pp. 694-697 (2001); Leibfried D, et al., J. Mod. Optic. 50 (6-7): 1115-1129 (April-May 2003); Pazy E., et al,. Phys. Rep. 374 (6): 385-481 (February 2003); Goswami D., Phys. Rep. 374 (6): 385-481 (February 2003); Brattke S., et al., Phys. Rev. Lett. 86 (16): 3534-3537 (Apr. 16, 2001); and Weinacht T. C., et al, Nature 397 (6716): 233-235 (Jan. 21, 1999); in addition U.S. Pat. No. 6,678,450 which issued to Franson on Jan. 13, 2004; and U.S. Pat. No. 5,793, 091 to Devoe issued Aug. 11, 1998; all the above patents are incorporated by reference herein.

Optical Coherence Tomography

A preferred embodiment of the present invention uses a laser system 221 for laser excitation or ionization with Optical Coherence Tomography ("OCT"). In general, FIG. 13 illustrates the OCT application of system 221 wherein there is a femtosecond laser 223, a laser beam shaper 229, a human or animal tissue specimen 241, an optical gate 251 and an image 253. Laser 223 emits a laser beam pulse shorter than 1 picosecond. Shaper 229 is made of three parts; two dispersive elements 255 which sandwich a phase mask element 257. Shaper 229 essentially prevents multiphoton excitation which can damage the person's or animal's DNA, as will be discussed in more detail as follows. An unshaped laser beam pulse is used to gate the ballistic photons to render the image for tomography use. Optical gating can be accomplished by up-conversion in a frequency doubling crystal or with a kerr-gate in liquid carbon disulphide. The construction of system 221 as illustrated supposes transmission imaging; the same end result can alternately be accomplished with back scattered imaging. Image 253 could be viewed like an x-ray-type image of the internal organs of the human or animal specimen but without harmful three photon exposure. The use of the shaped pulse in OCT provides for an increase in laser intensity for better imaging while preventing the damaging effects caused by multiphoton excitation of healthy tissue. The MIIPS and BPS processes discussed hereinafter can be advantageously used to activate different dyes and other compounds within a human or animal tissue, to achieve compound specific or functional OCT or microscopy. The pulse shaper is used to prevent three-photon and higher order non-linear optical processes such as continuum generation. Higher order processes usually lead to sample degradation, and in the case of living samples to DNA damage. Suppression of three-photon transitions of four orders of magnitude has been achieved using the MII and BPS methods and this suppression can be coupled with optimization of two-photon signal from living specimens. Alternatively, a fluorescent contrast agent can be administered so that pulses shaped using BPS selectively excite the fluorescent agent targeted towards malignant tumors. The embodiment is expected to achieve functional deep tissue imaging.

Referring now to FIG. 15, a system setup for functional imaging using BPS is shown. The tissue has been injected a fluorescent contrast agent that is preferentially absorbed by tumors. The fluorescent is a pH sensitive dye or derivatized quantum dots. No time grating is required.

Photodynamic Therapy

Another embodiment of the present invention uses a system also shown as 221 for laser excitation or ionization with photodynamic therapy ("PDT"). PDT is a treatment that involves the combination of visible light and a photosensitizer. Each factor is harmless by itself, but when combined with oxygen, can produce lethal cytotoxic agents that can inactivate tumor cells. This enables greater selectivity towards diseased tissue as only those cells that are simultaneously exposed to the photosensitizer, light and oxygen are exposed to the cytotoxic effect. The dual selectivity of PDT is produced by both a preferential uptake of the photosensitizer by the diseased tissue and the ability to confine activation of the photosensitizer to this diseased tissue by restricting the illumination to that specific region. Therefore, PDT allows for the selective destruction of tumors while leaving normal tissue intact.

PDT is based on the concept that (1) certain photosensitizers can be localized (somewhat preferentially) in neoplastic tissue, and (2) subsequently, these photosensitizers can be activated with the appropriate wavelength (energy) of light to generate active molecular species, such as free radicals and singlet oxygen ($^1O_2$) that are toxic to cells and tissues. PDT is a binary therapy, and a potential advantage of PDT is its inherent dual selectivity. First, selectivity is achieved by an increased concentration of the photosensitizer in target tissue, and second, the irradiation can be limited to a specified volume. Provided that the photosensitizer is nontoxic, only the irradiated areas will be affected, even if the photosensitizer does bind to normal tissues. Selectivity can be further enhanced by binding photosensitizers to molecular delivery systems that have high affinity for target tissue. For photoactivation, the wavelength of light is matched to the electronic absorption spectrum of the photosensitizer so that photons are absorbed by the photosensitizer and the desired photochemistry can occur. Except in special situations, where the lesions being treated are very superficial, the range of activating light is typically between 600 and 900 nm. This is because endogenous molecules, in particular hemoglobin, strongly absorb light below 600 nm and therefore capture most of the incoming photons. The net effect would be the impairment of penetration of the activating light through the tissue. The reason for the 900 nm upper limit is that energetics beyond this wavelength are insufficient to produce $^1O_2$, the activated state of oxygen, perhaps critical for successful PDT.

The photochemical and photophysical principles of PDT are well known in the art. Briefly, upon illumination, the photosensitizer is excited from the ground state ($S_0$) to the first excited single state ($S_1$), followed by conversion to the triplet state ($T_1$) via intersystem crossing. The longer lifetime of the triplet state enables the interaction of the excited photosensitizer with the surrounding molecules, and it is generally accepted that the generation of the cytotoxic species produced during PDT occurs whilst in this state.

The excited triplet state can react in two ways, defined as Type I and Type II mechanisms. A Type I mechanism involves hydrogen-atom abstraction or electron-transfer reactions between the excited state of the sensitizer and a substrate that is either biological, a solvent or another sensitizer, to yield free radicals and radical ions. These free radical species are generally highly reactive and can readily interact with molecular oxygen to either generate reactive oxygen species such as superoxide anions or hydroxyl radicals or can cause irreparable biological damage. These reactions produce oxidative damage that is eventually expressed as biological lesions. By contrast, a Type II mechanism results from an energy transfer between the excited triplet state of the sensitizer and the ground-state molecular oxygen, generating the first excited state of oxygen, singlet oxygen. This zwitterionic species is extremely reactive and can interact with a large number of biological substrates, inducing oxidative damage and ultimately cell death. While it is generally accepted that Type II processes predominate during PDT and that singlet oxygen is the primary cytotoxic agent responsible for the biological effects displayed, Type I reactions become more important at low oxygen concentrations or in more polar environments. However, the initial reaction is of lesser importance as both Type I and Type II reactions lead to similar oxidative damage and comparable free radical chain-reactions in the presence of oxygen. The overall effect of either a Type I or Type II reaction pathway is the production of oxidative damage within the target cell that will ultimately lead to tumor destruction.

Under special circumstances (short pulse, high intensities of irradiation), the upper excited states may be populated, and complex photophysical and photochemical processes may originate from these states, resulting in increased or decreased phototoxicity, which may include oxygen-independent mechanisms such as DNA mutation.

Photosensitizers are compounds that are capable of absorbing light of a specific wavelength and transforming it into useful energy. In the case of PDT, this would involve the production of lethal cytotoxic agents. There are hundreds of natural and synthetic dyes that can function as photosensitizers for PDT, ranging from plant abstracts to complex synthetic macrocycles. The key characteristic of any photosensitizer is its ability to preferentially accumulate in diseased tissue and to then generate cytotoxic agents to induce the desired biological effect. (For examples of such photosensitizers See W. M. Sharman, et al., "Photodynamic therapy: basic principles and clinical applications," Drug Discovery Today 4(11):508-517 (1999); T. Hasan, et al., "Photodynamic Therapy Of Cancer," Chapter 40 in Holland Frei Cancer Medicine, BC Dekker Inc. (2003); W. M. Sharman, et al., "Targeted photodynamic therapy via receptor mediated delivery systems," Adv. Drug Delivery Rev. 56(1):53-76 (January 2004); and Roy I., et al., "Ceramic-based nanoparticles entrapping water-soluble photosensitizing drugs: A novel drug carrier system for photodynamic therapy." J. Am. Chem. Soc. 125:7860-7865 (2003)).

In general, FIG. 13 also illustrates the PDT application of system 221, but optical gate 251 and image 253 are not required. Shaper 229 allows two-photon excitations but essentially prevents three-photon excitation. Shaper 229 enhances the laser-induced activity of a therapeutic agent which prevents damage of healthy tissue. Use of laser beam pulse shaping of the present invention should provide superior control and results for PDT applications as compared to those practically possible with conventional methods as disclosed, for example, in U.S. Pat. No. 6,042,603 entitled "Method for Improved Selectivity in Photo-Activation of Molecular Agents" which issued to Fisher et al. on Mar. 28, 2000, and is incorporated by reference herein. Alternately, the pulse shaper can be tuned to target cancerous cells for multiphoton gene therapy or destruction, with or without the presence of a therapeutic agent, without damaging healthy tissue. The MIIPS and BPS processes discussed hereinafter can be advantageously used to activate only certain pharmaceuticals or chemicals, or used to allow the laser pulse to enter human or animal tissue to a known depth, based on the phase tuning and associated nonlinear spectrum tuning of the laser beam pulse. The pulse shaper is used to prevent three-photon and higher order nonlinear optical processes such as continuum generation. Higher order processes usually lead to sample degradation, and in the case of living samples to DNA damage. Suppression of three-photon transitions of four orders of magnitude has been achieved using the MII and BPS methods and this suppression can be coupled with optimization of two-photon signal from living specimens.

General applications of lasers for biomedical purposes are well known for diagnostic tools, surgical tools and for imaging purposes. The immediate extension of ultrashort pulse shaping technology for biomedical applications holds many promises, to further necessitate looking into its domain of influence. Though very few applications for ultrafast pulse shaping technology are currently in use, there are very strong indications as to where it would lead. One of the most commonly adopted methods, for imaging, in recent times for three-dimensional profile measurement is optical coherence tomograph or a white light interferometer, which uses a broadband, low coherence light source. Recently the principle of femtosecond pulse shaping by spectral modulation has been used in conjunction with the joint transform correlator to make a spatio-temporal joint transform correlator. The advantage of such a technique has been that it essentially removed the need of 1-D depth scanning and thereby avoided the long measurement times involved. Consequently, this eliminates the electronic computation needed to obtain the object image, and so it can be implemented as an all-optical set-up. Initially, this was demonstrated as a surface measurement set-up, however, as a natural extension, it was easily extended for providing tomographic sectioning of biological samples. In fact, with the use of principles of pulse shaping, a depth resolution of 70 μm was achieved. Furthermore since there is no contact between the probe and the tissue, it is a useful non-invasive technique, which provides the physician with near-histological resolution imaging of sub-surface tissue morphology, potentially aiding in biopsy site selection and thus approaching the goal of "optical biopsy".

Nonlinear Optical Excitation Spectroscopy

In one embodiment of the invention, the goal is to develop laser systems capable of generating ultrashort pulses with unprecedented control over the spectral profile and phase properties of the pulses. Specifically, the systems are capable of generating ultrashort pulses that are within 1% of the transform limit, as determined by accurate pulse characterization, by a novel method that incorporates phase characterization and compensation in a single pulse shaping/characterization unit. The same unit will provide calibrated synthesis of arbitrary pulse shapes. One embodiment of the invention, a laser system forms an integral part of a microscope capable of functional imaging, a method whereby pulses are tailored to excite chromophores sensitive to their microscopic chemical environment (pH, $Ca^{++}$, $Na^+$ gradients).

In another embodiment of the invention, a laser system is amplified and shaped by a two-dimensional spatial light modulator. The system is capable of providing single-shot multiphoton excitation spectra over a 20-30 nm range, with 0.05 nm resolution. Two-photon excitation spectra of molecules are usually acquired point by point and are prone to order-of magnitude errors. The system is capable of acquiring 1000 spectra per second over 30 nm excitation regions, and referencing them to a standard. The system improves the accuracy and speed of nonlinear frequency resolved excitation spectroscopy and cross section measurements by orders of magnitude. This information is central to selection and utilization of nonlinear optical materials.

Nonlinear optical excitation spectroscopy (NOES) involves the measurement of nonlinear processes such as two- or three-photon excitation cross-sections and nonlinear optical susceptibilities as a function of wavelength. These measurements are of great importance for the characterization of nonlinear optical materials and nonlinear optical chromophores such as laser dyes and quantum dots. Two-photon excitation spectroscopy, for example, requires a tunable laser source that is both narrow in frequency but highly efficient in multiphoton excitation. Typically, a narrow bandwidth tunable laser is used to obtain data from 700 to 950 nm, acquiring the data point by point. Nonlinear spectroscopy is extremely sensitive to transverse mode quality, spectral phase, characteristics of the focal spot, pulse-1 to-pulse intensity variations, and wave front deformations; all of which can cause higher or lower order processes that contaminate the result. All of these factors make point-by-point acquisition prone to systematic errors.

A practical but naive approach would be to generate a broad bandwidth pulse and then to scan a slit across its spectrum to narrow the spectral resolution at specific wavelengths. This approach reduces the efficiency of second and higher order processes by two or more orders of magnitude.

To solve these problems, an embodiment of the invention is based on binary phase masks based on the principles of intrapulse interference (MIIPS) and then optimized using learning calculations afforded by an evolutionary learning calculation. The binary phase mask and the corresponding output for transform limited and for shaped pulses are shown in FIG. 8, together with a demonstration of how these masks are used to tune the location where second order processes take place. The red trace is a simulation of the data. The laser is focused on a thin BBO crystal and the frequency-doubled output is collected with a spectrometer. Each phase mask is designed to produce a narrow and high contrast maximum at a different wavelength. These results were obtained with 18 fs pulses using a 128-pixel pulse shaper. Notice that the narrowed output is about 65% of the efficiency observed with TL pulses. Using an amplitude mask to block the spectrum of the laser, as shown in FIG. 11, above, resulted in only 3% conversion efficiency.

An embodiment of the invention acquires spectra across a large bandwidth in a single laser shot. The high data throughput permits very accurate calibration to some of the best-known standards such as the nonlinear optical crystal KDP and the laser dye Rhodamine 6G. The laser system is not be scanned; in fact, the amplitude of the laser field remains unchanged throughout the experiment. This permits outstanding calibration of all the factors that could affect nonlinear output.

A diffractive two-dimensional programmable phase modulator originally designed by Hamamatsu for optical computing, is ideally suited for this task. The PPM X8267 is a 1024×768 pixel electrically-addressed phase modulator using an image transmitting element to couple and optically-addressed PAL-SLM (parallel aligned nematic liquid crystal spatial light modulator). The number of pixels available for pulse shaping is critical in the design. The generation of well-defined pulses requires the introduction of a well-defined phase functions. Pixilation effects, where a smooth phase is replaced by a jagged, under-sampled phase can be detrimental. The PPM units are illuminated by a spatial image, which is projected into the PAL-SLM. The projection system provides high accuracy reproduction without pixel borders, making it ideal for pulse shaping purposes. The femtosecond laser that is modulated is spectrally dispersed by a 300 lines/mm gold coated diffraction grating and collimated by a gold-coated cylindrical mirror forming a reflective 2$f$ arrangement. The PAL-SLM is placed at the Fourier plane (where best spectral resolution is achieved). The reflected light is collected by an optical arrangement identical to the input one. Chromatic aberrations and group velocity dispersion are kept to a minimum by the all-reflective optical design. Nonlinear optical distortions and optical damage are minimized by the use of cylindrical rather than spherical optics. The spectrums are dispersed on the horizontal dimension. The pixels in the vertical dimension contain different phase masks that scan the wavelength where nonlinear excitation takes place. A schematic of the phase mask is shown in FIG. 14.

A embodiment of the invention, illustrated in FIG. 15, produces amplified sub-20 fs pulses (~$10^6$ times more energy per pulse than laser System A), but at a repetition rate of 1 kHz. The bandwidth of the pulses is 50 nm FWHM, and is used to obtain NOES with about 0.2 nm resolution. The seed pulses are produced by a K&M Labs oscillator which is pumped by a Verdi laser (Coherent). The amplifier is an Odin, multipass amplifier from Quantronix, pumped by their Quantronix Darwin Q-Switched Nd:YLF, capable of delivering 1 mJ per pulse at 1 kHz. The Quantronix system is quoted for sub-35-fs performance. However, the amplifier is capable of preserving most of the oscillator bandwidth. The amplifier design is based on the multi-pass platform that Kapteyn and Murnane used to demonstrate generation of 17 fs pulses. To achieve the very short pulse duration a grating and prism compressors are used.

The laser system is installed on a 5'×12' vibrationally isolated optical bench (Newport). Pulse characterization is carried out by FROG, SHG-FROG, and MIIPS. For FROG, an optical delay line (Aerotech) is used. Data collection is accomplished using an Ocean Optics spectrometer, a Boxcar Averager/Integrator (SRS), a 500 MHz digital oscilloscope (Infinium, Hewlett Packard), and controlled with a personal computer running LabView, with a GPIB IEEE 488 controller.

Two-dimensional pulse shaping allows single-shot NOES data to be acquired from nonlinear optical materials, two-photon excitation spectra of laser dyes, biologically tagged fluorescent markers, quantum dots, optical switches and other optical materials. The wavelength range is limited to the 700 to 900 nm window by the pump pulses. The laser system is used to pump a non-collinear optical parametric amplifier, producing tunable broad bandwidth pulses from 450 to 1300 nm. These pulses are directed to the two-dimensional pulse shaper when characterization of a material is required at very different wavelengths.

The MIIPS method, described previously, requires the scanning of a reference phase across the spectrum of the laser. This usually requires acquisition of the SHG output spectrum for ~100 different phase function positions. To achieve this task in a single shot, the vertical dimension is divided into 128 different sections. Each section, containing 6×1024 pixels, contains the reference phase function. The key is that the phase function is displaced in each of the sections to provide the data as a function of δ required for MIIPS. Once the femtosecond laser pulse undergoes the two-dimensional phase modulation it is focused with a short focal length ~100 mm cylindrical mirror on a thick SHG crystal. On the horizontal axis, the thick SHG crystal causes a spectral dispersion that is analogous to the one used in the GRENOUILLE. On the vertical axis, one obtains different sets of sets of SHG spectra because of the different phase functions encoded by the PAL-SLM. The entire two-dimensional image, containing the one-shot MIIPS data is then imaged onto a CCD for collection and analysis.

Communications

With reference to FIG. 16, another preferred embodiment of a laser excitation system 421 of the present invention employs a femtosecond laser 423, an optical fiber 451, a laser beam pulse shaper device 429, a laser beam pulse un-shaper device 453, and a receiver 441 which includes an optical switch or sensor and the related circuitry and electrical control unit. Laser 423 emits a series of laser beam pulses, each shorter than 1 ps, into the connected fiber 451. Pulse shaper device 429 is of a predetermined mask type with a fixed pulse characteristic varying shape (such as with calculated sine wave surface shapes) and has three elements connected to fiber 451: a dispersive element 455 such as a fiber that incorporates a diffraction grating; a phase mask element 457 that can be made using a doped glass or polymer sheet; and a dispersive element 459, like element 455 but reversed, for accepting spectrally dispersed light and coupling it back to fiber 451.

The shaped laser beam pulse is capable of traveling long distances through fiber 451 without suffering nonlinear distortion because of the unique phase function imprinted or formed on shaper device 429. For example, the red color spectrum may be advanced in front of the blue color spectrum in a precise sine manner. Un-shaper device 453 subsequently reverses the phase changes introduced by shaper device 429. It is constructed the same as the shaper device but with a different phase mask element 461 that compensates for the pulse characteristic changes made by mask element 457. Alternately, an acousto-optic modulator or transient grating can be used for optical switching through constructive or destructive reference of waves. Shaping and unshaping can also be accomplished by means of a chirped mirror or spectral masks.

Thus, the present invention's ability to precisely control the laser beam pulse shape or other characteristic, especially for nonlinear or multiphoton emissions, significantly improves the quality of the communication transmission while minimizing self-focusing, self phase modulation and possible destruction of the fiber. The pulse characteristic control of ultrafast laser beam pulses, as described in all of the embodiments herein, should minimize, if not prevent, multiplicative noise effect disruption of nonlinear propagation channels in fiber optic lines, as discussed in Mitra, et al., "Nonlinear Limits to the Information Capacity of Optical Fibre Communications," *Nature*, vol. 411, pp. 1027-1030 (Jun. 28, 2001). It is further envisioned that this type of pulse shaping system can be employed within salt water oceans for submarine-to-submarine communications using short laser pulses of 1 ps or less. This type of pulse shaping can be used to induce solution formation to achieve minimally distorting pulses for communications. Moreover, MIIPS can be used to measure the distance of a fs laser emitter by determining the magnitude of the acquired second order phase modulation as the laser pulse transmits through air or water. This method does not require echo or reflection. In water longer pulses (1 ps) are desired because of the much greater dispersion. Depending on the transmission medium, air or water, and the distances expected different pulses are required. For air, short pulses with durations between 10-20 fs will be preferred. For water, pulses with much longer durations will be preferred, for example for 100 m distance 100 ps pulses would be preferred.

Using the BPS method, the data density that can be achieved per pulse is equal to or less than the number of pixels in the SLM divided by 2. For example, in an embodiment in the SLM 429 has 256 pixel resolution, the maximum data density is 256/2 or 128 bits per pulse. In this embodiment, if the pulse rate is 100 MHz, the data rate or bandwidth would be $10^{10}$ bits per second. Other embodiments of the invention vary the data rate or bandwidth based on pixel resolution and/or laser pulse rate. As laser pulse rates increase and as SLM pixel resolution increases, the bandwidth achievable by this invention will increase. It is advantageous that only a nonlinear optical detector would be able to decode the signal and, in contrast, a simple light detector would not be able to determine any information from the pulses. The fact that it can be used asynchronously is ideal for mobile or distant, and intermittent communications.

Figure 18A:
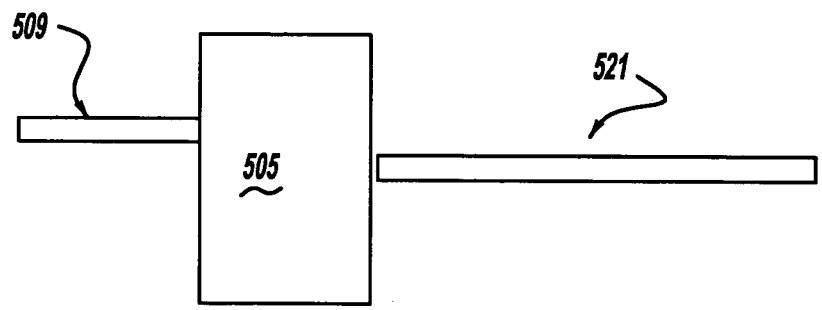
FIGS. 18a and 18b are diagrammatic views showing components in an alternative preferred embodiment applied to communications.
Figure 18B:
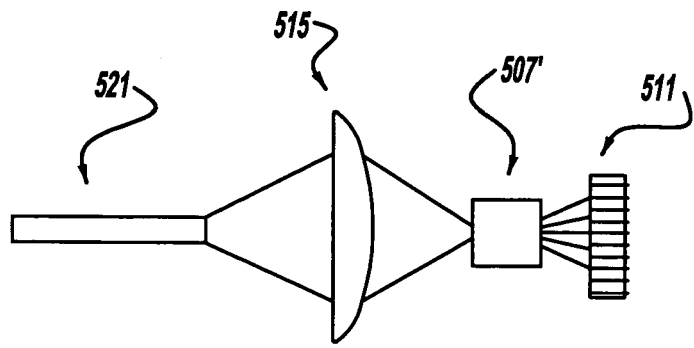

Referring to FIGS. 17, 18A and 18B, a fourth preferred embodiment of the system of the present invention is used for fiber optic communications. Multiple transmission users who are each sending a communications message or signal are using a communications device such as a telephone 491, personal computer, facsimile machine or the like, at remote locations from each other. These remote transmitters are connected to a "smart" main transmitter assembly which includes a computerized, central processing unit 493 through electric wires, fiber optic cables, microwave signals or the like. A phase modulated pulse shaper 505 is actively controlled by CPU 493. Laser 509 and shaper 505 are also contained as part of the main transmitter assembly. Laser 509 emits an ultrashort laser pulse which is carried within a fiber optic cable 497 after shaping. The ultrashort laser beam pulses have a duration of about 100 femtoseconds based on currently available fiber optic cable limitations but pulse durations of less than 50 femtoseconds would be preferred and those of 10 or less femtoseconds would be the most desired if fiber optics allow for such in the future. For example, photonic band gap materials such as optical fibers with holes therein may allow for use of approximately 10 femtosecond pulses.

Pulse shaper/phase mask 505 encodes each laser beam pulse phase, using a binary phase mask. The second harmonics contains multiple peaks, by way of example, but not limitation, in the frequency domain, thus revealing the encoded message. This allows encoding of routing addresses and the associated communications information to be encoded within each laser beam pulse based on CPU control of the laser beam emissions in combination with actively varied shaping of each emitted pulse.

A "dumb" central receiver 501, one that does not require an additional laser or complex computational capabilities, is connected to the downstream end of fiber optic cable 497. Receiver 501 includes a focusing lens 515, a thick SHG crystal 507' and a detector 511. Each laser beam pulse transmitted through fiber optic cable 497 is dispersed onto lens 515 which serves to focus and direct each pulse, in a converging angular manner, onto crystal 507'. A thick optical crystal 507' is defined herein as one having a transmissive path thickness of greater than about 0.5 millimeters while a thin optical crystal 507 (see FIG. 15) is defined herein as having a transmissive path thickness less than about 0.5 millimeters. The preferred thickness for the thick crystal is approximately 3.0 millimeters for 50 femtosecond or less pulse duration and 5.0 millimeters for a 50 to 200 femtosecond pulse duration. Thick crystal 507' creates a second order harmonic and second order spectrum within each pulse as previously shaped by the pulse shaper. In other words, the thick crystal disperses essentially the entire color spectrum without use of a separate spectrometer because of the phase matching angle requirement.

Each separated color frequency angularly dispersed from the thick crystal is encoded by the pulse shaper to contain individual communication routing addresses and the actual communications information, which is then detected by a multiplexer-type of detector 511 such as a CCD camera employing a linear array. Alternately, detector 511 is a two-dimensional array that can be used to achieve higher data densities by adding one more dimension. It is also alternately envisioned that detector 511 is an array of optical fibers that are connected to remote controllers/sub-detectors. The data can be read asynchronously using only the transmission pulse containing the information and not additional reference pulse. A single detector 511 is operable to digitize the detected signals carried in each pulse as separated through the spectrum and transmit them through wires, fiberoptics, microwaves or the like to individual decoding microprocessor controllers 503 within or external to receiver 501. A set of prestored variables or dencryption information or key is located within memory of each controller 503 in order to decode each corresponding digitized communication signal received by detector 511 without requiring synchronous communication transmissions (in other words, a second laser pulse that provides a complimentary phase) from transmitter 495. The decoded communications are then sent to the end users who receive such by telephones 505, personal computers, facsimile machines or the like at the identified routing addresses desired. Alternately, controllers 503 can be replaced by simple light detection devices such as photodiodes which can be employed in a digitized on/off self-switching mode based on the signal detected by detector 511 to control or send information to remote destinations. It is significant that interferometry and synchronous laser pulses are not required for decoding the transmitted information with the presently preferred communications embodiment of the present invention. It is also noteworthy that pulse shaper 505 can encode each pulse by use of second harmonic generation or any other non-linear mixing method including, but not being limited to, frequency mixing, difference frequency mixing, and four wave mixing.

The present invention should be contrasted to a prior experiment which employed a difficult and a synchronous reference pulse at the decoder for supplying a complimentary phase to control the emission of a single specific wavelength. This is disclosed in Z. Zheng and A. Weiner, "Coherent Control of Second Harmonic Generation Using Spectrally Phase Coded Femtosecond Waveforms," *Chemical Physics* 267, p. 161 (2001); this prior approach, however, required pulses which overlap in time and space, which is difficult to control, and only for a single pulse frequency.

While various embodiments have been disclosed herein, it should be appreciated that other modifications may be made that are covered by the system and methods of the present invention. For example, alternate lasers, chemicals, optics and computer controllers can be employed as long as they function as described. The description of the invention is merely exemplary in nature and, thus, variations that do not depart from the gist of the invention are intended to be within the scope of the invention. Such variations are not to be regarded as a departure from the spirit and scope of the invention.

The invention claimed is:

1. A system comprising:
   a) a laser operable to emit a femtosecond laser beam pulse;
   b) a phase shaper operable to shape the pulse with binary phase values; and
   c) a controller operable to automatically control the laser and the shaper, the controller including software instructions operable causing and controlling multiphoton intrapulse interference in the laser beam pulse.

2. The system of claim 1, wherein the shaper employs two phase values separated by $\pi$.

3. The system of claim 1 further comprising multiphoton intrapulse interference phase scan software, for pulse characterization and compensation, used by the controller.

4. The system of claim 1 further comprising evolutionary learning calculations used by the controller.

5. The system of claim 1, wherein the system is employed in multiphoton microscopy.

6. The system of claim 1, wherein the system is employed in an optical communications system.

7. The system of claim 1, wherein the pulse shaper has one of the following pixel resolutions: (a) about 128; (b) about 512; (c) about 640; and (d) about 1024.

8. The system of claim 7, wherein the bandwidth of the laser is dispersed across all pixels of the phase modulator.

9. The system of claim 1, wherein the system is employed in optical coherence tomography.

10. The system of claim 1, wherein the system is employed in microlithography.

11. The system of claim 1, wherein the system is employed in functional imaging.

12. The system of claim 1, wherein the system is employed in quantum information processing.

13. The system of claim 1, wherein the system is employed in nonlinear optical excitation spectroscopy.

14. The system of claim 1, wherein the system is employed in photodynamic therapy.

15. A system comprising:
   a) a laser beam pulse;
   b) a phase shaper operable to shape the laser beam pulse with encoded characteristics and with binary phase value;
   c) a nonlinear optical medium operable to separate multiple frequencies of the pulse;
   d) software instructions operable causing and controlling multiphoton intrapulse interference in the laser beam pulse;
   e) a detection device operable to detect the characteristics of the shaped laser beam pulse as separated by the nonlinear optical medium; and
   f) a unit connected to the device operably decoding the characteristics.

16. The system of claim 15, wherein the laser beam pulse is encoded with a routing address.

17. The system of claim 15 further comprising:
   a main transmitting controller; and
   multiple remote initial-transmitting sources connected to the transmitting controller;
   the main transmitting controller operably causing the pulse shaper to encode multiple successive laser beam pulses differently in an active manner.

18. The system of claim 15 further comprising a fiber optic cable carrying the laser beam pulse from the pulse shaper.

19. A system for use with living tissue, the system comprising:
   a high peak intensity laser beam pulse;
   software instruction operable causing and controlling multiphoton intrapulse interference in the laser beam pulse;
   a device operable to change a characteristic of the pulse prior to emission of the pulse upon the living tissue through use of multiphoton intrapulse interference; and
   wherein nonlinear transitions induced by each pulse are controlled by binary phase shaping and the software instructions.

20. The system of claim 19 wherein the device uses a pulse shaper and the desired excited substances in the tissue undergo two photon absorption.

21. The system of claim 19 wherein the pulse has a duration of less than fifty one femtoseconds and values used in the binary phase shaping are predetermined.

22. The system of claim 19 further comprising generating an optical tomography image produced by the shaped pulse passing through the tissue.

23. The system of claim 19 wherein the device is a pulse shaper which enhances two photon absorption by a therapeutic substance and substantially prevents three photon induced damage of adjacent healthy tissue.

24. The system of claim 19 wherein the device includes a phase modulation mask operably modifying the beam.

25. The system of claim 19 wherein the pulse is shaped to enhance targeted multiphoton damage to modify or destroy certain molecules in the living tissue.

26. The system of claim 19 wherein the multiphoton intrapulse interference operably activates desired photodynamic therapy agents at desired tissue depths.

27. A system for multiphoton microscopy, the system comprising:
   a) a femtosecond laser operable to emit a laser pulse;
   b) a target operable to hold a sample in the pulse;
   c) the sample operably labeled with at least one fluorescent probe;
   d) software instructions operable causing and controlling multiphoton intrapulse interference in the pulse;
   e) a phase shaper operable to shape the pulse in the binary manner to cause selective excitation of the probe and to correct for phase distortions; and
   f) a detector operably detecting an emission from the sample.

28. The system of claim 27, further comprising multiple probes.

29. The system of claim 28, wherein the shaper operably shapes a probe to selectively excite each of the multiple probes.

30. The system of claim 27, wherein the probe includes fluorescent nanoparticles.

31. The system of claim 27, wherein the probe is a chemically sensitive fluorescent probe for detecting at least one of: H+, Na+, and Ca++ ions.

32. The system of claim 27, further comprising learning calculations.

33. The system of claim 27, further comprising a controller operably controlling the laser, the shaper, the target and the detector.

34. The system of claim 33, wherein the controller is part of a microprocessor, and the controller controls multiphoton intrapulse interference in the pulse with binary pulse values used with the binary phase shaper.

35. The system of claim 34, further comprising a data collector operably collecting data from the detector.

36. The system of claim 35, further comprising a data analyzer operably analyzing the data that is collected.

37. The system of claim 27, wherein the shaper is comprised of different phase masks permanently created in a substrate.

38. The system of claim 27, wherein the detector operably converts the emission so that it is viewable by a human eye.

39. The system of claim 27, wherein the sample is labeled with quantum dots.

40. A method for microscopy of a target material containing probes that are excitable by multiphoton multi-photon excitation, the method comprising:
   a) generating a laser pulse;
   b) using programmable instructions to cause and control multiphoton intrapulse interference in the pulse;
   c) shaping the pulse using a binary phase shaper employing binary phase functions so that the pulse selectively excites a desired probe by the multiphoton excitation;
   d) directing the shaped pulse at the target; and
   e) detecting emissions from the target.

41. The method of claim 40, further comprising shaping the pulse by the use of learning calculations.

42. The method of claim 40, wherein the target has multiple probes.

43. The method of claim 42, further comprising shaping a pulse to selectively excite each of the multiple probes.

44. The method of claim 40, further comprising shaping the pulse with a spatial light modulator.

45. The method of claim 40, wherein the laser pulse is less than 51 femtoseconds, further comprising observing the target with a confocal microscope.

46. A method of pulse shaping, the method comprising:
   a) emitting a laser pulse having a duration less than 110 femtoseconds;
   b) directing the pulse into a pulse shaper;
   c) characterization of the pulse using multiphoton intrapulse interference phase software, the software including instructions operable causing and controlling multiphoton intrapulse interference in the pulse if desired; and
   d) shaping the pulse by only two phase values.

47. The method of claim 46, further comprising using the shaped pulse in multi-photon microscopy.

48. The method of claim 46, further comprising using the shaped pulse in optical communications.

49. The method of claim 46, further comprising using the shaped pulse in non-linear optical excitation spectroscopy.

50. The method of claim 46, further comprising using two phases separated by $\pi$.

51. The method of claim 46, wherein the pulse contains data.

52. The method of claim 51, further comprising using a spatial light modulator.

53. The method of claim 52, further comprising shaping the pulse with the spatial light modulator having one of the following pixel resolutions: (a) about 128; (b) about 512; (c) about 640; and (d) about 1024.

54. The method of claim 51, wherein the amount of data transmitted in the pulse is equal to or less than 128 bytes per pulse.

55. The method of claim 46, further comprising using the shaped pulse in microlithography.

56. A method of pulse shaping, the method comprising:
   a) emitting at least one laser pulse;
   b) directing the at least one pulse into a pulse shaper;
   c) shaping the at least one pulse in a binary manner and
   d) characterization of the at least one pulse using multiphoton intrapulse interference phase scan software, the software including instructions operable to cause and control multiphoton intrapulse interference in the pulse if desired.

57. The method of claim 56, further comprising using the shaped pulse in nonlinear optical excitation spectroscopy.

58. The method of claim 46, further comprising using the shaped pulse in optical coherence tomography.

59. The method of claim 56, further comprising using the shaped pulse in multiphoton microscopy.

60. The method of claim 46, further comprising using the shaped pulse in quantum computing.

61. The method of claim 46, further comprising using the shaped pulse in photodynamic therapy.

62. The method of claim 46, further comprising using the shaped pulse in microfabrication.

63. The method of claim 46, further comprising shaping by binary phase shaping.

64. The method of claim 56, further comprising using the shaped pulse in photodynamic therapy on living tissue.

65. The method of claim 56, wherein the at least one pulse has a duration less than 51 femtoseconds.

66. The method of claim 56 further comprising automatically compensating for undesired pulse characteristics.

67. The method of claim 56 further comprising selectively reducing three or more photon excitation.

68. A system comprising:
   a laser operably emitting at least one laser beam pulse of less than 51 femtoseconds;
   a pulse shaper operably controlling a spectral phase of the at least one pulse, the shaper shaping the at least on pulse by only two phase values;
   a detector operably detecting a spectrally dispersed second harmonic of the at least one shaped pulse; and
   a controller connected to the shaper and detector, the controller operably controlling multiphoton intrapulse interference in the at least one pulse, the controller being operable to use software instructions to cause and control multiphoton intrapulse interference in the at least one pulse.

69. The system of claim 68 wherein the at least one pulse has a duration less than 10 femtoseconds.

70. The system of claim 68 further comprising selectively reducing three or more photon excitation.

71. The system of claim 68 wherein a calibrated reference spectral phase in the pulse shaper is used to retrieve an unknown spectral phase in subsequent pulses.

72. The system of claim 68 further comprising using a reference spectral phase including a sinusoidal function with the pulse shaper.

73. The system of claim 68 further comprising using a reference spectral phase including a cubic function with the pulse shaper.

74. The system of claim 68 further comprising a retrieved unknown spectral phase in the at least one pulse in used to calculate a compensation phase that cancels spectral phase distortions in subsequent laser beam pulses.

75. The system of claim 68 further comprising using the shaper and controller to conduct multiphoton intrapulse interference phase scans on subsequent laser beam pulses in an iterative manner to improve the quality of pulse control.

76. The system of claim 1, wherein the controller controls multiphoton intrapulse interference in the pulse with the assistance of the binary phase values.

77. The system of claim 1, wherein the binary phase values are predetermined prior to emission of the pulse without an evolutionary learning algorithm.

78. The system of claim 19, wherein the controller uses multiphoton intrapulse interference phase scan software for pulse characterization and compensation.

79. The system of claim 19, wherein the controller uses evolutionary learning calculations in combination with the binary phase values.

80. The method of claim 56, further comprising creating a transform-limited pulse with the pulse shaper.

81. The method of claim 56, further comprising creating a user-specified shaped pulse with the pulse shaper.

82. The method of claim 56, further comprising obtaining a second harmonic spectrum of the at least one pulse with a second-harmonic generation crystal land spectrometer.

83. The method of claim 56, further comprising:
  (a) introducing a reference phase function into the at least one pulse by the pulse shaper;
  (b) frequency doubling an output;
  (c) detecting the second harmonic spectrum in a spectrometer;
  (d) determining the phase distortion with a controller and
  (e) subtracting the phase distortion when subsequent phase functions are introduced by the pulse shaper to compensate for phase distortions of the input laser pulse.

84. The method of claim 56, wherein the pulse shaper includes a spatial light modulator which both introduces a reference phase and compensates for phase distortions.

85. The method of claim 56, further comprising automatically calculating the second derivative of a spectral phase from a collection of second harmonic spectra obtained as a referenced phase is scanned, and obtaining the spectral phase by integration.

86. The method of claim 56, further comprising introducing a binary phase function to the at least one pulse in addition to a compensation phase.

87. A system comprising:
  (a) a laser emitting a laser beam pulse;
  (b) a shaper operably shaping the pulse with binary phase values; and
  (c) a controller including software instructions being operable to cause and control multiphoton intrapulse interference in the pulse with the assistance of the binary phase values.

88. The system of claim 87, wherein the controller uses multiphoton intrapulse interference phase scan software for pulse characterization and compensation.

89. The system of claim 87, wherein the controller uses evolutionary learning calculations in combination with the binary phase values.

90. The system of claim 87, wherein the bandwidth of the laser is dispersed across all pixels of the phase modulator.

91. The system of claim 87, wherein the system is employed in optical coherence tomography.

92. The system of claim 87, wherein the system is employed in functional imaging.

93. The system of claim 87, wherein the system is employed in photodynamic therapy.

94. The system of claim 87, wherein the pulse has a duration of less than fifty one femtoseconds and values used in the binary phase shaping are predetermined.

95. The system of claim 87, further comprising generating an optical tomography image produced by the shaped pulse passing through the tissue.

96. The system of claim 87, wherein the device is a pulse shaper which enhances two photon absorption by a therapeutic substance and substantially prevents three photon induced damage of adjacent healthy tissue.

97. The system of claim 87, wherein the device includes a phase modulation mask operably modifying the beam.

98. The system of claim 87, wherein the pulse is shaped to enhance targeted multiphoton damage to modify or destroy certain molecules in the living tissue.

99. The system of claim 87, wherein the multiphoton intrapulse interference operably activates desired photodynamic therapy agents at desired tissue depths.

* * * * *

UNITED STATES PATENT AND TRADEMARK OFFICE
CERTIFICATE OF CORRECTION

| | | |
|---|---|---|
| PATENT NO. | : 7,609,731 B2 | Page 1 of 2 |
| APPLICATION NO. | : 10/791377 | |
| DATED | : October 27, 2009 | |
| INVENTOR(S) | : Marcos Dantus, Vadim V. Lozovoy and Matthew Comstock | |

It is certified that error appears in the above-identified patent and that said Letters Patent is hereby corrected as shown below:

Column 3, line 18, "a graphical illustration" should be --are graphical illustrations--.

Column 3, line 31, after "showing", delete "an".

Column 6, line 23, after "determine", delete "of".

Column 6, line 58, "$d^2\phi$" should be --$d^2\varphi$--.

Column 10, line 61, "than" should be --then--.

Column 13, line 47, both occurrences of "$1(\omega)$" should be --$/(\omega)$--.

Column 15, line 16, "$(\omega)a$" should be --$(\omega)+a$--.

Column 16, line 7, "in" should be --is--.

Column 17, line 13, "$\phi$" should be --$\varphi$--.

Column 18, line 4, "HPTS" should be --HTPS--.

Column 18, line 7, "HPTS" should be --HTPS--.

Column 18, line 26, "HPTS" should be --HTPS--.

Column 20, line 17, "$\pi$is" should be --$\pi$ is--.

Column 20, line 52, after "examples", insert --of--.

Column 23, line 7, after "injected", insert --with--.

Column 26, line 59, after "not", insert --to--.

Signed and Sealed this

Fifteenth Day of June, 2010

David J. Kappos
*Director of the United States Patent and Trademark Office*

Column 27, line 27, "A embodiment" should be --An embodiment--.

Column 30, line 33, "complimentary" should be --complementary--.

Column 30, line 52, "complimentary" should be --complementary--.

Column 33, line 59, Claim 54, "claim 51" should be --claim 53--.

Column 34, line 33, Claim 68, "on" should be --one--.

Column 34, line 58, Claim 74, "pulse in" should be --pulse is--.

UNITED STATES PATENT AND TRADEMARK OFFICE
CERTIFICATE OF CORRECTION

PATENT NO. : 7,609,731 B2  Page 1 of 1
APPLICATION NO. : 10/791377
DATED : October 27, 2009
INVENTOR(S) : Dantus et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1065 days.

Signed and Sealed this

Fourteenth Day of December, 2010

David J. Kappos
*Director of the United States Patent and Trademark Office*